(12) United States Patent
Hato et al.

(10) Patent No.: US 7,846,903 B2
(45) Date of Patent: Dec. 7, 2010

(54) TYPE II CUBIC LIQUID CRYSTAL COMPOSITION

(75) Inventors: Masakatsu Hato, Tsukuba (JP); Yoshiji Fujita, Tsukuba (JP); Toshitaka Ota, Tsukuba (JP); Masahisa Tanomura, Chiyoda-ku (JP); Manzo Shiono, Chiyoda-ku (JP)

(73) Assignees: National Institute of Advanced Industrial Science and Technology, Tokyo (JP); Kuraray Co., Ltd., Okayama (JP); Cytopathfinder, Inc., Tokyo (JP)

( * ) Notice: Subject to any disclaimer, the term of this patent is extended or adjusted under 35 U.S.C. 154(b) by 581 days.

(21) Appl. No.: 11/665,776

(22) PCT Filed: Oct. 19, 2005

(86) PCT No.: PCT/JP2005/019639

§ 371 (c)(1),
(2), (4) Date: Apr. 19, 2007

(87) PCT Pub. No.: WO2006/043705

PCT Pub. Date: Apr. 27, 2006

(65) Prior Publication Data

US 2008/0113923 A1 May 15, 2008

(30) Foreign Application Priority Data

Oct. 19, 2004 (JP) .............................. 2004-304952

(51) Int. Cl.
| | |
|---|---|
| C09K 19/06 | (2006.01) |
| C07C 9/22 | (2006.01) |
| C07H 15/04 | (2006.01) |
| C07D 307/62 | (2006.01) |
| C07K 17/04 | (2006.01) |
| C07K 17/10 | (2006.01) |
| A61K 31/70 | (2006.01) |
| A61K 31/341 | (2006.01) |
| A61K 31/185 | (2006.01) |

(52) U.S. Cl. ........................ 514/25; 514/473; 514/513; 514/723; 252/299.61; 530/350; 536/4.1; 549/315; 554/213

(58) Field of Classification Search ........................ None
See application file for complete search history.

(56) References Cited

U.S. PATENT DOCUMENTS 5,143,934 A * 9/1992 Lading et al. ................ 514/396

FOREIGN PATENT DOCUMENTS

| JP | 61-137874 A | 6/1986 |
| JP | 2001-328921 A | 11/2001 |
| JP | 2002-20236 A | 1/2002 |
| JP | 2002-226497 A | 8/2002 |

OTHER PUBLICATIONS

Definition "hydrophilic", Merriam-Webster Online Dictionary, available at http://www.merriam-webster.com/dictionary/hydrophilic, last viewed Jul. 30, 2009.*
Kouda, Yoshio and Shuppan, Sankyo, "Formulation Design iwth Organic Conception Diagram", Nihon Emulsion Co., Ltd (2001), available at http://www.nihon-emulsion.co.jp/pdf/ocdbook_e.pdf.*
Masakatsu Hato et al., "Aqueous phase behavior of A 1-o- Phytanyl-β-D-Xyloside/Water System. Glycolipid-Based Biocontinuous Cubic Phases of Crystallographic Space Groups PN3M and IA3D.", Langmuir, Dec. 21, 2004, p. 11366-11373, vol. 20, No. 26.
Thomas Abraham et al., "Polymer-Dispersed Bicontinuous Cubic Glycolipid Nanoparticles", Biotechnology Progress, 2005, p. 255-262, vol. 21, No. 1.
Masakatsu Hato et al., "Alkylglycosides with an Isoprenoid-Type Hydrophobic Chain Can Afford Greater Control of Aqueous Phase Structures at Low Temperatures.", Langmuir, 2002, pp. 3425-3429, vol. 18, No. 9.
Masakatsu Hato et al., "isoprenoid chain-type glycolipid (alkylglycoside): Formation of inverted cubic liquid crystals and structures thereof.", The Chemical Society of Japan, Mar. 3, 2003, p. 383, 83$^{rd}$, (1) , 4H2-13 with an English language abstract.
Thomas Abraham et al., "Glycolipid based cubic nanoparticles: preparation and structural aspects.", Colloids and Surfaces B: Biointerfaces, May 15, 2004, p. 107-117, vol. 35, No. 2.
Itaru Yamashita et al., "Small angle X-ray scattering from lamellar phase for β-3,7- Dimethyloctylglucoside/water system"comparison with β-n-alkylglucosides., Colloids and Surfaces A: Physiochem. Eng. Aspects, Dec. 10, 2004, p. 485-490, vol. 250, Nos. 1-3.
Rajesh A. Salkar et al., "Alkylglucosides with isoprenoid-type hydrophobic chains—effects of Hydrophobic chain size on the aqueous behavior.", Chemistry and Physics of Lipids, Jan. 2004, p. 65-75, vol. 127, No. 1.

(Continued)

*Primary Examiner*—Shaojia Anna Jiang
*Assistant Examiner*—Bahar Schmidtmann
(74) *Attorney, Agent, or Firm*—Sughrue Mion, PLLC

(57) ABSTRACT

A cubic liquid crystal composition comprising at least one amphiphilic compound having the following general formula (1) and having an IV/OV value of 0.65 to 0.95, and water or an aqueous medium:

(1)

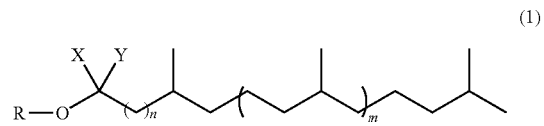

wherein R represents a hydrophilic group; X and Y each independently represent a hydrogen atom or together form an oxygen atom; n is an integer of 0 to 4; and m is an integer of 0 to 3.

20 Claims, 14 Drawing Sheets
(2 of 14 Drawing Sheet(s) Filed in Color)

OTHER PUBLICATIONS

Masakatsu Hato et al., "Novel Alkylpolyglycosides with Krafft temperatures of 0° C or lower.", The Chemical Society of Japan, Mar. 15, 2001, p. 462, $79^{th}$ (1) with an English language abstract.

Yohann Misquitta et al., "Rational design of lipid for membrane protein crystallization.", Journal of Structural Biology, Nov. 2004, p. 169-175, vol. 148, No. 2.

Masakatsu Hato et al., "Glycolipid liquid crystals- structural regulation and application to membrane protein system", The $55^{th}$ Divisional Meeting on Colloid and Interface Chemistry, Sep. 2, 2002, p. 42 with an English language abstract.

* cited by examiner

Water channel

Temperature (°C)

A

B

A 5 min. later   30 min. later 3 hr. later   24 hr. later

α-galactosidase-embedded cubic liquid crystal

B 5 min. later   30 min. later 3 hr. later   24 hr. later

β-galactosidase-embedded cubic liquid crystal

A

B

TYPE II CUBIC LIQUID CRYSTAL COMPOSITION

TECHNICAL FIELD

The present invention relates to a type II cubic liquid crystal composition and a drug delivery system (abbrev. "DDS") and a cosmetic product utilizing such type II cubic liquid crystal composition. The present invention also relates to a method for crystallizing a protein using a type II cubic liquid crystal composition.

BACKGROUND ART

Many lipids are amphiphilic substances having hydrophilic and hydrophobic groups in the same molecules (hereafter referred to as "amphiphilic lipid(s)") and spontaneously form molecular assemblies of various shapes in water. Representative examples of amphiphilic lipids include: synthetic surfactants, soaps, naturally occurring complex lipids such as lecithin, and block copolymers having hydrophobic and hydrophilic chains.

Amphiphilic lipids form molecular assemblies of various shapes in water at the Krafft temperature ($T_K$; it may also be referred to as the "Krafft eutectic temperature", "Krafft point" or the like) or higher, determined depending on the type or concentration of the lipid (see, Laughlin, R. G., "The Aqueous Phase Behavior of Surfactants," 1994, Academic Press, London, pp. 106-117). Examples of such molecular assemblies include closed micelles with outward-directed hydrophilic groups (e.g., spherical micelles or rod-like micelles), closed inverted micelles with outward-directed hydrophobic groups, sponge phases comprising randomly continuous bilayers in which two hydrophobic groups or two hydrophilic groups of the amphiphilic lipid are arranged opposite each other, and various lyotropic liquid crystal phases. Known examples of lyotropic liquid crystal phases are hexagonal liquid crystals and inverted hexagonal liquid crystals in which cylindrical assemblies of unlimited lengths form two-dimensional hexagonal lattices, lamellar liquid crystals in which bilayer sheets are laminated at constant intervals in a Z-axis direction, cubic liquid crystals having three-dimensional lattice structures, and the like.

These molecular assemblies are put to various applications in fields relating to, for example, cosmetic and pharmaceutical products. For example, development of a drug delivery system (DDS) utilizing amphiphilic lipid is very active, and many forms of drug delivery carriers have been produced (see, JP Patent Publication (kohyo) No. 2002-505307 A and JP Patent Publication (kokai) No. 2001-231845 A), including a drug delivery system comprising drugs embedded in an aqueous phase or lipid bilayer of a liposome prepared from lamellar liquid crystals (see, Lasic D. D., TIBTECH 16, 1998, pp. 307-321).

Among molecular assemblies, bicontinuous cubic liquid crystals (which will be described in 1-(1) below) have unique liquid crystal structures-comprising water (or an aqueous medium) portions with diameters of the order of nm scale, which are in communication with the outside (hereafter referred to as "water channel(s)"), and curved lipid bilayers. Accordingly, bicontinuous cubic liquid crystals are capable of embedding greater amounts of both fat-soluble drugs and water-soluble drugs, they have more stable structures, and they have greater mechanical strength than liposomes or micelles. Further, cubic liquid crystals are capable of incorporating water-soluble proteins in water channels and hydrophobic membrane proteins in lipid bilayers. Thus, cubic liquid crystals have drawn attention as novel drug delivery carriers that differ from liposomes or micelles (Engstrom, S., Lipid Technol. 2, 1990, pp. 42-45; Shah, J. C., et al., Adv. Drug Delivery Reviews 47, 2001, pp. 229-**250; Ganem-Quintanar, A., Quintanar-Guerrero, D., and Buri, P., Drug Development and Industrial Pharmacy, 26(8), 2000, pp. 809-820; and Drummond, C. J. and Fong, C., "Surfactant self-assembly objects as novel drug delivery vehicles." Curr. Opin. Colloid Interface Sci., 4, 2000, pp. 449-456).

A majority of cubic liquid crystals found in an amphiphilic lipid/water system can remain stable only in a narrow concentration range between other phase regions, such as aqueous micelle solution, hexagonal liquid crystals, lamellar liquid crystals, and inverted hexagonal liquid crystals that account for the wide area of a phase diagram for a two-component system of amphiphilic lipid/water (Fontell, K. Colloid & Polymer Sci., 268, 1990, pp. 264-285). Thus, use of cubic liquid crystals as drug delivery carriers or the like has difficulty. Since cubic liquid crystals of monoacylglycerols such as monoolein or phytantriol (Barauskas, J., Landh, T., Langmuir, 2003, 19, pp. 9562-9565) are "type II cubic liquid crystals" (described below) wherein a cubic phase is adjacent to an aqueous phase on a phase diagram for the two-component system of amphiphilic lipid/water, they are relatively stable in the presence of excess water. Thus, application thereof for a drug delivery system or the like has been attempted. Cubic liquid crystals of phytantriol are transformed into inverted hexagonal liquid crystals at about 40° C. or higher, and therefore the stability thereof is problematic in high-temperature regions. Further, upon embedding of fat-soluble drugs such as vitamin A therein, maintenance of the cubic liquid crystal structure of phytantriol has become difficult. Among the aforementioned monoacylglycerols, the Krafft temperatures of monomyristolein, monopentadecenoin, and monooctadecanoin, for example, are as high as 35° C. (Briggs, J. Caffrey, M. Biophys. J., 66, 1994, pp. 573-587), 30° C. (Briggs, J. Caffrey, M. Biophys. J., 67, 1994, pp. 1594-1602), and 80° C. (Lutton E. S., J. Am. Oil Chem. Soc., 42, 1965, pp. 1068-1070), and they cannot form cubic liquid crystals at room temperature. Thus, such substances are not suitable for drug delivery carriers. In contrast, the Krafft temperature of monoolein or monovaccenin having unsaturated fatty acid in a hydrophobic chain is as low as 15° C. (Qiu, H., and Caffrey, M., Biomaterials 21, 2000, pp. 223-234; Qui, H., Caffrey, M., J. Phys. Chem. B. 102, 1998, pp. 4819-4829). It is no exaggeration to say that conventional studies concerning drug delivery systems or the like utilizing cubic liquid crystals have been limited to cubic liquid crystals of monoolein (U.S. Pat. Nos. 5,531,925; 5,196,201; 6,656,385; 5,143,934; 5,593,663; 5,756,108; JP Patent Publication (kohyo) No. 2004-502524; Drummond, C. J. and Fong, C., "Surfactant self-assembly objects as novel drug delivery vehicles." Curr. Opin. Colloid Interface Sci., 4, 2000, pp. 449-456). However, monoolein is susceptible to oxidation, and it cannot remain stable due to rapid enzymatic degradation into fatty acid and glycerine in the blood (Leesajakul, W., Nakano, M., Taniguchi, A., Handa, T., Colloid Surf., B., 2004, pp. 253-258). In addition, it disadvantageously becomes unstable when stored at refrigeration temperatures (lower than 6° C.) or subjected to experimentation at such temperatures.

In the past, therefore, the present inventors developed glycolipids having isoprenoid-type hydrophobic chains having relatively low Krafft temperatures (JP Patent Publication (kokai) No. 8-245682 A; JP Patent Publication (kokai) No. 2002-226497 A). Among such glycolipids, 1-O-(3,7,11,15-tetramethylhexadecyl)-β-D-xyloside formed cubic liquid crystals in the presence of water, and the Krafft temperature thereof was 10° C. (Hato, M., Minamikawa, H., Salkar, R. A., Matsutani, S. Langmuir, 18 (2002) pp. 3425-3429; Hato, M., Minamikawa, H., Salkar, R. A., Matsutani, S. Progr. Colloid Polym. Sci., 123 (2004) pp. 56-60; Hato, M., Yamashita, I., Kato, T., Abe Y., Langmuir, (2004) 20, pp. 11366-11373). In recent years, a lipid that has a Krafft temperature of 6° C. and belongs to monoacylglycerols has been reported (Mesquitta, Y., Cherezov, V., Havas, F., Patterson, S., Mohan, J. M., Wells, A. J., Hart, D. J., Caffrey, M., J. Structural Biol., (2004) 148, pp. 169-175). However, such lipids are not suitable for storage or experimentation at refrigeration temperatures (about 4° C.) or lower, and improvement is required.

DISCLOSURE OF THE INVENTION

The present invention is intended to resolve the aforementioned drawbacks and to provide a cubic liquid crystal composition that is highly stable at a low temperature (lower than 6° C.) and has regulatable physical properties and structure and a method for producing the same.

The present inventors have conducted concentrated studies in order to attain the above objects. As a result, they discovered that type II cubic liquid crystals could be formed at low temperatures, such as lower than 6° C., with the use of a given amphiphilic lipid or a mixture thereof. The present invention has been completed based on such finding and thus includes the following.

[1] A cubic liquid crystal composition comprising at least one amphiphilic compound having following general formula (1) and having an IV/OV value of 0.65 to 0.95 and water or an aqueous medium:

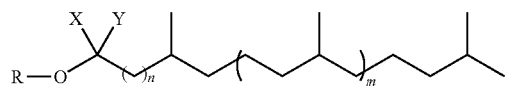

formula (1)

wherein R represents a hydrophilic group; X and Y each independently represent a hydrogen atom or together form an oxygen atom; n is an integer of 0 to 4; and m is an integer of 0 to 3.

[2] A cubic liquid crystal composition comprising at least one amphiphilic compound having following general formula (1) and having a Krafft temperature of lower than 6° C., and water or an aqueous medium:

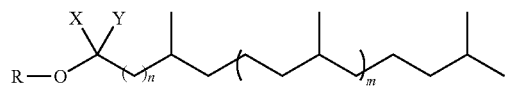

(1)

wherein R represents a hydrophilic group; X and Y each independently represent a hydrogen atom or together form an oxygen atom; n is an integer of 0 to 4; and m is an integer of 0 to 3.

[3] The cubic liquid crystal composition according to [1] or [2], wherein said amphiphilic compound is at least one selected from the group consisting of following formulae (2) to (12) and (15).

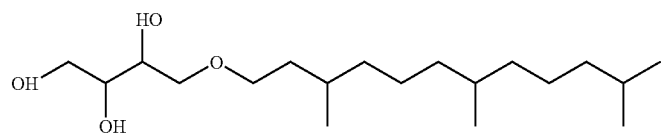

(2)

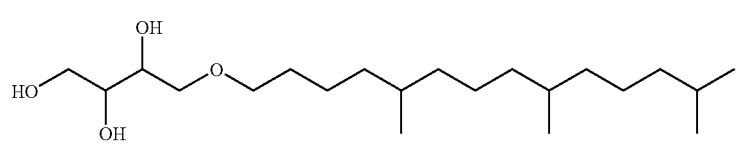

(3)

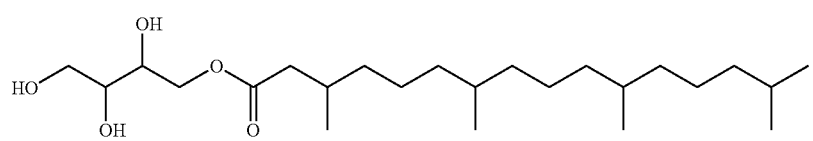

(4)

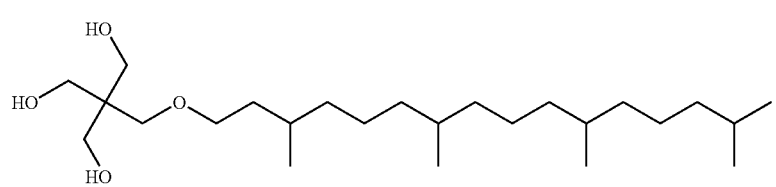

(5)

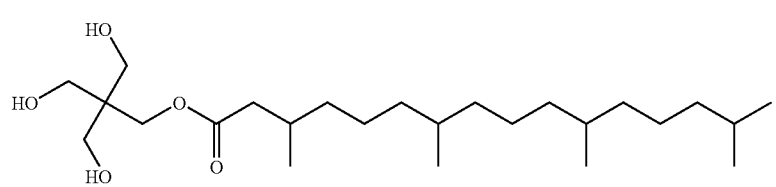

(6)

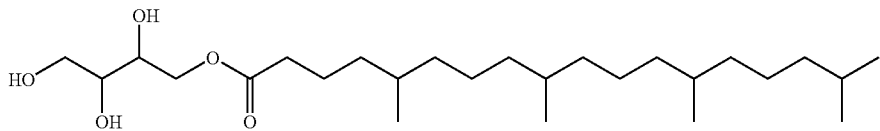
(7)

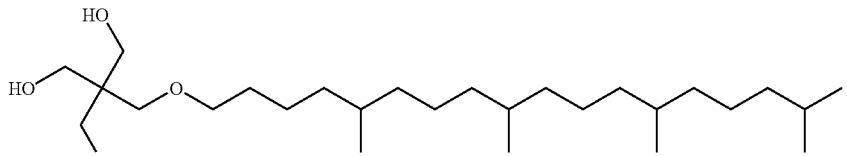
(8)

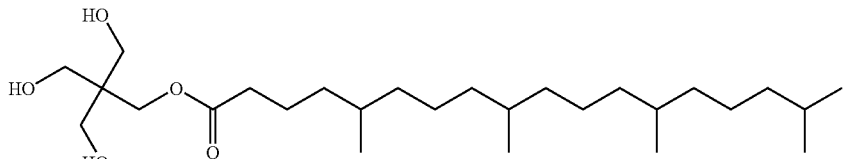
(9)

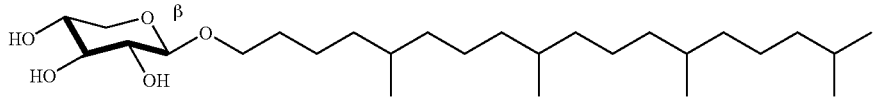
(10)

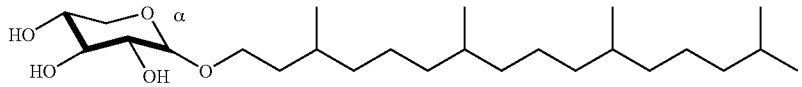
(11)

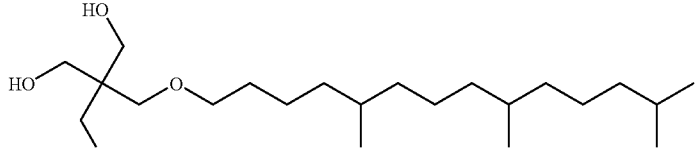
(12)

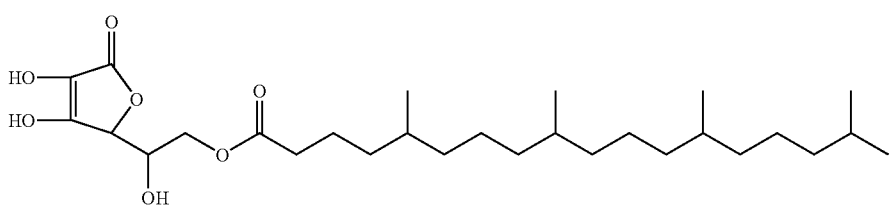
(15)

[4] The cubic liquid crystal composition according to [1] or [2], which further comprises at least one amphiphilic lipid different from said amphiphilic compound.

[5] The cubic liquid crystal composition according to [3], which further comprises at least one amphiphilic lipid different from the said amphiphilic compounds having formulae (2) to (12) and (15).

[6] A complex comprising a drug (excluding a lysosomal enzyme) embedded in the cubic liquid crystal composition according to any of [1] to [5].

[7] A pharmaceutical composition comprising the complex according to [6]. This composition is preferably a controlled release composition.

[8] A complex comprising an active cosmetic ingredient (excluding a lysosomal enzyme) embedded in the cubic liquid crystal composition according to any of [1] to [5].

[9] A cosmetic composition comprising the complex according to [8].

[10] An amphiphilic compound having any of following formulae (2) to (12) and (15).

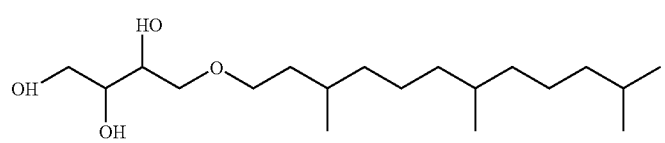
(2)

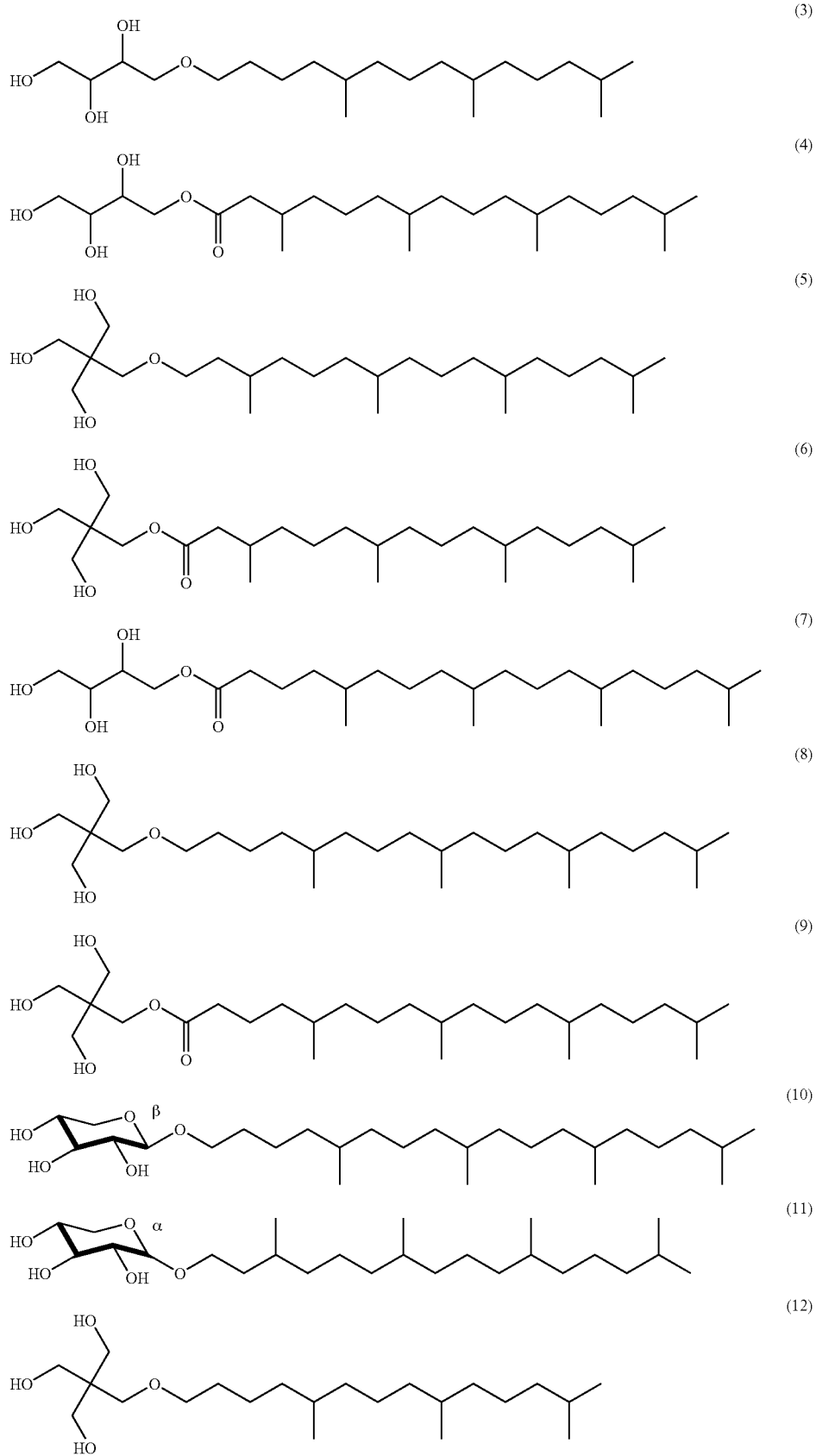

-continued

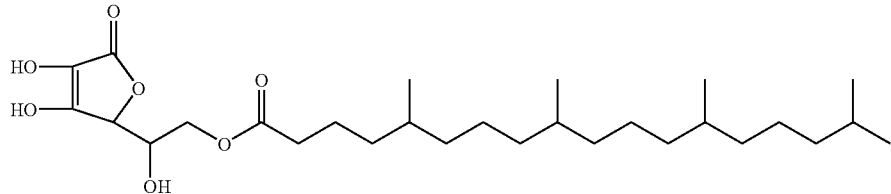

(15)

[11] A method for modifying a liquid crystal structure and physical properties of a cubic liquid crystal composition comprising adding at least one amphiphilic lipid different from compounds having the above formulae (2) to (12) and (15) to at least one amphiphilic compound selected from the group consisting of compounds having the above formulae (2) to (12) and (15) and mixing them in water or an aqueous medium.

[12] A method for increasing the stability of a liquid crystal structure of a cubic liquid crystal composition comprising mixing at least one amphiphilic compound having following formula (1) and having an IV/OV value of 0.65 to 0.95 with a curvature-regulating substance in water or an aqueous medium:

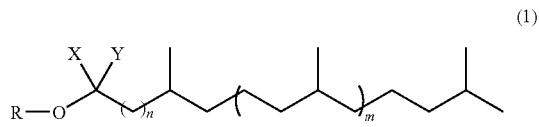

(1)

wherein R represents a hydrophilic group; X and Y each independently represent a hydrogen atom or together form an oxygen atom; n is an integer of 0 to 4; and m is an integer of 0 to 3.

In this method, the curvature-regulating substance is preferably a triglyceride-containing substance, and it is more preferably olive oil. Further, a protein may be further mixed together with the above amphiphilic compound and curvature-regulating substance. Through the mixing with a protein in this process, such protein becomes embedded in the cubic liquid crystal composition.

[13] A method for crystallizing a protein comprising embedding a protein in the cubic liquid crystal composition according to any of [1], [2], or [4] and growing a protein crystal in the resulting complex. The cubic liquid crystal composition used in this process particularly preferably comprises at least one compound selected from the group of compounds having following formulae (2) to (13) and (15) as the aforementioned amphiphilic compound.

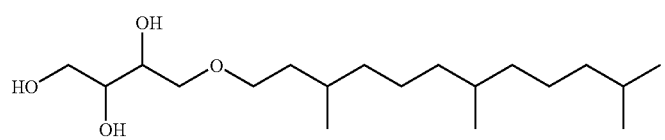

(2)

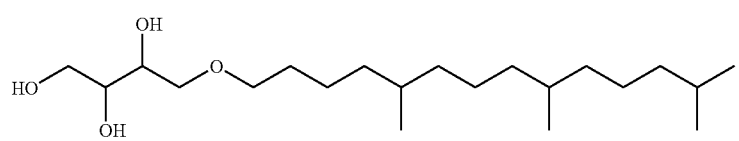

(3)

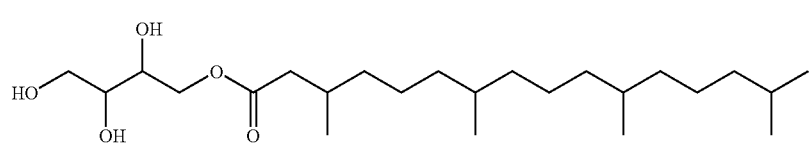

(4)

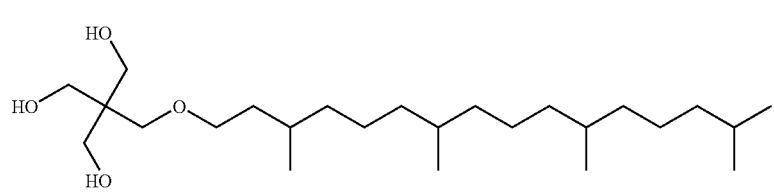

(5)

-continued

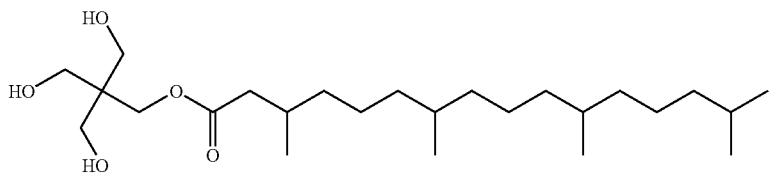
(6)

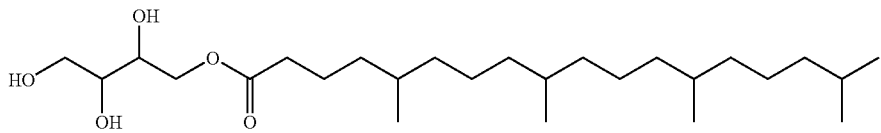
(7)

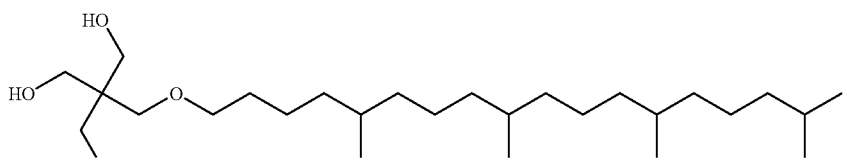
(8)

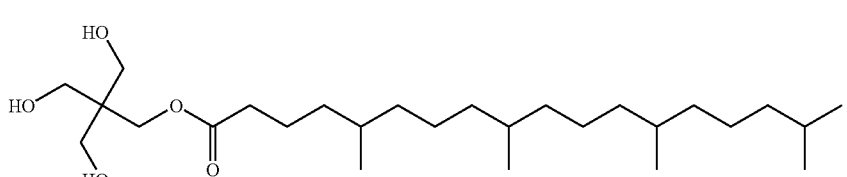
(9)

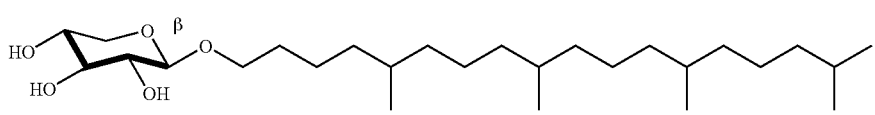
(10)

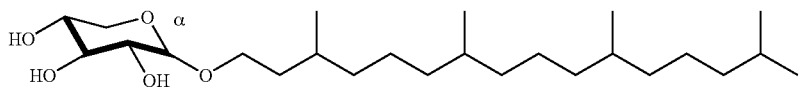
(11)

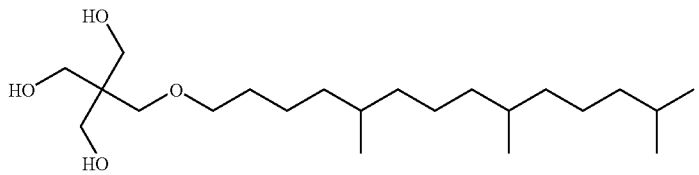
(12)

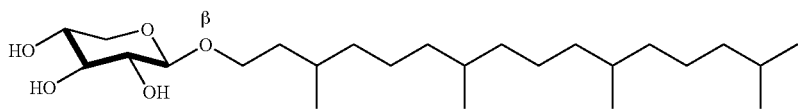
(13)

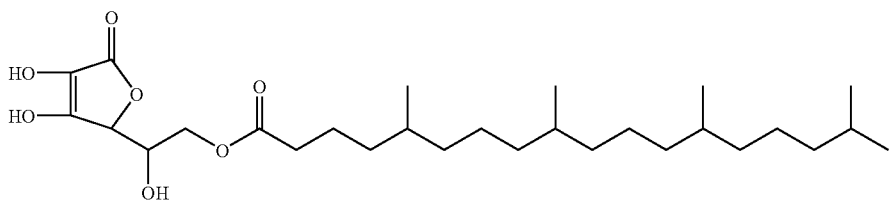
(15)

The term "cubic liquid crystal composition" used in the present invention refers to a composition in which a cubic liquid crystal phase is formed by the amphiphilic compound of the present invention (and optionally another amphiphilic lipid or the like) and water or an aqueous medium.

In this description, a compound having the general formula (1) is referred to as an amphiphilic compound, and "an amphiphilic lipid" is used in a broad sense that includes, but is not limited to, such amphiphilic compound.

The cubic liquid crystal composition of the present invention can comprise various compounds (e.g., drugs) embedded therein by a simple procedure. In particular, the cubic liquid crystal composition of the present invention can comprise large quantities of macromolecules or hydrophobic compounds embedded in its liquid crystals, such macromolecules or hydrophobic compounds being generally less likely to become embedded in a liquid crystal structure in large quantities. The cubic liquid crystal composition of the present invention remains highly stable at low temperatures (lower than 6° C.), at which it has been difficult to stably handle a liquid crystal by conventional techniques. Thus, such composition is particularly useful when used for pharmaceutical, cosmetic, or other products that are required to be produced and stored at low temperatures. The cubic liquid crystal composition of the present invention is also stable under strong acidic and strong alkaline conditions. Further, the cubic liquid crystal composition of the present invention can retain embedded drugs, active cosmetic ingredients, and the like and preserve the activity thereof for a long period of time. The cubic liquid crystal composition of the present invention can also protect the embedded drugs or active cosmetic ingredients from destruction by degrading enzymes or the like. Further, the cubic liquid crystal composition of the present invention is capable of controlled release of embedded drugs or active cosmetic ingredients from its liquid crystal structure.

By employing the method for modifying the structure and physical properties of cubic liquid crystals according to the present invention, the cubic liquid crystal structure can be optimized for drugs or active cosmetic ingredients to be embedded. The rate of controlled release or the like can also be regulated by the method in accordance with applications.

A pharmaceutical or cosmetic composition comprising a complex of the cubic liquid crystal composition of the present invention and a drug or an active cosmetic ingredient, respectively can allow the embedded drug or active cosmetic ingredient to act at the site of application for a long period of time.

With the use of an amphiphilic compound having the aforementioned formula (1) and having an IV/OV value of 0.65 to 0.95, and preferably an amphiphilic compound having any of formulae (1) to (12) and (15), in the method for producing a cubic liquid crystal composition, a cubic liquid crystal composition with improved low-temperature stability can be produced. In addition, a cubic liquid crystal composition with a liquid crystal structure or physical properties modified in accordance with applications can be produced.

Concerning the cubic liquid crystal composition of the present invention, the stability of the cubic liquid crystal structure can be increased with the addition of a curvature-modifying lipid to the aforementioned amphiphilic compound at the time of production of the cubic liquid crystal composition of the present invention, compared with the cubic liquid crystal composition produced without the addition of a curvature-modifying lipid. Such method for increasing stability of a liquid crystal structure of a cubic liquid crystal composition can be used for further stabilizing the release of drugs embedded in the cubic liquid crystal composition, for example.

The cubic liquid crystal composition of the present invention is useful as a field for crystallization of various proteins. The method for crystallizing a protein using the cubic liquid crystal composition of the present invention can highly facilitate crystallization of various proteins and can in turn produce protein crystals having good quality and sufficient sizes, e.g., in crystalline sizes suitable for X-ray analysis.

This description includes the disclosure of Japanese Patent Application No. 2004-304952, from which the present application claims priority.

BRIEF DESCRIPTION OF THE DRAWINGS

The patent or application file contains at least one drawing executed in color. Copies of this patent or patent application publication with color drawing(s) will be provided by the Office upon request or payment of the necessary fee.

PREFERRED EMBODIMENTS OF THE INVENTION

1. Cubic liquid Crystal Composition (1) General Structures and Features of Cubic Liquid Crystals Cubic liquid crystals comprise, as constitutional units, various forms of molecular assemblies (e.g., spherical, rodlike, or bilayer membrane assemblies) formed by amphiphilic lipids and have regular three-dimensional structures. Since cubic liquid crystals are optically transparent and free of birefringence (i.e., optically isotropic), they appear uniformly dark via polarizing microscopic observation under a crossed Nicol condition and do not show any visible texture (i.e., isotropic texture).

Cubic liquid crystals are classified into bicontinuous and discontinuous types based on differences in continuity of hydrophobic regions and hydrophilic regions in the units of liquid crystal structure. The "bicontinuous" cubic liquid crystals are composed of hydrophilic regions (containing hydrophilic groups of amphiphilic lipids and water or an aqueous medium) and hydrophobic regions that independently have continuous or connected structures in the units of liquid crystal structure. In the "discontinuous" cubic liquid crystals, one of the hydrophobic and hydrophilic regions in the unit of a liquid crystal structure has a continuous structure, and the other has a discontinuous structure (e.g., a spherically closed structure).

Cubic liquid crystal structures are classified into type I and type II structures. When a lipid molecular membrane that forms a unit of a liquid crystal structure is curved toward the hydrophobic group and forms an "oil in water type" structure, such structure is referred to as a type I cubic liquid crystal. When a lipid molecular membrane is curved toward the hydrophilic group of a lipid molecule and water (or an aqueous medium) and forms a "water in oil type" structure, such structure is referred to as a type II cubic liquid crystal. Type I can be distinguished from type II based on the phase behavior of the amphiphilic lipid/water system. In the case of type I, for example, as the water content of the amphiphilic lipid/water system is increased, the liquid crystal structure is transformed into another liquid crystal structure (e.g., lamellar liquid crystal), a micelle, and then a homogeneous aqueous solution at last. In the case of type II liquid crystal, however, water content exceeding a given level results in a two-phase condition of "liquid crystals and excess water" wherein liquid crystals containing a saturating amount of water and excess water coexist. Thus, the type II liquid crystals are not converted to a homogeneous aqueous solution even if increased amount of water is added.

Figure 1:
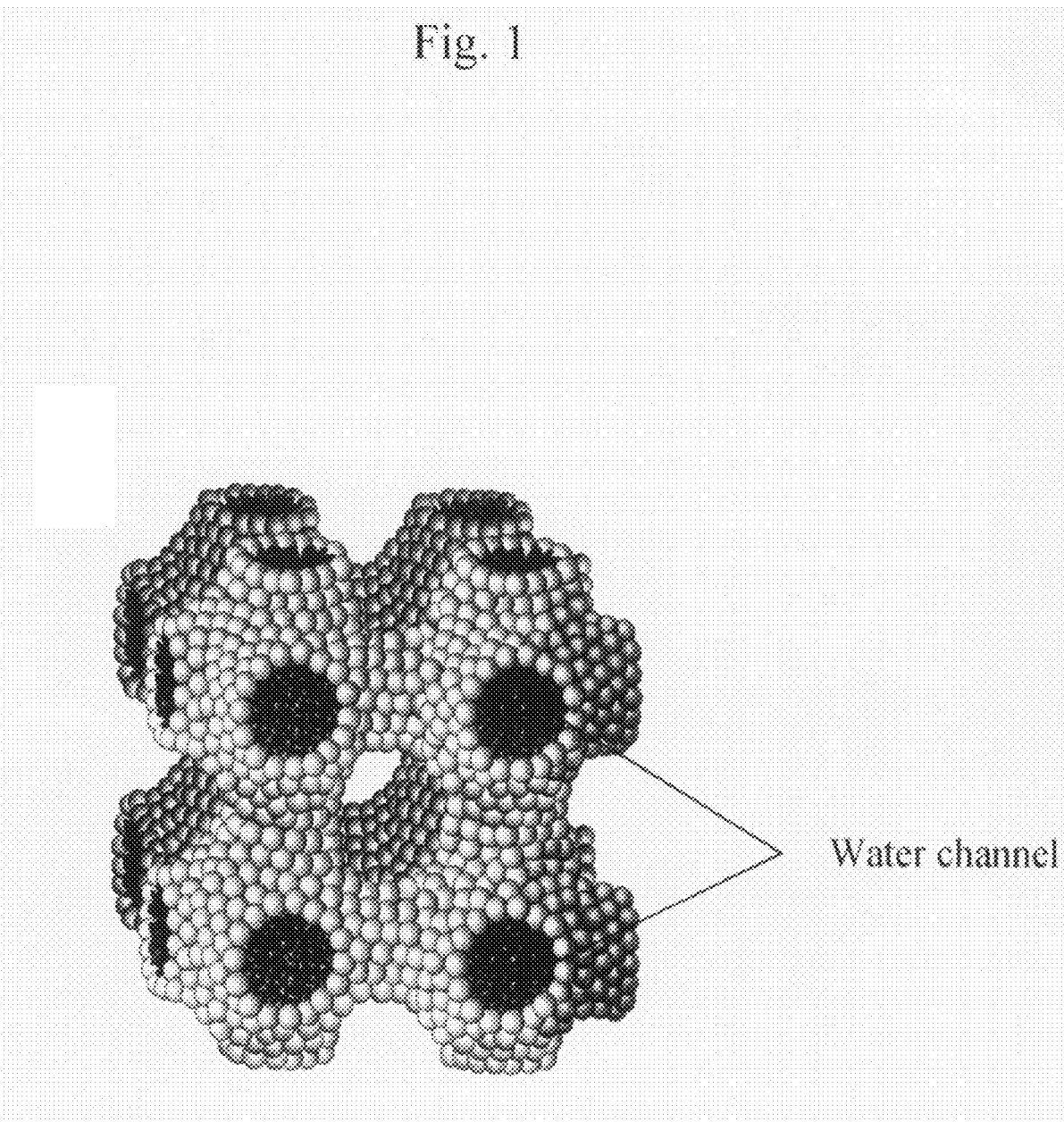
FIG. 1 shows a model structure of a cubic liquid crystal.

FIG. 1 shows a model structure of a cubic liquid crystal that belongs to the crystallographic space group Im3m (Evans, F., Wennerstrom, H., "The Colloidal Domain," VHC, 1994).

Liquid crystals such as cubic liquid crystals formed by amphiphilic lipids are formed only at the Krafft temperature ($T_K$), as determined depending on types and concentrations of amphiphilic lipids, or higher. Furthermore, liquid crystals generally undergo a phase transition upon changes in the concentration of the amphiphilic lipid or temperature. Accordingly, the maximal temperature ($T_{max}$) at which a given liquid crystal structure can be stably present is also determined depending on lipid type and concentration of amphiphilic lipid. Thus, a liquid crystal formed by a given type of amphiphilic lipid is stably formed in the temperature range between $T_K$ and $T_{max}$. The correlation between $T_K$-$T_{max}$ and the concentration of the amphiphilic lipid is generally indicated as a "concentration-temperature dependent phase diagram" of the amphiphilic lipid/water system. The Krafft temperature of the amphiphilic lipid can be determined by a method known in the art, such as a method involving the preparation of such a phase diagram (e.g., Laughlin, R. G., "The Aqueous Phase Behavior of Surfactants," 1994, Academic Press London, pp. 106-117). The Krafft temperature of a mixture of two or more amphiphilic lipids can be determined by the same method.

In many cases, cubic liquid crystals are formed only in a narrow amphiphilic lipid concentration range. Thus, very minor changes in concentration result in the transformation of liquid crystal structures, and it is very difficult to utilize the cubic liquid crystal structure, in general.

(2) Structures and Features of Cubic Liquid Crystals in the Cubic Liquid Crystal Composition of the Present Invention In the cubic liquid crystal composition of the present invention, cubic liquid crystals of a bicontinuous type II structure are formed by one or more amphiphilic lipids according to the present invention (which is described in "(3) Production of cubic liquid crystal composition" below).

The cubic liquid crystal of the present invention has a three-dimensional regular structure comprising a curved amphiphilic lipid bilayer portion and a continuous water channel, which has a diameter of typically about 2 to 20 nm (the diameter is not particularly limited to this range), as shown in FIG. 1.

The cubic liquid crystals in the cubic liquid crystal composition of the present invention are stably formed in a wide temperature range and a wide amphiphilic lipid concentration range. In the type II cubic liquid crystals of the present invention, in particular, even when the water content of the amphiphilic lipid/water system exceeds the maximal level that can be contained within the liquid crystal structure, excess water (more precisely, a dilute aqueous solution of trace amounts of amphiphilic lipid molecules) is separated from the liquid crystal structure to form an aqueous phase, a two-phase condition comprising water-saturated cubic liquid crystals and excess water is realized, and the liquid crystal structure is maintained. The feature of the liquid crystal structure being maintained in the presence of excess water is advantageous when producing pharmaceutical or cosmetic products with high water contents. In addition, such feature can be very convenient when a cubic liquid crystal composition is used as a carrier for the drug delivery system, for example. The concentration of amphiphilic lipid in the cubic liquid crystal composition of the present invention (e.g., the concentration of amphiphilic compound of the present invention) is not particularly limited. It may be generally between 0.1% and 90% by mass, 80% by mass or lower, 70% by mass or lower, or 50% by mass or lower, depending on amphiphilic lipid type, temperature, or other conditions. In the present description, the terms "concentration of amphiphilic lipid" and "concentration of amphiphilic compound" each refer to the proportion of mass (% by mass) of amphiphilic lipid or amphiphilic compound to a total mass of a mixed system of the amphiphilic lipid or amphiphilic compound and water or an aqueous medium. In particular, the term "total concentration of amphiphilic compound (lipid)" refers to the proportion of mass (% by mass) of two or more amphiphilic lipids or amphiphilic compounds to a total mass of a mixed system of the two or more amphiphilic lipids or amphiphilic compounds and water or an aqueous medium.

For the purpose of production of the cubic liquid crystal composition of the present invention, for example, the concentration of amphiphilic lipid is preferably selected so that cubic liquid crystals are selectively formed. In general, a single-phase region of a cubic liquid crystal often appears when the concentration of amphiphilic lipid is 40% to 90% by mass. Thus, cubic liquid crystals are preferably produced in such a concentration range. More specifically, the concentration-temperature range that yields a single-phase region of a cubic liquid crystal depends on the amphiphilic lipid type. Thus, the concentration may be selected based on the "concentration-temperature dependent phase diagram" of the amphiphilic lipid/water system.

In one embodiment, if once a cubic liquid crystal composition is produced with the use of an amphiphilic lipid in a given concentration range (e.g., a typical concentration range at the time of production), optionally the cubic liquid crystal composition may be diluted with water or an aqueous medium. Such diluted cubic liquid crystal composition is also within the scope of the cubic liquid crystal composition of the present invention. Although the dilute composition has a concentration of amphiphilic lipid (or a concentration of amphiphilic compound) lower than that of the initially produced cubic liquid crystal composition, a cubic liquid crystal structure is stably maintained even though the concentration of amphiphilic lipid (or the concentration of amphiphilic compound) is diluted to, but not limited to, about 0.1% by mass, because the two-phase condition of water-saturated cubic liquid crystals and excess water is a thermodynamically stable condition in a region of a low concentration of amphiphilic lipid as described above.

In the cubic liquid crystal composition of the present invention, stable bicontinuous type II cubic liquid crystals are formed at low temperatures, such as lower than 6° C. In the liquid crystal composition of the present invention, stable bicontinuous type II cubic liquid crystals are typically formed between −10° C. (or at the freezing temperature of the aqueous medium used or higher) and 80° C., and preferably between 0° C. and 50° C. The Krafft temperature of the amphiphilic lipid can be easily determined by, for example, DSC assay of an aqueous solution containing 1% to 85% by mass of amphiphilic lipid or by observing the melting behavior of the amphiphilic lipid under a (polarizing) microscope. More precisely, such temperature may be determined in accordance with a conventional technique involving the preparation of a phase diagram (e.g., Laughlin, R. G., "The Aqueous Phase Behavior of Surfactants," 1994, Academic Press, London, pp. 106-117).

The cubic liquid crystal composition of the present invention is typically a transparent gel. With the addition of an adequate dispersant to the cubic liquid crystal composition, for example, particles having a volume average particle diameter of 50 nm to 5 μm, and typically, liquid crystal fine particles having a peak volume average particle diameter of about 100 nm to 200 nm, can be prepared.

(3) Production of Cubic Liquid Crystal Composition and Modification and Stabilization of the Liquid Crystal Structure The cubic liquid crystal composition of the present invention can be produced by mixing the amphiphilic lipid according to the present invention and water or an aqueous medium.

When producing the cubic liquid crystal composition, the amphiphilic compound having an isoprenoid-type hydrophobic chain represented by formula (1) (hereafter, it may be abbreviated as the "amphiphilic compound (1)") can be used as the amphiphilic lipid according to the present invention:

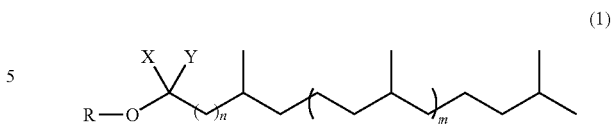

(1)

wherein R represents a hydrophilic group; X and Y each independently represent a hydrogen atom or together form an oxygen atom; n is an integer of 0 to 4; and m is an integer of 0 to 3.

Examples of hydrophilic groups represented by R include residues lacking 1 hydroxyl group selected from among: glycerol (having 2 hydroxyl groups); erythritol, pentaerythritol, threitol, diglycerol, xylose, ribose, arabinose, lyxose, and ascorbic acid (each having 3 hydroxyl groups); and glucose, galactose, mannose, fructose, altrose, gulose, idose, talose, and triglycerol (each having 4 hydroxyl groups). In the formula, represents an oxygen atom.

A person skilled in the art can easily produce such amphiphilic compound (1) via an organic chemical synthesis or biochemical production method well known in the art with reference to the Examples below (e.g., JP Patent Publication (kokai) Nos. 8-245682 A (1996), 2002-226497, 59-170085 A (1984)).

When producing the cubic liquid crystal composition, it is preferable that at least one amphiphilic compound selected from among amphiphilic compounds (1) be used, such compound forming bicontinuous type II cubic liquid crystals and having an IV/OV value of 0.65 to 0.95 (more preferably 0.65 to 0.93) that would likely to lower the Krafft temperature. The expression "IV/OV value" used in the present description is determined as a proportion (IV/OV) of an inorganic value (IV) to an organic value (OV) in an organic compound (an amphiphilic compound in the present invention). Such IV/OV value is used as an indicator for the correlation between physical properties and the chemical structure of an organic compound.

The methods for calculating IV and OV of the IV/OV value used in the present invention are briefly described below. At the outset, OV (an organic value or an organic property value) is determined by multiplying the total number of carbons in the amphiphilic compound by 20 and, when a linear chain is branched, subtracting 10 per branch. IV (an inorganic value or an inorganic property value) is determined by designating the number of hydroxyl groups to be 100, ether oxygen to be 20 (75 in the case of ether oxygen of cyclic sugar, in particular), ester groups to be 60, and nonaromatic monocyclic structures to be 10 in the amphiphilic compound and adding values of all the corresponding groups in the amphiphilic compound. The IV/OV value is known to approximately establish the following relationship with the HLB value that is often used in the surfactant field: HLB=(IV/OV)×10. OV, IV, and IV/OV values are described in detail in: for example, Fujita, A., "Prediction of Organic Compounds by a Conceptional Diagram," Chem. Pharm. Bull., Tokyo, 2, 163-173, 1954; "Formulation Design with Organic Conception Diagram" Nihon Emulsion Co., LTD., 2001, such literature being available from http://www.nihon-emulsion.co.jp/pdf/ocdbook_e.pdf; "Organic conceptual diagram—Bases and Applications—," 1984, Yoshio Kouda, Sankyo Shuppan); or Hanqing Wu, "Chemical Property Calculation through JavaScript and Applications in QSAR" Molecules, 1999, 4, pp. 16-27, such literature being available from http://fr.mdpi.net/molecules/papers/40100016.pdf.

The IV/OV values in a range (0.65 to 0.95) preferable in the present invention are determined by dividing the IV values by the OV values determined by the method of Nihon Emulsion Co., LTD that is applied to phenomenon involving amphiphilic lipids such as surfactants and rounding the obtained values to two decimal places, particularly based on the method of Fujita described above.

When producing the cubic liquid crystal composition of the present invention, at least one amphiphilic compound (1) having Krafft temperature ($T_K$) lower than 6° C. be preferably used.

Specific examples of amphiphilic compounds (1) having IV/OV values between 0.65 and 0.95 or Krafft temperatures lower than 6° C. include compounds represented by formulae (2) to (12) and (15).

When producing the cubic liquid crystal composition of the present invention, an amphiphilic compound (1), preferably an amphiphilic compound (1) having an IV/OV value between 0.65 and 0.95 or a Krafft temperature lower than 6° C., may be used alone or in combinations of two or more. Also, at least one amphiphilic lipid other than the above-mentioned amphiphilic compound (1) may further be mixed therewith.

When 2 or more types of amphiphilic lipids are mixed during production of the cubic liquid crystal composition, at least one of the amphiphilic compounds represented by formulae (2) to (12) and (15) is preferably mixed with at least one other amphiphilic lipid (preferably an amphiphilic compound (1)), although substances to be mixed are not particularly limited thereto. An example of an amphiphilic compound represented by formula (1) that is different from the amphiphilic compound represented by any of formulae (2) to (12) and (15) and is suitably mixed therewith is 1-O-(3,7,11, 15-tetramethylhexadecyl)-β-D-xylopyranoside represented by formula (13).

When a cubic liquid crystal composition to be used at a low temperature of about 4° C. is produced, the single use of the amphiphilic compound represented by formula (13) may be preferably avoided from the viewpoint of safety.

Water or an aqueous medium to be mixed with an amphiphilic lipid in order to form cubic liquid crystals is not particularly limited. Examples thereof include: water, such as sterilized water, purified water, distilled water, ion-exchanged water, or ultrapure water; aqueous electrolytic solutions, such as physiological saline, aqueous solutions of sodium chloride, calcium chloride, magnesium chloride, sodium sulfate, potassium sulfate, sodium carbonate, or sodium acetate; buffers, such as phosphate buffer or Tris-HCl buffer; aqueous solutions comprising water-soluble organic matters such as glycerine, ethylene glycol, or ethanol; aqueous solutions comprising sugar molecules such as glucose, sucrose, or maltose; aqueous solutions comprising water-soluble polymers such as polyethylene glycol or polyvinyl alcohol; aqueous solutions comprising surfactants such as octyl glucoside, dodecyl maltoside, or Pluronic (a copolymer of polyethylene glycol/polypropylene glycol/polyethylene glycol); and body fluids such as intracellular fluid, extracellular fluid, lymphatic fluid, spinal fluid, blood, gastric juice, blood serum, saliva, or urine.

A person skilled in the art can easily determine the amount of water or an aqueous medium to be mixed with an amphiphilic lipid based on a phase diagram for each amphiphilic lipid/water system. In general, such amount is preferably 10% by mass or more of the total mass of a mixed system of amphiphilic lipid (including an amphiphilic compound) and water or an aqueous medium (a total mass of a cubic liquid crystal composition).

In order to produce the cubic liquid crystal composition of the present invention, preferably, an amphiphilic lipid be thoroughly mixed with water or an aqueous medium. The

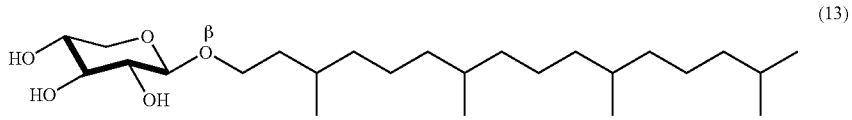

(13)

Examples of amphiphilic lipids suitably mixed with the amphiphilic compound represented by any of formulae (2) to (12) and (15) include monoolein, monovaccenin, 3,7,11,15-tetramethylhexadecyl-1,2,3-triol[phytantriol], and 3,7,11-trimethyldodecane-1,2,3-triol (formula (14) below). When 2 or more amphiphilic lipids are mixed, a person skilled in the art can adequately determine the mixing ratio. The total amount of the amphiphilic compound represented by any of formulae (2) to (12) and (15) is preferably 1% by mass or more, more preferably 5% to 99% by mass, and further preferably 20% to 99% by mass of the total mass of all amphiphilic lipids (including amphiphilic compounds) contained in the mixed system.

When 2 or more amphiphilic lipids are mixed (e.g., when an amphiphilic compound (1) is mixed with an amphiphilic lipid other than the amphiphilic compound (1)), types and concentrations of such amphiphilic lipids are preferably selected so as to bring the Krafft temperature of the amphiphilic lipid mixture to lower than 6° C. In such a case, an amphiphilic compound represented by formula (13) is preferably mixed in as an amphiphilic lipid.

amphiphilic lipid of the present invention is preferably mixed with water or an aqueous medium over the period of, for example, 1 to 50 hours, although the duration of mixing is not limited thereto.

If excess water or an aqueous medium is mixed with the amphiphilic lipid of the present invention, a cubic liquid crystal composition can be produced. The term "excess" used herein refers to an amount of water exceeding the maximal amount of water that can be contained in the cubic liquid crystal structure formed.

When producing the cubic liquid crystal composition of the present invention, the amount of an amphiphilic lipid to be mixed with water or an aqueous medium is not particularly limited, and such amount can be adequately determined depending on the relevant purposes, based on a phase diagram for the amphiphilic lipid-water (or an aqueous medium) system. As described in 1-(2) above, the concentration of amphiphilic lipid at the time of mixing is preferably determined so as to result in formation of a single cubic liquid crystal phase. The thus once produced cubic liquid crystal composition of the present invention may then be diluted with the addition of water or an aqueous medium. Such diluted product is within the scope of the cubic liquid crystal composition of the present invention, as long as such product comprises the cubic liquid crystals of the present invention.

In order to produce the cubic liquid crystal composition of the present invention, while or after the amphiphilic lipid is mixed in water or an aqueous medium, the mixture is preferably heated to a temperature range in which cubic liquid crystals can be formed. The temperature range in which cubic liquid crystals can be formed varies depending on the type or concentration of amphiphilic lipid. A person skilled in the art can determine an adequate temperature range based on the phase diagram for liquid crystals that can be determined for each amphiphilic lipid. In the case of the cubic liquid crystal composition of the present invention, the temperature range in which cubic liquid crystals can be formed is typically relatively extensive (including room temperature) and not particularly limited. In the case of 0.1% to 90% by mass of amphiphilic lipid, for example, the liquid crystal composition can be stably formed if it is mixed at or heated after mixing to generally −10° C. (a subfreezing temperature means one under supercooling conditions under which water is not converted into ice) to 80° C., and preferably 0 to 40° C.

Such method for producing the cubic liquid crystal composition of the present invention is also within the scope of the present invention.

When producing the cubic liquid crystal composition of the present invention, use of two or more types of amphiphilic lipids, preferably two or more types of amphiphilic lipids with different physical properties, can adequately alter the structures or physical properties of the cubic liquid crystals formed. For example, an amphiphilic lipid having a Krafft temperature of 0° C. or lower but poor stability in high-temperature regions can be mixed with two or more types of amphiphilic lipids having high Krafft temperatures to produce a composition that can stably form cubic liquid crystals in a region spanning from low-temperature to high-temperature regions. With the use of two or more types of amphiphilic lipids, diameters of water channels of the cubic liquid crystals formed can also be altered. Further, use of two or more types of amphiphilic lipids can alter the structures or physical properties of the cubic liquid crystals, and the cubic liquid crystal structure can be regulated. That is, properties of the cubic liquid crystal composition (e.g., lattice constant, diameters of water channels of cubic liquid crystals, Krafft temperature, $T_{max}$ value, and viscosity) can be optimized depending on the purpose of use of the cubic liquid crystal composition. For the purpose of the incorporation of a given high-molecular-weight compound into cubic liquid crystals as described below, for example, diameters of water channels of cubic liquid crystals can be increased or decreased depending on the molecular weight of the high-molecular-weight compound to optimize the rate of controlled release.

The cubic liquid crystal composition of the present invention can be produced using amphiphilic lipids arbitrarily selected from among a wide variety of amphiphilic lipids. Thus, the properties or structures of cubic liquid crystals in such composition can be freely regulated.

As an example, a case in which 2 types of amphiphilic lipids forming cubic liquid crystals that belong to a single crystallographic space group are used to regulate the diameters of the water channels of cubic liquid crystals is exemplified below to describe a formula for regulating the cubic liquid crystal structure.

When the diameters of the water channels of cubic liquid crystals formed by an amphiphilic lipid 1 and an amphiphilic lipid 2 to be mixed are respectively determined to be D1 and D2 (D1>D2), a diameter D3 of a water channel of cubic liquid crystals formed by amphiphilic lipids mixed at molar ratios of X1 and X2 (X1+X2=1) is approximately represented by the following equation (i) under conditions in which the concentration of amphiphilic lipid remains constant.

$$D3=(X1*D1+X2*D2) \qquad (i)$$

With the utilization of equation (i), a person skilled in the art can easily design cubic liquid crystals having water channels with diameters of interest.

Further, the present invention also concerns a method for adequately stabilizing a cubic liquid crystal structure concerning the cubic liquid crystal composition of the present invention.

In general, structures of various liquid crystals formed by an amphiphilic lipid/water system are significantly related to the average curvature of the amphiphilic lipid membranes that constitute the liquid crystals. When the average curvature of the amphiphilic lipid membrane convexly curved toward the water side has a positive value and the average curvature of the amphiphilic lipid membrane concavely curved toward the water side has a negative value, the average curvature of the amphiphilic lipid membranes constituting the liquid crystals assumes a negative value with a larger integer, for example, from 0 as the curvature of the lamellar liquid crystals, bicontinuous type II cubic liquid crystals, and type II (inversed) hexagonal liquid crystals, in that order. This indicates that the lamellar liquid crystals or type II (inverted) hexagonal liquid crystals could be transformed into bicontinuous type II cubic liquid crystals, for example, if the average curvature of amphiphilic lipid membranes could be intentionally changed.

The factors that determine the curvatures of the amphiphilic lipid membranes are described in detail in Gruner, S. M. J. Phys. Chem., 93, 7562-757, 1989. An argument such that the liquid crystal structure is determined based on the curvature energy of the amphiphilic lipid membrane and the packing energy of the hydrophobic chain is also developed in Helfrich, W. Z. Naturforsch. 28C, pp. 693-703, 1973; Seddon, J. M.; and Templer, R. H. Phil. Trans. R. Soc. Lond. A, pp. 377-401, 1993, in addition to the above literature.

In the present invention, a substance capable of changing the curvature of the amphiphilic lipid membrane (a curvature-regulating substance) is added to an amphiphilic lipid and the resultant is mixed in water or an aqueous medium. Thus, the liquid crystal structure in the cubic liquid crystal composition can be further stabilized in comparison with the cubic liquid crystal composition composed of the amphiphilic lipid without the addition of the curvature-regulating substance. When the cubic liquid crystal composition of the present invention is found to have been transformed into a lamellar liquid crystal phase under given conditions, for example, an adequate amount of a curvature-regulating substance that alters the curvature toward a negative direction can be added to prevent the transition in liquid crystal phases in the cubic liquid crystal composition of the present invention and stably maintain the cubic liquid crystal structure. Examples of curvature-regulating substances that alter the curvature toward a negative direction include long chain fatty acids such as triglycerides, diglycerides, cholesterol, and nondissociative oleic acid and amphiphilic lipids such as 1,2-dioleoyl-sn-glycero-3-phosphoethanolamine, which form type II (inverted) hexagonal liquid crystals in water. Examples of curvature-regulating substances that can be preferably used in the present invention to alter the curvature toward a negative direction include, but are not limited to, triglyceride-containing substances, such as olive oil, camellia oil, castor oil, and macadamia nut oil, and 1,2-dioleoyl-sn-glycero-3-phosphoethanolamine. When the cubic liquid crystal composition of the present invention is found to have been transformed into a type II (inverted) hexagonal liquid crystal phase under given conditions, however, an adequate amount of a curvature-regulating substance that alters the curvature toward a positive direction can be added to prevent the transition in liquid crystal phases in the cubic liquid crystal composition of the present invention and stably maintain the cubic liquid crystal structure. Examples of curvature-regulating substances that can be preferably used to alter the curvature toward a positive direction include, but are not limited to, lamellar liquid crystals such as egg lecithin, soybean lecithin, digalactosyldiacylglycerol, diglucosyldiacylglycerol, maltosyl phytanyl ether, dialkyl dimethyl ammonium chloride, and polyoxyethylene chain-added phospholipid, potassium oleate, amphiphilic lipids that form type I micelles or type I hexagonal liquid crystals, and surfactants. Amphiphilic lipids (curvature-modifying lipids) that are used as curvature-regulating substances particularly preferably have low melting points (preferably 0° C. or lower). A person skilled in the art can readily determine the optimal amounts of curvature-regulating substances to be added based on a phase diagram for a three-component system of amphiphilic lipid/curvature-regulating substance/water. For example, such curvature-regulating substances are preferably used in amounts of 1% to 50% by mass, and more preferably 3% to 30% by mass, of the total amount of curvature-regulating substances and amphiphilic lipids.

(4) Analysis of Cubic Liquid Crystal Structure

Whether or not the cubic liquid crystal composition of the present invention produced by method (3) forms cubic liquid crystals, is of a bicontinuous type, or is of type II can be examined in the following manner.

(a) Polarizing Microscopic Observation

Figure 2:
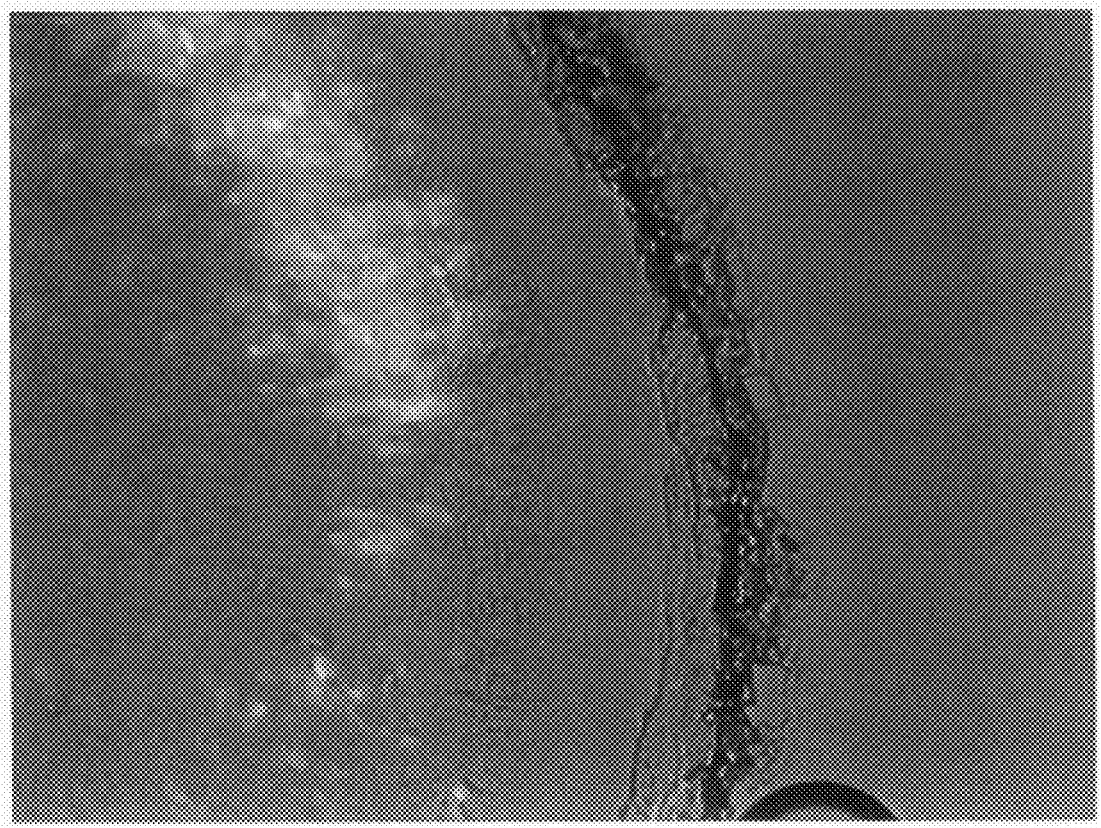
FIG. 2 is a polarizing microscopic photograph showing an amphiphilic compound/water system observed by the penetration method.

Whether or not the amphiphilic lipid/water system forms cubic liquid crystals and whether or not such composition is type I or II can be easily determined by the penetration method. A small amount (several mg) of amphiphilic lipids is placed on a glass slide for a microscope, and slight pressure is applied with a glass cover to form a thin layer of amphiphilic lipids (diameter: about 1 to 5 mm) with a thickness of about 10 μm in the gap between the glass slide and the glass cover. Upon addition of water or an aqueous medium from a side of the gap between the glass slide and the glass cover by capillary action, water gradually invades the amphiphilic lipid thin layer from the exterior edge, and a water content gradient is formed from the amphiphilic lipid thin layer/water interface toward the inside of the amphiphilic lipid thin layer. Polarizing microscopic observation thereof enables the determination of a phase type formed depending on the concentration of the amphiphilic lipid/water system. FIG. 2 shows a polarizing microscopic photograph of the amphiphilic lipid/water system observed by the penetration method. In FIG. 2, 4 regions are observed. The rightmost region in the photograph indicates a water region, and the other regions indicate hydrous amphiphilic lipid regions. In the photograph, the rightmost regions indicates the highest water content and the leftmost region indicates a region of amphiphilic lipids that has not yet been penetrated by water. Adjacent to the water region, a region that imparts the same isotropic texture as the water region (cubic liquid crystals), a region that imparts a bright texture (lamellar liquid crystals), and a region that imparts isotropic texture (dry amphiphilic lipids) are observed. This indicates that the lipid of interest forms cubic liquid crystals. Since cubic liquid crystals are stably formed at the interface of excess water and the amphiphilic lipid portion, such crystals are found to be of type II.

(b) Confirmation of Cubic Liquid Crystals by Small-Angle X-Ray Scattering (SAXS) Assay Cubic liquid crystals exhibit isotropic texture under a polarizing microscope; however, further confirmation is preferably made, in order to conclude that a region exhibiting isotropic texture indicates the presence of cubic liquid crystals. To this end, whether or not the liquid crystal structure has cubic lattices may be investigated by the small-angle x-ray scattering (SAXS) assay. In this process, a sample of an amphiphilic lipid/water system at a given concentration may be introduced into a quartz X-ray capillary tube, the capillary may be sealed with an oxygen burner, and the resultant may be subjected to the SAXS assay.

The cubic liquid crystal composition of the present invention is not particularly limited. Typically, cubic liquid crystals that belong to the crystallographic space group Ia3d (hereafter referred to as "Ia3d cubic liquid crystals"), cubic liquid crystals that belong to the crystallographic space group Pn3m (hereafter referred to as "Pn3m cubic liquid crystals"), or cubic liquid crystals that belong to the crystallographic space group Im3m (hereafter referred to as "Im3m cubic liquid crystals") are formed. Ia3d cubic liquid crystals can be determined by applying spacing exhibiting the following ratio: $\sqrt{3}$:$\sqrt{4}$:$\sqrt{7}$:$\sqrt{8}$:$\sqrt{10}$:$\sqrt{11}$: ... Pn3m cubic liquid crystals can be determined by applying spacing exhibiting the following ratio: $\sqrt{2}$:$\sqrt{3}$:$\sqrt{4}$:$\sqrt{6}$:$\sqrt{8}$:$\sqrt{9}$:$\sqrt{10}$ ... Im3m cubic liquid crystals can be determined by applying spacing exhibiting the following ratio: $\sqrt{2}$:$\sqrt{4}$:$\sqrt{6}$:$\sqrt{8}$:$\sqrt{10}$:$\sqrt{12}$:$\sqrt{14}$ .... In accordance with a method well known in the art, the peak values are determined based on the data exhibiting small angle X-ray scattering data, and the ratio of the reciprocals thereof is determined. Thus, spaces and lattice constants can be easily determined. The peak values of small angle X-ray scattering or the cubic lattice size of cubic liquid crystals in the presence of an excess aqueous solvent are at constant levels regardless of the lipid concentration. The coexistence state of cubic liquid crystals and an excess aqueous medium can be confirmed by the SAXS assay. Thus, whether or not the cubic liquid crystals are of type II can be easily determined.

(c) Confirmation of "Bicontinuous Type"

The curved surface in contact with a terminal methyl group of a hydrophobic chain of the curved amphiphilic lipid bilayer that forms the bicontinuous cubic liquid crystal structure is known to be represented by a curved surface referred to as an infinite periodic minimal surface (IPMS) (Hyde, S. T.; Andersson, S.; Ericsson, B.; Larsson K. Z. Kristallogr., 1984, 168, pp. 213-219., Longley, W.; McIntosh, T. J. Nature, 1983, 303, pp. 612-614). For example, the amphiphilic lipid bilayer of the Ia3d cubic liquid crystals is satisfactorily described by a curved surface referred to as a gyroid surface, and the amphiphilic lipid bilayer of the Pn3m cubic liquid crystals is satisfactorily described by a curved surface referred to as a diamond surface. According to this model, the volume fraction $\phi_{hc}$ of a hydrophobic portion of the amphiphilic lipid molecule in the cubic liquid crystals is represented by the following equation (ii):

$$\phi_{hc} = 2\varpi\left(\frac{d_{hc}}{a_c}\right) + \frac{4}{3}\pi\chi_E^\mu\left(\frac{d_{hc}}{a_c}\right)^3 \tag{ii}$$

wherein ω represents a dimensionless constant determined based on the shape of the curved surface, which is 3.091 in the case of a gyroid surface and 1.919 in the case of a diamond surface; $d_{hc}$ represents the length of the hydrophobic portion of the amphiphilic lipid bilayer; and $a_c$ represents a cubic liquid crystal lattice constant. $\chi^u{}_E$ is Euler's constant, which is −8 in the case of a gyroid surface and −2 in the case of a diamond surface (Anderson, D. M.; Gruner, S. M.; Leibler, S. Proc. Natl. Acad. Sci. U.S.A., 1988, 85, 5364-5368).

The $\phi_{hc}$ can be determined by the following equation (iii).

$$\phi_{hc} = \frac{n_L\left(\frac{M_{hc}}{\rho_{hc}}\right)}{n_L\left(\frac{M_{hc}}{\rho_{hc}} + \frac{M_{head}}{\rho_{head}}\right) + n_W\left(\frac{M_W}{\rho_W}\right)} \quad \text{(iii)}$$

wherein, $M_{hc}$ represents a molecular weight of the hydrophobic chain portion of the amphiphilic lipid molecule; $M_{head}$ represents the molecular weight of a hydrophilic group portion of the amphiphilic lipid molecule; $M_w$ represents the molecular weight of water; $n_L$ and $n_W$ each independently represent the molar number of amphiphilic lipid and of water in the cubic liquid crystals; and $\rho_w$, $\rho_{hc}$, and $\rho_{head}$ each independently represent the density of water, of a hydrophobic chain portion of amphiphilic lipid, and of a hydrophilic group portion of amphiphilic lipids. $\rho_{hc}$ was presumed to be a value equivalent to the density of alcohol (in the case of an amphiphilic lipid of an ether type) or carboxylic acid (in the case of an amphiphilic lipid of an ester type) corresponding to the hydrophobic chain portion of the amphiphilic lipid measured with a densimeter.

In equations, $n_L$ and $n_W$ are actually measurable, and $a_c$ can be measured by the SAXS experiment. Thus, the $d_{hc}$ value can be determined based on equations (ii) and (iii). If the cubic liquid crystals are of a bicontinuous structure, the determined $d_{hc}$ value is equal to the thickness of the hydrophobic group portion of the amphiphilic lipid bilayer of the lamellar liquid crystals composed of the same amphiphilic lipid. Based on such comparison, whether or not the cubic liquid crystal structure is of a bicontinuous type can be determined.

2. Production of a Complex of a Cubic Liquid Crystal Composition and a Drug and Application of Such Composition as a Drug Delivery Carrier The cubic liquid crystal composition of the present invention can comprise various drugs (e.g., biologically or physiologically active substances) embedded in the cubic liquid crystals thereof. The cubic liquid crystal composition of the present invention can comprise water-soluble drugs in the water channel of the cubic liquid crystal structure thereof and hydrophobic drugs such as membrane proteins or hardly soluble drugs in the amphiphilic lipid bilayer portion. The liquid crystal structure of the cubic liquid crystal composition of the present invention is considerably strong, and drugs incorporated in the structure can be satisfactorily protected from the external environment from the physical point of view. In this description, the cubic liquid crystal composition of the present invention comprising drugs embedded therein, and preferably the cubic liquid crystal composition of the present invention comprising drugs embedded in the cubic liquid crystal structure, are referred to as complexes of cubic liquid crystal compositions and drugs. The cubic liquid crystal composition of the present invention and a complex of the cubic liquid crystal composition and a drug can be easily shaped into various forms such as fine particles, thin fibers, or thin layers, in addition to bulk liquid crystals. The cubic liquid crystal composition of the present invention can incorporate and retain drugs in the liquid crystal structure while maintaining functions, activity, structure, or other properties of the drugs in an aqueous environment (e.g., in vivo environment). Such a drug may be a high-molecular-weight compound or low-molecular-weight compound. Also, such a drug may be a physiologically active substance that can be used as, for example, a pharmaceutical product, quasi-drug, or active cosmetic ingredient. It should be noted that the term "drug" used herein does not include a lysosomal enzyme. The term "lysosomal enzyme" used herein refers to a normal enzyme (a wild-type or variant enzyme having functions or activity) that causes a lysosomal disease that can be used for the enzyme replacement therapy for a patient with the lysosomal disease.

In the present invention, the fact that the cubic liquid crystal composition of the present invention can incorporate and retain a high-molecular-weight compound in the liquid crystal structure while maintaining the functions, activity, structure, and other conditions thereof is an advantage of the cubic liquid crystal composition.

The molecular weight of the high-molecular-weight compound that can be embedded as a drug in the cubic liquid crystal composition of the present invention is not particularly limited, and it is generally 4,000 to 1,000,000, and preferably 5,000 to 500,000. Such high-molecular-weight compound may be hydrophilic, hydrophobic, or amphiphilic, it may be an organic or inorganic compound, and it may be naturally occurring, a derivative thereof, or a synthetic product thereof. Such high-molecular-weight compound is not particularly limited. Examples thereof include nanocolloidal particles of proteins (polypeptides) such as enzymes, glycoproteins, lipoproteins, and membrane proteins, nucleic acids (DNA, RNA), polysaccharides, natural rubber, high-molecular-weight sulfur, high-molecular-weight silicon, silica, titania, alumina, hydroxyapatite, and a nylon/polyester/polyacrylate/polymethacrylate/polyvinyl compound. By preparing a complex by allowing the cubic liquid crystal composition to comprise a high-molecular-weight compound to be embedded therein, such high-molecular-weight compound can be retained at high concentration while maintaining functions and activity at high levels for long periods of time.

Examples of the drugs that are used in the present invention include physiologically active substances that can be used as pharmaceutical products, quasi-drugs, or active cosmetic ingredients having molecular weights of about 200 to 4,000. Specific examples thereof include, but are not particularly limited to, naturally occurring or synthetic vitamins, peptides, hormones, and various hardly soluble drugs.

"Embedding" of a target substance (or drug) in the cubic liquid crystal composition of the present invention refers to the conditions in which the target substance (or drug) is present in the cubic liquid crystal structure of the composition and is retained therein for at least a given period of time. In the cubic liquid crystal composition of the present invention, a water-soluble substance is selectively present in a hydrophilic portion (in the water channel containing a polar group of amphiphilic lipid) of the cubic liquid crystals and a hydrophobic substance is selectively present in a hydrophobic portion (a bilayer portion of amphiphilic lipid) of the cubic liquid crystals, in general. Amphiphilic substances such as proteins are optionally present both in hydrophilic and hydrophobic regions of the cubic liquid crystals. The target substance (or drug) may be present in the cubic liquid crystal structure in the form of a monomer or multimer. The target substance (or drug) may be present in the form of, for example, monomolecules, assemblies, fine particles, microcrystals, crystals, or aggregates. The site, shape, and other conditions of each substance (or drug) are not limited thereto.

When the drug to be embedded via the method for producing the cubic liquid crystal composition described above is soluble in water, the complex of the cubic liquid crystal composition of the present invention and a drug can be produced by mixing the drug dissolved in water or an aqueous medium with amphiphilic lipids or directly adding the drug to the previously produced cubic liquid crystal composition. The complex of the present invention can also be produced by mixing a drug dissolved in water or an aqueous medium with the previously produced cubic liquid crystal composition. When the drug to be embedded is hydrophobic (e.g., a hydrophobic physiologically active substance), the complex of the present invention can be produced by mixing a mixture of a hydrophobic drug (e.g., the aforementioned physiologically active substance) and an amphiphilic lipid (such mixture can be easily obtained by dissolving the hydrophobic drug and the amphiphilic lipid in a solvent common among ethanol, acetone, and the like and then removing the solvent) with water or an aqueous medium.

The amount of the drug to be embedded at the time of production of the complex of the present invention is not particularly limited. For example, such drug may be mixed with an amphiphilic lipid in an amount of 0.01% to 50% by mass thereof.

The complex comprising a drug embedded in the cubic liquid crystal composition is capable of controlled release of the drug at a given concentration from the liquid crystal structure over a relatively long period of time. Thus, the cubic liquid crystal composition of the present invention can be effectively used as a drug delivery carrier for a drug delivery system (DDS). For example, a complex comprising the cubic liquid crystal composition of the present invention and the drug embedded therein is produced and the resulting complex is implanted into a given body tissue. This enables concentrated administration of the drug to the tissue. Injection of such complex of the present invention into a body enables the controlled drug release throughout the body over a long period of time.

The method for obtaining the drug to be embedded in the cubic liquid crystal composition is not particularly limited in the present invention. For example, a commercially available product may be purchased, or such substance can be adequately obtained by sampling or purifying the same from a natural origin. Alternatively, it may be produced via a genetic engineering technique. When a high-polymer-weight compound such as a protein is used as a drug to be embedded in the cubic liquid crystal composition of the present invention, such compound is preferably added in such a manner that the functions, activity, and/or structure thereof are maintained in an aqueous solution. When a membrane protein is used as a high-molecular-weight compound, for example, a solubilized membrane protein solution may be mixed with the amphiphilic lipid or the previously prepared cubic liquid crystal composition according to the present invention. Alternatively, a cell having a high-molecular-weight compound expressed on the membrane thereof may be disrupted under mild conditions such as hypoosmotic conditions, and cell membrane fragments may be mixed with an amphiphilic lipid and water or an aqueous medium.

3. Pharmaceutical Composition Using Cubic Liquid Crystal Composition

The complex comprising the cubic liquid crystal composition of the present invention and a drug (e.g., a biologically active substance) embedded therein obtained by the aforementioned method may be optionally mixed with a pharmaceutically acceptable carrier, additive, diluent, or the like to obtain a pharmaceutical composition.

Such drug may be hydrophobic, hydrophilic, or amphiphilic. Specific examples of such drug preferably include, but are not limited to, sodium hyaluronate, immunoglobulin, superoxide dismutase, chlorophyll, diastase, glucoseoxidase, urease, uricase, nucleic acid (e.g., DNA, RNA, siRNA, aptamer, decoy DNA, antisense DNA, or ribozyme), L-asparaginase, adenosine deaminase, Alteplase, angiotensin II (human type), insulin, interferon α, interferon β, interferon γ, urokinase, epoetin α, epoetin β, kallidinogenase, carperitide, L-carnitine, dried concentrated human antithrombin III, desmopressin acetate, tetracosactide acetate, nafarelin acetate, buserelin acetate, leuprorelin acetate, goserelin acetate, celmoleukin (IL-2), somatotropin, chisokinase, teceleukin (IL-2), trafermin (FGF), nasaruplase, nartograstim (G-CSF), neocarzinostatin, batroxobin, pamiteplase, filgrastim (G-CSF), mirimostim (M-CSF), mecasermin, monteplase, lenograstim (G-CSF), an activated prothrombin complex, a dried concentrate of human antihemophilic factor, antihemophilic factor, plasma thromboplastin component, immunoglobulin G, human menopausal gonadotrophin (HMG), serum gonadotropin (PMS), human chorionic gonadotropin (HCG), vasopressin, oxitocin, calcitonin, elcatonin, streptokinase, streptodornase, semialkaline proteinase, serrapeptase, pepsin, lysozyme, glucagon, bromelin, pronase, elastase, thrombin, α2-macroglobulin, apolipoprotein E, arginase, catalase, chymotrypsin, chymopapain, trypsin, tryptophanase, thrombopoietin (TPO), thrombomodulin, hyaluronidase, hirudin, phenylalanine ammonia-lyase, hemoglobin, peroxidase, motilin, lactoferrin, lipase, transforming growth factor (TGF-β), tumor necrosis factor (TNF-α), basic fibroblast growth factor (bFGF), and various antibody drugs. Lysosomal enzymes are not within the scope of the aforementioned drugs.

The cubic liquid crystal composition of the present invention can comprise hardly soluble drugs embedded in, for example, fine particles in the form of microcrystals. Use of the cubic liquid crystal composition of the present invention, accordingly, enables the production of a drug preparation comprising hardly soluble drugs stably solubilized in water.

Examples of hardly soluble drugs that can be used in the present invention include various drugs, such as analgesics, antiinflammatory drugs, antiparasitic drugs, antiarrhythmic drugs, antibiotics, anticoagulant drugs, antidepressant drugs, antidiabetic drugs, antiepileptic drugs, antihistamine drugs, hypotensive drugs, antimuscarinic drugs, antimycobacterial drugs, antitumor drugs, immunosuppressive drugs, antithyroid drugs, antiviral drugs, anxiety-alleviating sedative drugs, astringents, β-adrenergic-receptor blocking drugs, cardiac inotropic drugs, contrast media, corticosteroid, antitussive drugs, diagnostic drugs, diagnostic imaging agents, diuretic drugs, dopaminergic drugs, hemostatic drugs, lipid regulators, muscle relaxers, parasympathetic drugs, thyroid calcitonin and biphosphonate, prostaglandin, radioisotope drugs, sex hormones, antiallergic drugs, stimulants, anorexiants, sympathetic agents, thyroid drugs, vasodilator drugs, and xanthine drugs.

Specific examples of hardly soluble drugs include fluticasone propionate, beclomethasone propionate, budesonide, ciclesonide, paclitaxel, adriamycin, doxorubicin, cisplatin, tetracycline, doxycycline, minocycline, demethylchlortetracycline, metronidazole, danazol, palmitoyl rhizoxin, pencromedine, retinoic acid, isotretinoin, tamoxifen, etoposide, Campotesin, Navelbine, valproic acid, tacrolimus, sirolimus (rapamycin), cyclosporin A, clarithromycin, testosterone, estradiol, progesterone, ciprofloxacin, fenofibrate, benzafibrate, azithromycin, itraconazole, miconazole, propofol, brimonidine, latanoprost, acridine, ajmaline, amobarbital, chlordiazepoxide, chlormadinone acetate, clonazepam, diazepam, diltiazem, kitasamycin, dicumarol, sulfathiazole, medazepam, menadione, midecamycin, piroxicam, nystatin, phenacetin, phenobarbital, phenothiazine, flunitrazepam, predonisolone, nicergoline, phenyloin, probucol, nifedipine, reserpine, furosemide, glibenclamide, indomethacin, griseofulvin, nitrazepam, albendazole, carbamazepine, phenylbutazone, N-methyl-N-(4,6-dimethylpyrodo-2-yl-1-[2-(4-(3,4-dimethoxybenzoyl) piperazin-1-yl)ethyl]-benzimidazole-2-carboxyamide (N-5159), griseofulvin, glibenclamide and nifedipine, cefaclor, cefpodoxime proxetil, cefotiam hexetil, cefuroxime axetil, cefditoren pivoxil, cefcapene pivoxil hydrochloride, cefteram pivoxil, erythromycin, clarithromycin, enoxacin, tosufloxacin tosilate, norfloxacin, piromidic acid, ofloxacin, ketoprofen, diclofenac sodium, flufenamic acid, ketophenylbutazone, ibuprofen, ketoprofen, flurbiprofen, felbinac, acetaminophen, diphenhydramine, promethazine hydrochloride, noscapine, clobutinol hydrochloride, oxeladin tannate, berberine chloride, papaverine hydrochloride, chlorpromazine hydrochloride, carbamazepine, sodium valproate, nicardipine, vinpocetine, etafenone hydrochloride, diltiazem, buformine hydrochloride, cimetidine, naclobisin hydrochloride, mefenamic acid, flufenamic acid, digitoxin, diokitoxin, aminophylline, ursodesoxycholic acid, chenodeoxycholic acid, dinoprostone, minaprine hydrochloride, alfacalcidol, calcitriol, loxistatin, bifonazole, ketoconazole, and lanoconazole.

Examples of pharmaceutically acceptable carriers, diluents, and/or additives that can be incorporated include water, collagen, polyvinyl alcohol, polyvinylpyrrolidone, carboxyvinyl polymer, sodium alginate, water-soluble dextran, sodium carboxymethyl starch, pectin, xanthan gum, gum arabic, casein, gelatin, agar, glycerine, propylene glycol, polyethylene glycol, vaseline, paraffin, stearyl alcohol, stearic acid, human serum albumin, mannitol, sorbitol, and lactose. Such carriers, additives, and diluents are adequately selected depending on dosage forms.

The pharmaceutical composition of the present invention can be administered orally or parenterally. Oral dosage forms of the pharmaceutical composition of the present invention are not limited, and examples thereof include capsules, gels, liquids, suspensions, and syrups. Parenteral dosage forms of the pharmaceutical composition of the present invention are not limited, and examples thereof include liquids such as those of hypodermic injections, intramuscular injections, intravenous injections, and transfusions, patches such as wet compresses and transdermal tape preparations, topical creams such as ointments, suppositories, nasal drops, and mouthwashes, and implant preparations such as hypodermic or interstitial implants.

The pharmaceutical composition of the present invention may incorporate binders, excipients, lubricants, disintegrators, wetting agents, stabilizers, buffers, corrigents, preservatives, aroma chemicals, colorants, or the like that are commonly used for pharmaceutical preparations.

A dose of the pharmaceutical composition of the present invention may be determined depending on the age, body weight, symptoms, route of administration, frequency of administration, or other conditions relating to the target of administration, based on the content of a drug as an active ingredient. A person skilled in the art can determine or change such conditions in accordance with conventional techniques. An example is, but is not particularly limited to, administration of 0.05 to 1 g of the pharmaceutical composition of the present invention as an implant preparation. The targets of administration of the pharmaceutical composition of the present invention are primarily mammalian animals including humans, livestock animals, pet animals, and experimental (test) animals. The present invention also relates to a method for treating mammalian animals comprising administering the pharmaceutical composition of the present invention.

Upon administration of the pharmaceutical composition of the present invention, a drug as an active ingredient exhibits its functions while being retained within the cubic liquid crystal structure. When such drug is an enzyme, for example, such enzyme can react with a substrate in the cubic liquid crystal structure. When a drug retained in the cubic liquid crystal structure is a water-soluble protein, it is present selectively in a water channel portion in the cubic liquid crystal. Since the diameter of the water channel is several nm and is close to a molecular size, structural denaturation can be prevented by the space-limiting effects of the channel wall. Also, such drug is less susceptible to actions of degrading enzymes or cells under an in vivo environment, and thus, such drug can stably maintain its activity for a long period of time. Since the pharmaceutical composition of the present invention can retain drugs at a highly concentrated state in the cubic liquid crystal structure, small quantities of drugs exhibit high activity levels. Further, the pharmaceutical composition of the present invention allows gradual controlled release of the drugs incorporated in its cubic liquid crystal structure to the outside of the composition, and it can be used as a controlled-release preparation. Thus, the pharmaceutical composition of the present invention can be effectively used in order to administer a drug the concentration of which is not preferably rapidly increased in the blood. With the use of the pharmaceutical composition of the present invention, sufficient amounts of drugs can be administered at relatively low frequencies to a patient who requires the administration of a given dose of a drug over a long period of time, a patient who is afflicted with genetic or chronic disease, or a patient who requires continuous drug administration for disease prevention, for example. Accordingly, the pharmaceutical composition of the present invention is very useful from the viewpoint of improvement in the quality of life of patients or the families thereof. Specifically, the present invention relates to a method for controlled release of a drug (e.g., a physiologically active substance) by administering the pharmaceutical composition of the present invention to a subject in vivo, in vitro, or ex vivo.

The pharmaceutical composition of the present invention employs, as a drug delivery carrier, a liquid crystal composition composed of highly biocompatible amphiphilic lipid molecules. Accordingly, side effects imposed on the patient to which the drug has been administered are considered to be insignificant.

The applications of the pharmaceutical composition of the present invention include active ingredients of quasi-drugs such as therapeutic dentifrice toothpastes, antihidrotic sprays, medicated creams, baby powders, hair-growth drugs, hair dyes, bath agents, medicated cosmetics, and medicated soaps or functional foods, as well as pharmaceutical products.

4. Cosmetic Composition Utilizing Cubic Liquid Crystal Composition

The present invention also relates to a cosmetic composition comprising a cubic liquid crystal composition. Preferably, the cosmetic composition of the present invention comprises a complex of the cubic liquid crystal composition of the present invention and an active cosmetic ingredient.

Such complex to be incorporated into the cosmetic composition of the present invention can be prepared in accordance with the procedure described in section 2. above.

The aforementioned active cosmetic ingredient is not particularly limited as long as such active ingredient can be used for a cosmetic product. It may be a hydrophobic, hydrophilic, or amphiphilic ingredient. Examples of active cosmetic ingredients include, but are not limited to: moisturizers such as collagen, milk protein, hyaluronic acid, sodium hyaluronate, ceramide, atelocollagen, and polyethylene glycol; skin-whitening agents such as vitamin C and derivatives thereof, arbutin, kojic acid, orizanol, and lucinol; antiaging agents such as vitamin A, retinoic acid, silibin, superoxide dismutase, and chlorophyll; ultraviolet absorbers such as para-aminobenzoic acid and phenyl salicylate; anti-inflammatory agents such as hydrocortisone acetate and glycyrrhetinic acid; and DNA, pantothenyl ethyl ether, vegetable oil, algae extract, amino acids and derivatives thereof, vitamin E and a derivative thereof, $TiO_2$, octyl methoxycinnate, p-aminobenzoic acid ester, glycyrrhizinate, and trichlorocarbanilide (TCC). It should be noted that a lysosomal enzyme is not within the scope of the above active cosmetic ingredient.

The cosmetic composition of the present invention can comprise additives such as carriers, diluents, and excipients that are commonly incorporated into cosmetic products. Examples of such additives include, but are not limited to, an amino acid or a derivative thereof, oil (e.g., a higher alcohol such as lauryl alcohol, a higher fatty acid such as stearic acid, animal oil and fat such as mink oil, and vegetable oil such as coconut oil), an emulsifier (e.g., fatty acid salt such as sodium lauryl sulfate and a nonionic surfactant such as glyceryl monostearate), an antioxidant (e.g., tocopherol and ascorbic acid), a chelating agent (e.g., edetate and sodium oxalate), a pH regulator (e.g., ethanolamine and citric acid), a preservative (e.g., paraben and phenol), a thickener (e.g., carboxyvinyl polymer and bentonite), an alcohol (e.g., a lower alcohol such as ethanol and a polyhydric alcohol such as 1,3-butylene glycol), an astringent (e.g., tartaric acid and tannic acid), a vitamin preparation (e.g., vitamin B family, vitamin C, and vitamin E), an aroma chemical (e.g., linalol and essential oil), a pigment (e.g., an inorganic pigment such as titanium dioxide and a natural pigment such as cochineal), and water (e.g., sterilized water and ion-exchange water).

The usage patterns for the cosmetic composition of the present invention are not particularly limited as long as such composition is in the form of a common cosmetic product, and a liquid, gel, or cream form is more preferable. Specific examples thereof include: cosmetic products for the face such as a skin water, an essence, an emulsion, a cream, a lotion, a lip balm, a facial mask, a makeup base, a foundation, and a lipstick; and cosmetic products for the body such as a sunscreen, a sunburn cream, a body lotion, a body cream, a hand cream, a slimming agent, and an antihidrotic agent. The cosmetic composition of the present invention can be blended in and prepared in accordance with a common technique for producing a cosmetic product. A person skilled in the art can adequately determine the amount of a complex of a cubic liquid crystal composition and an active cosmetic ingredient to be incorporated into a cosmetic composition by taking the effective amount of the active ingredient or the shape of the cosmetic product to be used into consideration. Common techniques for formulating and preparing cosmetic products are described in detail in, for example, Mitsui et al. (ed.), "New Cosmetic Science," 2nd ed., 2001, Nanzando; Takeo Mitsui, "New Cosmetic Science," 1998, Elsevier Science B. V.; or Fragrance Journal (ed.), "Manufacturing of cosmetic products—Techniques and Reality," 2001, Fragrance Journal (ed.).

5. Crystallization of Protein Using Cubic Liquid Crystal Composition

The cubic liquid crystal composition of the present invention is useful for crystallizing various proteins. In the present invention, a target protein is embedded in the cubic liquid crystal composition of the present invention in accordance with the method for producing a complex of a cubic liquid crystal composition and a drug described in section 2 above, and the resultant is then incubated under adequate conditions to allow the protein crystal to grow in the resulting complex. Thus, a target protein can be crystallized with sufficiently large size and high quality.

Such effects of promoting crystallization are considered to probably result from the conditions advantageous for crystallization realized by the "effects of stabilizing" proteins embedded in a water channel having a size equivalent to the protein size (Zhou, H-X., Dill, K. A., Biochemistry, 2001, 11289-11293) or the "effects of concentration" whereby the effective concentration of a protein becomes greater than the protein concentration of a bulk solution (Tanaka, S., Egelhaaf, S. U., Poon, W. C. K., Phys. Rev. Lett., 2004, 92, 128102-1) in the cubic liquid crystals composed of a lipid bilayer similar to a biomembrane and a water channel, provided that the protein to be embedded is a water-soluble protein. A membrane protein that becomes unstable upon removal from the biomembrane is stabilized when it is incorporated into the lipid bilayer portion of the cubic liquid crystal that provides an environment similar to a biomembrane. Thus, protein denaturation during the crystallization over the period of several weeks to several months is considered to be inhibited. Water-soluble impurities that often impede protein crystallization in the case of conventional crystallization in an aqueous solution remain in the water channel in the cubic liquid crystal and do not affect crystallization of the membrane protein that proceeds in the lipid bilayer portion. Such "purification effects" or influences caused by thermal convection or mechanical vibration in the solution, which are problematic in the conventional crystallization in a solution, are significantly inhibited in the cubic liquid crystals, and this is considered to be advantageous for protein crystallization. It should be noted that the technical scope of the present invention is not limited to such logic.

Proteins, and particularly, target proteins for drug discovery, are actively studied by subjecting proteins alone and protein-ligand conjugates to crystallization and to X-ray structural analysis, in order to obtain structural information that is critical for drug discovery. With conventional techniques for crystallization, however, satisfactory protein crystals have hardly every been formed that can yield satisfactory resolution via X-ray structural analysis, particularly in the case of membrane proteins and the like. In recent years, examples of crystallization of membrane proteins using cubic liquid crystals of monoacylglycerol featuring monoolein have been reported ("Methods and Results in Crystallization of Membrane Proteins," 2003, Ed., So Iwata, International University Line, La Jolla, Chapters 3 and 4). Since the Krafft temperature of such monoacylglycerol is higher than 4° C., crystallization primarily occurs at room temperature (e.g., at 20° C.). Accordingly, monoacylglycerol could not be applied to many proteins that are preferably crystallized at 4° C. or lower. In contrast, use of the cubic liquid crystal composition of the present invention having a Krafft temperature lower than 6° C., and particularly, 0° C. or lower, enables protein crystallization at 4° C. or lower.

A method for protein crystallization utilizing the cubic liquid crystal composition of the present invention enables satisfactory crystallization of membrane proteins as well as water-soluble proteins. Types of proteins that can be crystallized by this method are not particularly limited.

Target proteins that can be crystallized by such method include not only typical proteins, i.e., polypeptides comprising 100 or more amino acid residues, but also shorter polypeptides (e.g., short polypeptides comprising 10 to 50 amino acid residues and medium polypeptides comprising 50 to 100 amino acid residues) and oligopeptides (e.g., oligopeptides comprising 2 to 10 amino acid residues). Target proteins to be crystallized may be monomeric or multimeric. A preferable example of a target protein to be crystallized is an enzyme. Such enzyme may be, for example, an assembly comprising an enzyme molecule comprising a single polypeptide chain, an enzyme subunit, or a plurality of enzyme subunits or a substance comprising other components such as a metal ion or an organic low-molecular-weight compound (coenzyme). Further, the target proteins of crystallization may be antibodies (immunoglobulins), membrane proteins, or conjugate proteins such as nucleoproteins, glycoproteins, lipoproteins, or phosphoproteins. Examples of membrane proteins include membrane receptor proteins, ion channels, and transcription factors. In particular, cytochrome P-450 (e.g., CYP1A2, CYP2E1, CYP2C19, CYP2C9, CYP2D6, and CYP3A4), various G proteins, G protein-coupled receptors, various transcription factors (e.g., NF-κB), and the like can be targets of drug discovery that are useful from the viewpoint of pharmaceutical development. Thus, such membrane proteins are particularly useful as the targets of protein crystallization. When membrane proteins are crystallized by the method of the present invention, membrane proteins isolated from cells are solubilized with an adequate surfactant, and the resulting aqueous solution of membrane proteins may be embedded in amphiphilic lipids by the method described in sections 1-(2) and 2 above.

In one embodiment, an aqueous solution of target proteins (or an aqueous solution of solubilized membrane proteins) is mixed with amphiphilic lipids in a PCR tube (or a glass tube having a diameter of about 1 to 3 mm) to form cubic liquid crystals comprising proteins embedded therein. In such a case, the proportion of the aqueous solution of proteins to amphiphilic lipid by mass is preferably selected in a manner that allows formation of a single phase of cubic liquid crystals. This is because a two-phase sample comprising cubic liquid crystals and an excess amount of aqueous solution of proteins becomes clouded, which disadvantageously complicates observation of crystal growth behavior that proceeds with respect to the cubic liquid crystals or crystalline morphology. After the formation of cubic liquid crystals, it is preferable that a crystallization agent be added to promote crystallization. The term "crystallization agent" used herein refers to a compound that is commonly used for reinforcing attractive interaction among protein molecules and for accelerating crystallization. A crystallization agent is not particularly limited. Examples thereof include electrolytes such as ammonium sulfate, lithium sulfate, magnesium sulfate, ammonium phosphate, sodium phosphate, potassium phosphate, sodium chloride, magnesium chloride, and sodium citrate, water-soluble polymers such as polyethylene glycol, and organic compounds such as isopropanol and 2-methyl-2,4-pentanediol. These compounds are generally used as aqueous solutions comprising the same. Also, a commercialized crystallization kit can be used. In general, a crystallization agent is added after the formation of the cubic liquid crystal composition comprising proteins embedded therein. Alternatively, an aqueous protein solution comprising a crystallization agent may be mixed with amphiphilic lipid when preparing a cubic liquid crystal composition comprising proteins embedded therein. According to a general technique, a cubic liquid crystal composition comprising a crystallization agent maintains a sealed PCR tube, the PCR tube is allowed to stand in an incubator at an adequate temperature (e.g., 4° C. or 20° C.), and crystals are allowed to grow over a period of several weeks to several months. During such period, the process of crystal growth or crystalline morphology is observed under an optical microscope (polarizing), and crystals are allowed to grow until they reach X-ray assayable sizes. In the crystallization method of the present invention, 0.05 μl to 0.2 μl of a solution of the cubic liquid crystal composition comprising proteins embedded therein is used instead of a protein solution, and crystallization can be carried out via conventional crystallization techniques such as vapor diffusion (the sitting-drop method or hanging-drop method). Protein crystallization is precisely discussed in Noriyoshi Sakabe and Shigeo Aibara (ed.), "Crystallization of protein," Kyoto University Press, 2005. Once protein crystals have been obtained, crystals can be recovered from the cubic liquid crystals and then subjected to a common x-ray assay technique in accordance with a conventional technique (Drenth, J., "Principles of Protein X-ray Crystallography," 1994, Springer-Verlag, New York). Crystals can be sampled by a method of mechanically sampling crystals with the use of a microtool for crystal manipulation that is used for common protein crystallization experiments, or a method whereby a small amount of an aqueous surfactant solution such as octyl glucoside is added to transform cubic liquid crystals into lamellar liquid crystals or the like, viscosity of a lipid matrix is lowered, and the crystals are then sampled by a cryoloop technique.

In such a crystallization method, the amphiphilic compounds of the present invention constituting the cubic liquid crystal compositions are as described above, and use of at least one compound represented by formulae (2) to (13) and (15) or combinations of two or more thereof is particularly preferable. As described above, these amphiphilic compounds may be used in combination with other amphiphilic lipids.

In the method for protein crystallization of the present invention, a protein to be crystallized is preferably added at a concentration of 1 mg/ml to 10 mg/ml or higher in the process of generating a complex of a cubic liquid crystal composition, although the concentration is not limited to such level.

In the method for protein crystallization of the present invention, 4 kDa to 1,000 kDa and preferably 9 kDa to 500 kDa of proteins (a molecular weight as an assembly in the case of a multimer) can be preferably crystallized, although the quantity is not limited thereto. The method for protein crystallization of the present invention is particularly suitable for crystallizing a protein having a molecular weight of 20 kDa or greater, more preferably of 100 kDa or greater, and further preferably of 400 kDa or greater. The method for protein crystallization of the present invention is particularly effective for protein crystallization at low temperatures of 4° C. or lower, in addition to conventional crystallization at room temperature (20° C.), when crystallization of a membrane protein, which is still difficult to perform, is intended.

EXAMPLES

Hereafter, the present invention is described in greater detail with reference to the following examples, although the technical scope of the present invention is not limited thereto.

Example 1

Synthesis of Amphiphilic Compounds

Synthesis of 1-O-(3,7,11-trimethyldodecyl)erythritol [formula (2)]

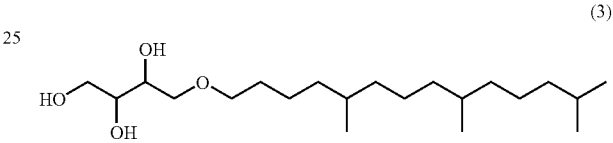

(2)

Under a nitrogen atmosphere, a solution of 22.8 g (100 mmol) of 3,7,11-trimethyldodecanol and 9.48 g (120 mmol) of pyridine in 200 ml of dry methylene chloride was added dropwise to a solution of 20.96 g (110 mmol) of p-toluenesulfonyl chloride in 100 ml of dry methylene chloride under ice cooling (1 to 2° C.). After the dropwise addition, the resultant was agitated at room temperature overnight, the resulting reaction solution was successively washed with 200 ml of water, 200 ml of 2N hydrochloric acid, and 200 ml of a saturated sodium bicarbonate water, and was dried over anhydrous magnesium sulfate. After the filtration, the resultant was concentrated to obtain 41.6 g of crude 3,7,11-trimethyldodecyl tosylate.

Under a nitrogen atmosphere, 16.0 g (131 mmol) of erythritol was dissolved in 400 ml of dry DMF. Under ice cooling (2 to 4° C.), to the resulting solution, a suspension of 2.62 g of 50 to 70% NaH (65.5 mmol NaH in the case of 60%) after removal of oil components with hexane in about 50 ml of DMF was added in several batches. After the addition, the resultant was agitated for 1 hour at room temperature, and then heated to about 50° C. 13.1 g (34 mmol) of crude 3,7,11-trimethyldodecyl tosylate obtained above was added dropwise thereto, the fraction adhered to the apparatus was washed down with 55 ml of DMF, and the resultant was heated to 80° C., followed by agitation for 4 hours. The resulting reaction solution was concentrated, and 300 ml of dichloromethane and 1,000 ml of saturated saline were added to the residue, and then the organic phase was separated. The residual aqueous phase was subjected to extraction with 150 ml of dichloromethane. 500 ml of the resulting organic phase in total was washed twice with 300 ml of saturated saline, and dried over anhydrous magnesium sulfate. After the filtration, the resultant was concentrated to obtain 7.7 g of a brown oily substance. The substance was column-purified using 400 g of silica gel ($CH_2Cl_2 \rightarrow CH_2Cl_2$:MeOH (98:2)$\rightarrow CH_2Cl_2$:MeOH (95:5)) to obtain 0.66 g of 1-O-(3,7,11-trimethyldodecyl)erythritol. The HPLC purity was 100.0%. Also, the results of NMR analysis are as shown below.

$^1$H-NMR spectrum: (270 MHz, $CDCl_3$, TMS), δ: 0.83-0.9 (m, 12H), 1.0-1.7 (m, 17H), 2.31 (br. s, 1H), 2.65 (br. s, 1H), 2.77 (br. s, 1H), 3.5-3.7 (m, 4H), 3.7-3.9 (m, 4H)

Synthesis of 1-O-(5,9,13-trimethyltetradecyl)erythritol [formula (3)]

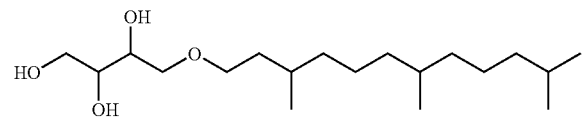

(3)

Under a nitrogen atmosphere, a solution of 27 g (0.11 mol) of 5,9,13-trimethyl-1-tetradecanol and 10 g (0.13 mol) of pyridine in 200 ml of dry methylene chloride was added dropwise to a solution of 22.1 g (0.12 mol) of p-toluenesulfonyl chloride in 100 ml of dry methylene chloride under ice cooling. After the dropwise addition, the mixture was agitated at room temperature overnight, the resulting reaction solution was successively washed with 200 ml of water, 200 ml of 2N hydrochloric acid, and 200 ml of a saturated sodium bicarbonate water, and was dried over anhydrous magnesium sulfate. After the filtration, the resultant was concentrated under reduced pressure to obtain 34.4 g of (5,9,13-trimethyltetradecyl)tosylate. Under a nitrogen gas stream, 25.8 g (0.21 mol) of erythritol was dissolved in 200 ml of dry DMF, and 4.2 g (0.11 mol) of 60% NaH was added in several batches under ice cooling. After the addition, the resultant was agitated at room temperature for 1 hour, and then was heated to 50° C. A half amount of (5,9,13-trimethyltetradecyl)tosylate obtained above (17.2 g) was added dropwise thereto, and was washed with 55 ml of DMF. The resultant was heated to 80° C. and then agitated for 4 hours, the resulting reaction solution was concentrated under reduced pressure, 500 ml of ether was added to the residual solution to perform extractive dissolution twice, the product was washed twice with saturated saline, and then it was dried over anhydrous magnesium sulfate. After the filtration, the resultant was concentrated, and purified by silica gel column chromatography to obtain 2.3 g of 1-O-(5,9,13-trimethyltetradecyl)erythritol having the following properties. As a result of HPLC analysis of the obtained product, the purity of 1-O-(5,9,13-trimethyltetradecyl)erythritol was 76.9% and that of 2-O-(5,9,13-trimethyltetradecyl)erythritol was 23.1%. The results of NMR analysis are as shown below.

$^1$H-NMR spectrum: (270 MHz, $CDCl_3$, TMS), δ: 0.845, 0.867 (d, J=6.9 Hz, 6.6 Hz, 12H), 1.0-1.6 (m, 21H), 3.51 (t, J=7.5 Hz, 2H), 3.55-3.85 (m, 6H)

Synthesis of 1-O-(3,7,11,15-tetramethylhexade-canoyl)erythritol [1-O-(phytanoyl)erythritol; formula (4)]

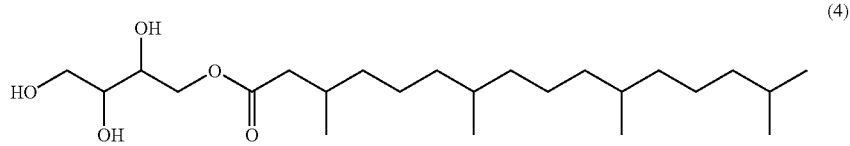

(4)

Under a nitrogen atmosphere, one drop of pyridine was added to 2.5 g of phytanic acid and 12.5 ml of methylene chloride, and 1.43 g of thionyl chloride was added dropwise thereto at room temperature. After the completion of dropwise addition, the resultant was refluxed for 1 hour, and concentrated under reduced pressure to obtain about 2.6 g of phytanic acid chloride.

Under a nitrogen atmosphere, 1.33 g of erythritol, 1.15 g of pyridine, and 40 ml of dry N,N-dimethylformamide were mixed and dissolved with heating. The resultant was cooled to room temperature, a solution of 2.40 g of phytanic acid chloride obtained above in 7 ml of methylene chloride was added dropwise thereto, and the mixture was then agitated at room temperature for 1 hour. 100 ml of Methylene chloride was added thereto, and the resultant was washed with 300 ml of saturated saline and then twice with 200 ml of saturated saline, followed by drying over anhydrous sodium sulfate. Following filtration and concentration under reduced pressure, the resultant was purified by silica gel column chromatography to obtain 1.4 g of transparent and semisolid 1-O-(3,7,11,15-tetramethylhexadecanoyl)erythritol. As a result of HPLC analysis using acetonitrile:water (4:1) as a carrier solvent and CAPCELL PAK SG-120 (5 μm) as a column, it was found in the obtained product that the purity of 1-O-(3,7,11, 15-tetramethylhexadecanoyl)erythritol was 91.1% and that of 2-O-(3,7,11,15-tetramethylhexadecanoyl)erythritol was 8.5%. The results of NMR analysis are as shown below.

$^1$H-NMR spectrum: (270 MHz, CDCl$_3$, TMS), δ: 0.8-0.9 (m, 12H), 0.93 (d, J=6 Hz, 3H), 1.0-1.6 (m, 22H), 1.95 (br. s, 1H), 2.13 (dd, J=14 Hz, 9 Hz, 1H), 2.37 (dd, J=14 Hz, 6 Hz, 1H), 3.33 (br. s, 1H), 3.43 (br. s, 1H), 3.58-3.92 (m, 4H), 4.27 (d, J=5 Hz, 1H)

Synthesis of mono-O-(3,7,11,15-tetramethylhexade-cyl)pentaerythritol [mono-O-(phytanyl)pentaerythritol; formula (5)]

Under a nitrogen atmosphere, 29.16 g (97.67 mmol) of phytanol and 9.27 g (117.2 mmol) of pyridine were dissolved in 220 ml of dry methylene chloride, and 20.48 g (107.4 mmol) of p-toluenesulfonyl chloride was added little by little under ice cooling, in order to prevent the liquid temperature from exceeding 10° C. After the completion of addition, agitation was continued for 12 hours until phytanol disappeared, the resulting reaction solution was successively washed with 200 ml of water, 200 ml of 2N hydrochloric acid, and 200 ml of a saturated sodium bicarbonate water, and dried over anhydrous magnesium sulfate. After the filtration, the resultant was concentrated under reduced pressure to obtain 61.31 g of phytanyl tosylate.

Under a nitrogen gas stream, 36.09 g (265.1 mmol) of pentaerythritol was dissolved in 210 ml of dry DMF, and 5.3 g (132.5 mmol) of 60% NaH was added little by little under ice cooling. The resultant was heated to room temperature and agitated for 1 hour, and 30.0 g (66.26 mmol) of phytanyl tosylate was added dropwise thereto, followed by washing with 55 ml of DMF. The resultant was heated to 80° C. and agitated for 4 hours, the resulting reaction solution was concentrated under reduced pressure, 500 ml of ether was added to the residual solution to perform extractive dissolution twice, the product was washed twice with saturated saline, and then it was dried over anhydrous magnesium sulfate. After the filtration, the resultant was concentrated, purified by silica gel column chromatography to obtain 6.3 g of mono-O-(3,7,11,15-tetramethylhexadecyl)pentaerythritol, which was in colorless, transparent, and somewhat viscous liquid form. The purity of the product determined by HPLC analysis was not lower than 99.5%. The results of NMR analysis are as shown below.

$^1$H-NMR spectrum: (270 MHz, CDCl$_3$, TMS), δ: 0.8-1.7 (m, 39H), 2.68 (br. s, 3H), 3.44 (br, 4H), 3.69 (br. s, 6H)

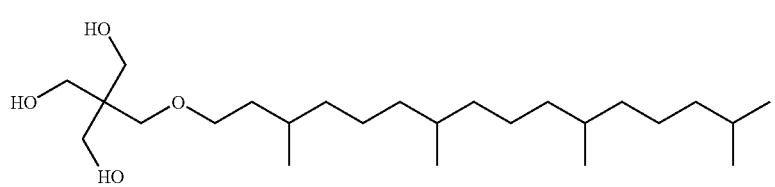

(5)

Synthesis of mono-O-(3,7,11,15-tetramethylhexadecanoyl)pentaerythritol [mono-O-(phytanoyl)pentaerythritol: formula (6)]

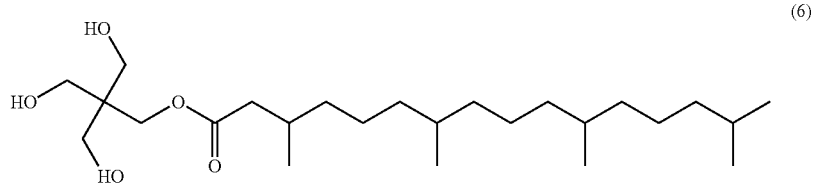

(6)

Under a nitrogen atmosphere, one drop of pyridine was added to 2.0 g of phytanic acid and 10 ml of methylene chloride, and 1.14 g of thionyl chloride was added dropwise at room temperature. After the completion of dropwise addition, the mixture was refluxed for 1 hour, and then concentrated under reduced pressure to obtain about 2 g of phytanic acid chloride.

Pentaerythritol (0.88 g), 0.69 g of pyridine, and 25 ml of dry 1,3-dimethyl-2-imidazolidinone were mixed and dissolved with heating. The resultant was cooled to room temperature, a solution of 1.32 g of phytanic acid chloride obtained above in 5 ml of methylene chloride was added dropwise thereto, and the mixture was then agitated at room temperature for 1 hour. 100 ml of Methylene chloride was added to the resulting reaction solution, the mixture was washed 5 times with 100 ml of saturated saline, and it was dried over anhydrous sodium sulfate, followed by filtration and concentration under reduced pressure. After the remaining dimethylimidazolidinone had been removed, the concentrated solution was purified by silica gel column chromatography to obtain 0.64 g of transparent and semisolid mono-O-(3,7,11,15-tetramethylhexadecanoyl)pentaerythritol. The purity of the product determined by HPLC analysis was 99.4%. The results of NMR analysis are as shown below.

$^1$H-NMR spectrum: (270 MHz, CDCl$_3$, TMS), δ: 0.7-0.9 (m, 12H), 0.95 (d, J=7 Hz, 3H), 1.0-1.6 (m, 22H), 1.9 (br. s, 1H), 2.15 (dd, J=14 Hz, 9 Hz), 2.38 (dd, J=14 Hz, 7 Hz, 1H), 3.17 (br. s, 2H), 3.62 (s, 6H), 4.16 (s, 2H)

Synthesis of
1-O-(5,9,13,17-tetramethyloctadecanoyl)erythritol
[formula (7)]

Under a nitrogen atmosphere, one drop of pyridine was added to 10 g of 5,9,13,17-tetramethyloctadecanoic acid and 20 ml of methylene chloride, and 5.2 g of thionyl chloride was added dropwise thereto at room temperature. After the completion of dropwise addition, the mixture was refluxed for 1 hour and concentrated under reduced pressure to obtain 10.5 g of 5,9,13,17-tetramethyloctadecanoic acid chloride.

2.56 g of Erythritol, 2.21 g of pyridine, and 70 ml of dry DMF were mixed and dissolved with heating. The product was cooled to room temperature, a solution of 5 g of 5,9,13,17-tetramethyloctadecanoic acid chloride obtained above in 10 ml of methylene chloride was added dropwise thereto, and the mixture was then agitated at room temperature for 1 hour. 100 ml of Methylene chloride was added to the resulting reaction solution, and the mixture was washed 3 times with saturated saline, and it was dried over anhydrous sodium sulfate. Following filtration and concentration under reduced pressure, the concentrate was purified by silica gel column chromatography to obtain 2.83 g of transparent and semisolid 1-O-(5,9,13,17-tetramethyloctadecanoyl)erythritol. As a result of HPLC analysis of the obtained product, the purity of 1-O-(5,9,13,17-tetramethyloctadecanoyl)erythritol was 91.6% and that of 2-O-(5,9,13,17-tetramethyloctadecanoyl)erythritol was 8.4%. The results of NMR analysis are as shown below.

$^1$H-NMR spectrum: (270 MHz, CDCl$_3$, TMS), δ: 0.8-0.9 (m, 15H), 1.0-1.7 (m, 26H), 2.11 (br. s, 1H), 2.33 (t, J=7.9 Hz, 2H), 2.66 (br. s, 1H), 2.75 (br. s, 1H), 3.6-3.9 (m, 4H), 4.29-4.36 (m, 2H)

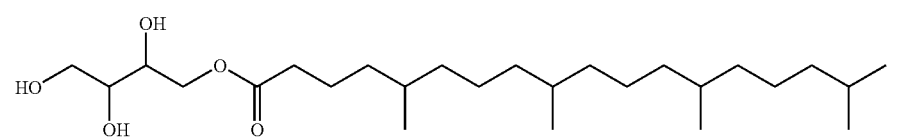

(7)

Synthesis of mono-O-(5,9,13,17-tetramethyloctade-cyl)pentaerythritol [formula (8)]

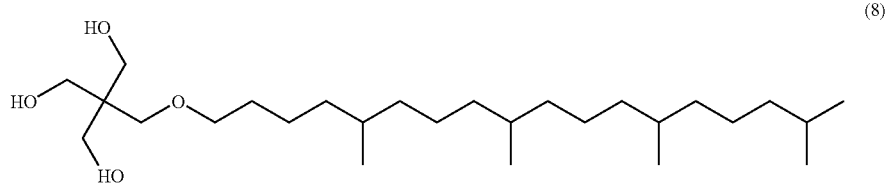

(8)

Under a nitrogen atmosphere, a solution of 30 g (0.09 mol) of 5,9,13,17-tetramethyl-1-octadecanol and 8.72 g (0.11 mol) of pyridine in 200 ml of dry methylene chloride was added dropwise to a solution of 19.3 g (0.10 mol) of p-toluenesulfonyl chloride in 100 ml of dry methylene chloride under ice cooling. After the dropwise addition, the mixture was agitated at room temperature overnight, the resulting reaction solution was successively washed with 200 ml of water, 200 ml of 2N hydrochloric acid, and 200 ml of a saturated sodium bicarbonate water, and it was dried over anhydrous magnesium sulfate. After the filtration, the resultant was concentrated under reduced pressure to obtain 42 g of (5,9,13,17-tetramethyloctadecyl)tosylate.

Under a nitrogen gas stream, 25 g (0.18 mol) of pentaerythritol was dissolved in 200 ml of dry DMF, and 3.7 g (0.09 mol) of 60% NaH was added in several batches under ice cooling. After the addition, the mixture was agitated at room temperature for 1 hour, and heated to 50° C., and a half amount of (5,9,13,17-tetramethyloctadecyl)tosylate obtained above (21 g) was added dropwise thereto, followed by washing with 55 ml of DMF. The resultant was heated to 80° C. and then agitated for 4 hours, the resulting reaction solution was concentrated under reduced pressure, 500 ml of ether was added to the residual solution to perform extractive dissolution twice, the resultant was washed twice with saturated saline, and it was dried over anhydrous magnesium sulfate. After the filtration, the resultant was concentrated, and purified by silica gel column chromatography to obtain 7.3 g of mono-O-(5,9,13,17-tetramethyloctadecyl)pentaerythritol, which was in transparent and viscous liquid form. The purity determined by HPLC analysis was not lower than 99.5%. The results of NMR analysis are as shown below.

$^1$H-NMR spectrum: (270 MHz, CDCl$_3$, TMS), δ: 0.83-0.88 (m, 15H), 1.0-1.6 (m, 28H), 2.88 (br. s, 3H), 3.39-3.52 (m, 4H), 3.71 (d, J=3.9 Hz, 6H)

Synthesis of mono-O-(5,9,13,17-tetramethyloctadecanoyl)pentaerythritol [formula (9)]

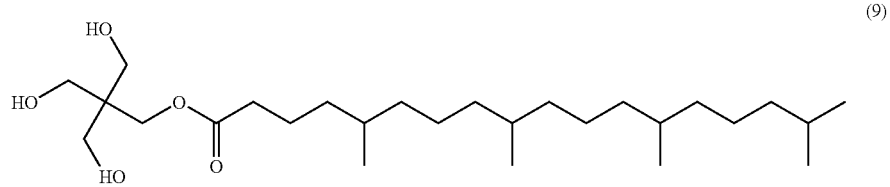

(9)

Pentaerythritol (3.81 g), 2.21 g of pyridine, and 120 ml of dry DMF were mixed and dissolved with heating. The product was cooled to room temperature, the solution of 5 g of 5,9,13,17-tetramethyloctadecanoic acid chloride obtained in the step of synthesis of 1-O-(5,9,13,17-tetramethyloctadecanoyl)erythritol [formula (7)] in 5 ml of methylene chloride was added dropwise thereto, and the mixture was then agitated at room temperature for 1 hour. 100 ml of Methylene chloride was added to the resulting reaction solution, the mixture was washed 3 times with saturated saline, and dried over anhydrous sodium sulfate. Following filtration and concentration under reduced pressure, the concentrate was purified by silica gel column chromatography to obtain 2.50 g of mono-O-(5,9,13,17-tetramethyloctadecanoyl)pentaerythritol having the following properties. The purity determined by HPLC analysis was not lower than 99.5%. The results of NMR analysis are as shown below.

$^1$H-NMR spectrum: (270 MHz, CDCl$_3$, TMS), δ: 0.8-0.9 (m, 15H), 1.0-1.7 (m, 26H), 2.34 (t, J=7.4 Hz, 2H), 3.06 (br. s, 3H), 3.63 (d, J=4 Hz, 6H), 4.17 (s, 2H)

Synthesis of 1-O-(5,9,13,17-tetramethyloctadecyl)-β-D-xylopyranoside [abbr.: β-XylC22; formula (10)]

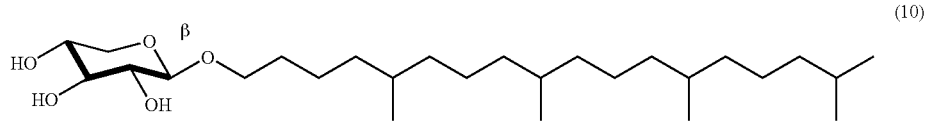

(10)

1) Under an argon atmosphere, 318 mg of β-xylose tetraacetate was dissolved in 6 ml of dry methylene chloride, and the solution was cooled to 0° C. A solution of 0.12 ml of tin tetrachloride dissolved in 1 ml of methylene chloride was added dropwise thereto, the mixture was agitated at room temperature for 20 minutes, and then cooled to −10° C. A solution of 326.6 mg of 5,9,13,17-tetramethyloctadecanol in 1 ml of methylene chloride was added dropwise thereto, and the mixture was agitated for 4 hours. A sodium bicarbonate water was added to the reaction solution and extraction was carried out 3 times with methylene chloride. The extract was washed with water and dried over anhydrous sodium sulfate. After the filtration, the resultant was concentrated, and the concentrate was purified by column chromatography to obtain 93 mg of 1-O-(5,9,13,17-tetramethyloctadecyl)-β-D-xylopyranoside triacetate.

2) Under an argon atmosphere, 584.8 mg of 1-O-(5,9,13,17-tetramethyloctadecyl)-β-D-xylopyranoside triacetate was dissolved in 5 ml of dry methanol, and 54 mg of sodium methylate was added, followed by agitation. The mixture was agitated at room temperature overnight, the resultant was cooled, and 1 ml of 1N-hydrochloric acid was added dropwise thereto. The reaction solution was concentrated under reduced pressure, the resulting residue was dissolved in chloroform to prepare a slurry solution, and the resultant was purified by silica gel column chromatography to obtain 413 mg of a waxy semisolid, 1-O-(5,9,13,17-tetramethyloctadecyl)-β-D-xylopyranoside. Also, 1-O-(5,9,13,17-tetramethyloctadecyl)-β-D-xylopyranoside was dissolved in a mixed solvent of acetic anhydride-pyridine, the solution was treated at 60° C. for 2 hours, and the purity thereof was determined by gas chromatography. The purity was shown to be 96%. The results of NMR analysis are as shown below.

$^1$H-NMR spectrum: (300 MHz, CDCl$_3$, TMS), δ: 0.84, 0.86 (d, J=6.4 Hz, J=6.8 Hz, 15H), 1.0-1.7 (m, 31H), 3.2-3.7 (m, 5H), 3.82 (dd, J=16 Hz, 7.7 Hz, 1H), 3.94 (dd, J=11.6 Hz, 5 Hz, 1H), 4.25 (d, J=7.1 Hz, 1H)

Synthesis of 1-O-(3,7,11,15-tetramethylhexadecyl)-α-D-xylopyranoside [formula (11)]

Under an argon atmosphere, 5.16 g (17.3 mM) of 3,7,11,15-tetramethylhexadecanol was added to 2 g of dried molecular sieve 4A, the mixture was agitated for 2 hours, 5 g (15.7 mM) of vacuum-dried tetra-O-acetyl-β-D-xyloside in 100 ml of methylene chloride under an argon atmosphere was added thereto, and the resultant was agitated for 10 to 30 minutes. A solution of 1M tin chloride in methylene chloride (15.8 ml) was added dropwise thereto, and the mixture was agitated at room temperature for 20 minutes. Subsequently, the reaction system was cooled to 5° C., a solution of 5.16 g (17.3 mM) of 3,7,11,15-tetramethylhexadecanol in 20 ml of methylene chloride was added dropwise thereto over the period of 30 minutes, and the mixture was continuously agitated in that state at room temperature for 4 hours. The resulting solution was poured into a saturated aqueous solution of sodium bicarbonate, and extraction was carried out 3 times with 100 ml of methylene chloride, followed by washing with water. The organic phase was dried over anhydrous sodium sulfate, filtered, and then concentrated. Subsequently, the mixture was purified by silica gel column chromatography (eluent: a mixed solvent of hexane-ethyl acetate).

The obtained tetraacetate was dissolved in 5.5 ml of methanol, and 2.5 ml of 0.05 M sodium methylate was added thereto. The mixture was agitated at room temperature for 4.5 hours, and the equal amount of 1N hydrochloric acid was added thereto for neutralization. After the solution was concentrated, the concentrate was purified by silica gel column chromatography (eluent: a mixed solvent of chloroform/methanol) and vacuum-dried to obtain a colorless, transparent, and viscous liquid.

The purity of the resulting liquid was determined. The results of elementary analysis concerning C and H were C, 70.1% (estimate: 69.7%) and H, 11.9% (estimate: 11.8%), which were well consistent with the estimate values calculated based on the molecular structures. As a result of NMR

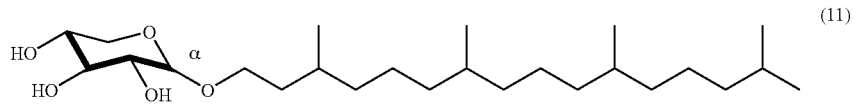

(11)

analysis, it was shown that the purity of the a form was at least 97%, and no signal was observed concerning the βform. The results of NMR analysis are as shown below.

$^1$H-NMR spectrum: (300 MHz, CDCl$_3$, TMS), δ: 4.78 (1H, d, J=3.78 Hz, H1), 4.38 (1H, H5a), 3.83 (1H, H4), 3.09 (1H, d, J=8.9 Hz, H3), 3.7 (2H, H'1), 3.4-3.8 (5H, H2, H5b, 3*OH) s, 1H), 2.68 (br. s, 2H), 3.425 (t, J=6.5 Hz, 2H), 3.47 (s, 2H), 3.72 (s, 6H)

Synthesis of 6-O-(5,9,13,17-tetramethyloctadecanoyl)-L-ascorbic acid [formula (15)]

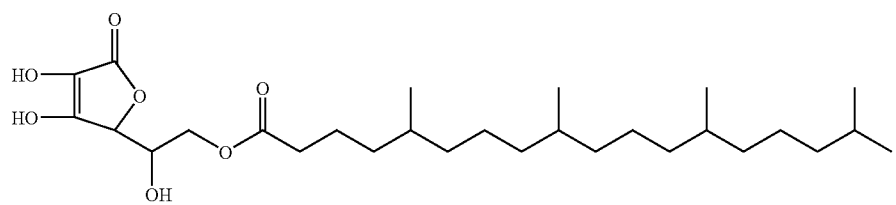

(15)

Synthesis of mono-O-(5,9,13-trimethyltetradecyl)pentaerythritol [formula (12)]

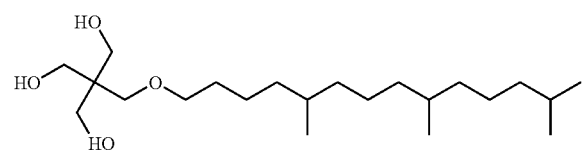

(12)

Under a nitrogen gas stream, 28.7 g (0.21 mol) of pentaerythritol was dissolved in 200 ml of dry DMF, and 4.22 g (0.11 mol) of 60% NaH was added in several batches thereto under ice cooling. After the addition, the mixture was agitated at room temperature for 1 hour, the resultant was heated to 50° C., and a half amount (17.2 g) of (5,9,13-trimethyltetradecyl) tosylate obtained in the step of synthesis of 1-O-(5,9,13-trimethyltetradecyl)erythritol [formula (3)] was added dropwise thereto, followed by washing with 55 ml of DMF. The mixture was heated to 80° C. and then agitated for 4 hours, the resulting reaction solution was concentrated under reduced pressure, 500 ml of ether was added to the residual solution to perform extractive dissolution twice, the product was washed twice with saturated saline, and it was dried over anhydrous magnesium sulfate. After the filtration, the resultant was concentrated, and the concentrate was purified by silica gel column chromatography to obtain 5.8 g of mono-O-(5,9,13-trimethyltetradecyl)pentaerythritol having the following properties.

$^1$H-NMR spectrum: (300 MHz, CDCl$_3$, TMS), δ: 0.846, 0.867 (d, J=6.6 Hz, 6.3 Hz, 12H), 1.0-1.6 (m, 21H), 1.72 (br.

Under an argon gas stream, 21.0 g (119 mmol) of L-ascorbic acid was dissolved in 90 ml of concentrated sulfuric acid. With agitation, 42.3 g (119 mmol) of 5,9,13,17-tetramethyloctadecanoaic acid methyl was added, and the resultant was allowed to stand at 24° C. to 27° C. overnight. The obtained homogenous solution was added to 750 ml of ion-exchanged water, and extraction was carried out with diisopropyl ether, followed by washing with water. The organic phase was dried over anhydrous sodium sulfate and concentrated under reduced pressure.

The concentrated solution was purified by silica gel column chromatography, treated with activated carbon in ethanol, filtered, and concentrated to obtain 9.1 g of light yellow semisolid, 6-O-(5,9,13,17-tetramethyloctadecanoyl)ascorbic acid, having the following NMR spectrum.

$^1$H-NMR spectrum: (300 MHz, DMSO-d$_6$, TMS), δ: 11.1 (br. s, 1H), 8.4 (br. s, 1H), 5.3 (br. s, 1H), 4.67 (s, 1H), 4.06 (m, 2H), 3.97 (m, 1H), 2.3 (m, 2H), 1.6-1.0 (m, 26H), 0.9-0.8 (m, 15H)

Synthesis of 1-O-(3,7,11,15-tetramethylhexadecyl)-α,β-D-xylopyranoside [formula (16)]

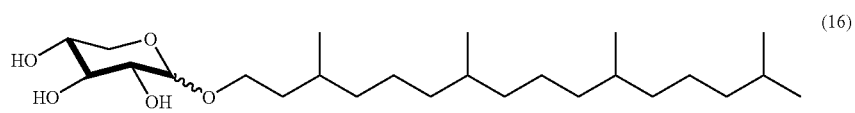

(16)

Phytanol (298 g, 998 mM) was introduced into a flask equipped with a capillary and a distillator, and 30.0 g (200 mM) of D-(+)-xylose ground in a mortar was added thereto. After p-toluenesulfonic acid monohydrate (1.9 g, 10 mM) was added, the pressure was lowered to 40 torr while bubbling an argon gas through the capillary. The flask was gradually heated in an oil bath, and the internal temperature was brought to 95° C. while removing water by distillation. After the reaction was allowed to proceed at 95° C. for 7 hours, the product was cooled to room temperature, and 10 ml of 1N aqueous sodium hydroxide solution was added. The aqueous phase was separated, the organic phase was purified by silica gel column chromatography, and 60.5 g of light brown crude 1-O-(3,7,11,15-tetramethylhexadecyl)-α,β-D-xylopyranoside was obtained. A fraction (59.5 g) thereof was dissolved in a mixture of 1N aqueous sodium hydroxide solution (2.34 ml)

and ethanol (120 ml), 2.34 ml of 30% aqueous hydrogen peroxide solution was added dropwise thereto, and the mixture was agitated at room temperature for 15 hours. The reaction solution was diluted with 1,150 ml of chloroform, and successively washed with 115 ml of distilled water, 115 ml of 40% sodium thiosulfate, and 115 ml of saturated saline, and then dried over anhydrous sodium sulfate, followed by concentration under reduced pressure. The concentrated residue was purified by silica gel column chromatography. As a result, 58.6 g of light yellow crude 1-O-(3,7,11,15-tetramethylhexadecyl)-α,β-D-xylopyranoside was obtained. A fraction (53.6 g) thereof was dissolved in 530 ml of ethanol, 5.3 g of activated carbon was added, and the resultant was agitated at room temperature for 1 hour, followed by filtration and concentration under reduced pressure. The residue was purified by silica gel column chromatography, the concentrates solution was dissolved in 530 ml of ethanol, and the solution was filtered through a membrane filter (PTFE, 0.2 μm), followed by concentration under reduced pressure. Thus, 52.0 g of colorless 1-O-(3,7,11,15-tetramethylhexadecyl)-α,β-D-xylopyranoside was obtained.

The results of NMR analysis of this liquid are shown below. An α-form content was about 66% and a β-form content was about 34%.

$^1$H-NMR spectrum: (300 MHz, CDCl$_3$, TMS), δ: 4.80 (0.66H, d, J=3.6 Hz, H1), 4.35 (0.34H, J=6.3 Hz, H1), 4.35 (1H, dd), 3.3-4.0 (7H, m), 1.0-1.8 (m, 31H), 0.83-0.91 (m, 15H)

Synthesis of mono-O-(5,9,13,17-tetramethyloctadecanoyl)pentaerythritol [formula (9)]-2

Under a nitrogen atmosphere, 115.4 g (846 mmol) of pentaerythritol and 515 ml of dry DMF were introduced into a 2 L-flask and dissolved by heating to 113° C. With the addition of 70 ml of DMF, 93 ml of DMF was removed by distillation for dehydration. 0.82 g of Dry anhydrous potassium carbonate (5.93 mmol, 1.1 mol %) was introduced, and the resultant was refluxed under a reduced pressure of 120 to 140 mmHg at 102° C. to 104° C. 200 g of 5,9,13,17-Tetramethyloctadecanoic acid methyl (564 mmol) was added dropwise thereto over 2.5 hours, and the generated methanol was removed by distillation to allow the reaction to proceed. 0.39 g of anhydrous potassium carbonate (0.5 mol %) was added 1 hour after the dropwise addition, and the reaction was continued for 2 hours. After the rate of conversion is reached 99% or higher, the reaction product was cooled, and 0.781 g (17 mmol) of formic acid was added for neutralization. Under reduced pressure, methanol and DMF were removed by distillation, a reduced pressure condition was cancelled with nitrogen, and 300 ml of isopropyl ether was added and the mixture is cooled to room temperature with agitation. The unreacted pentaerythritol was separated from the mixture by filtration and then washed with 200 ml of isopropyl ether, and 600 ml thereof was added to the resulting filtrate, followed by washing with 400 ml of a saturated sodium bicarbonate water.

900 ml of Isopropyl ether, 400 ml of water, and 200 ml of a saturated sodium bicarbonate water were added to the aqueous phase for separation, and the organic phase was washed with 200 ml of water. The organic phase was combined, 950 ml of isopropyl ether was added, the resultant was washed with 1,000 ml of water and with 600 ml of warm water, and the resulting organic phase was washed with 500 ml of water, followed by dehydration, filtration, and concentration. Thus, 214 g of crude mono-O-(5,9,13,17-tetramethyloctadecanoyl)pentaerythritol having the purity of 48.4% was obtained.

A batch of reaction and post treatment was carried out in the same manner, and 193.4 g of crude mono-O-(5,9,13,17-tetramethyloctadecanoyl)pentaerythritol having the purity of 41.0% was obtained.

The obtained crude mono-O-(5,9,13,17-tetramethyloctadecanoyl)pentaerythritols were combined, 357.8 g thereof was subjected to thin-film distillation (180° C. to 190° C., (9)

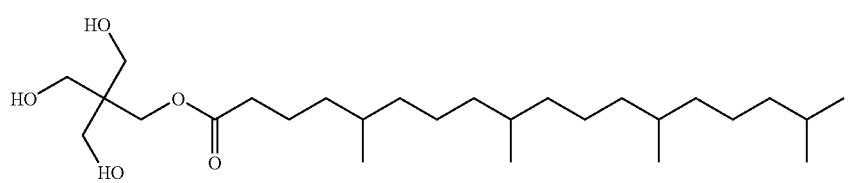

0.004 torr) thereby 111.1 g of mono-O-(5,9,13,17-tetramethyloctadecanoyl)pentaerythritol having the purity of 83 to 89% was obtained.

Reference Example 1

Synthesis of 1-O-(3,7,11,15-tetramethylhexadecyl)-β-D-xylopyranoside [β-XP; formula (13)]

(13)

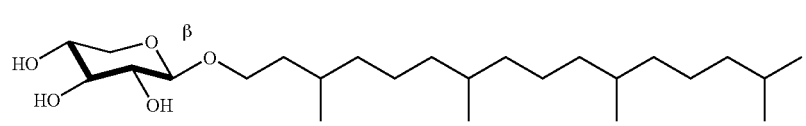

Under an argon atmosphere, 5 g (15.7 mM) of vacuum-dried tetra-O-acetyl-β-D-xylopyranoside and 100 ml of methylene chloride were added to 2 g of dried molecular sieve 4A, and the resultant was agitated for 10 to 30 minutes. The product was cooled to 5° C. to 8° C., 16 ml of a solution of 1M tin chloride in methylene chloride was added dropwise thereto, and the mixture was agitated at room temperature for 20 minutes. After the resultant was cooled to −10° C., 16 ml of a solution of 4.69 g (15.7 mM) of 3,7,11,15-tetramethylhexadecanol in methylene chloride was added dropwise over about 30 minutes, and agitation was continued in that state for 4 hours. The resulting solution was introduced into a saturated aqueous solution of sodium bicarbonate, and extraction was carried out 3 times with 100 ml of methylene chloride, followed by washing with water. The organic phase was dried over anhydrous sodium sulfate, filtrated, and then concentrated. Subsequently, the mixture was purified by silica gel column chromatography (eluent: a mixed solvent of hexane/ethyl acetate).

The resulting 1-O-(3,7,11,15-tetramethylhexadecyl)-β-D-xylopyranoside triacetate was dissolved in 5.5 ml of methanol, and 2.5 ml of 0.05M sodium methylate was added thereto. After the mixture was agitated at room temperature for 4.5 hours, the equal amount of 1N hydrochloric acid was added for neutralization. After the solution was concentrated, the concentrate was purified by silica gel column chromatography (eluent: a mixed solvent of chloroform/methanol), and the resultant was dried under reduced pressure to obtain 1-O-(3,7,11,15-tetramethylhexadecyl)-β-D-xylopyranoside [formula (13)] (a white waxy solid). NMR analysis demonstrated that contamination by 1-O-(3,7,11,15-tetramethylhexadecyl)-α-D-xylopyranoside did not take place.

Example 2

Concerning the amphiphilic compounds that can be particularly preferably used in the present invention, the IV/OV values were determined as shown in the table below. The IV/OV values were calculated down to three places of decimals.

TABLE 1

IV/OV values

| Formula | Amphiphilic compounds | OV values; IV values; IV/OV values |
|---|---|---|
| (2) | 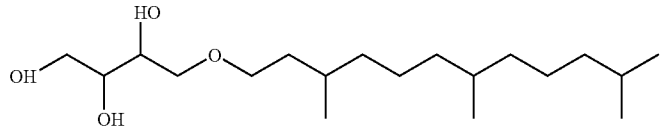<br>1-O-(3,7,11-trimethyldodecyl)erythritol | OV: 380 − 30 = 350<br>IV: 100 × 3 + 20 = 320<br>IV/OV = 0.914 . . . |
| (3) | 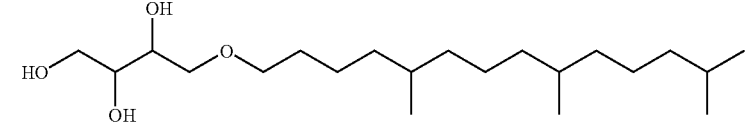<br>1-O-(5,9,13-trimethyltetradecyl)erythritol | OV: 420 − 30 = 390<br>IV: 100 × 3 + 20 = 320<br>IV/OV = 0.820 . . . |
| (4) | 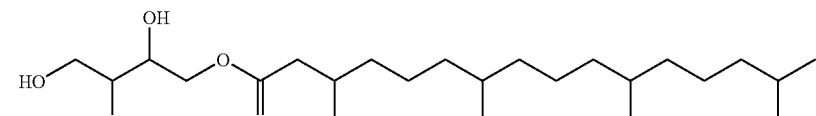<br>1-O-(phytanoyl)erythritol | OV: 480 − 40 = 440<br>IV: 100 × 3 + 60 = 360<br>IV/OV = 0.818 . . . |
| (5) | 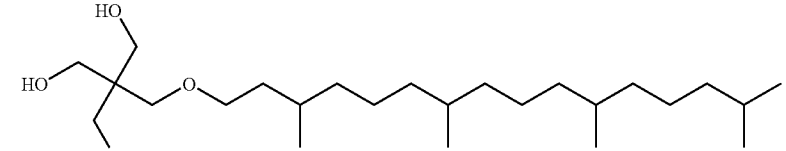<br>Mono-O-(phytanyl)pentaerythritol | OV: 500 − 40 − 20 = 440<br>IV: 100 × 3 + 20 = 320<br>IV/OV = 0.727 . . . |
| (6) | 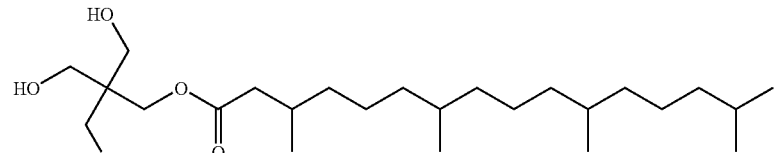<br>Mono-O-(phytanoyl)pentaerythritol | OV: 500 − 40 − 20 = 440<br>IV: 100 × 3 + 60 = 360<br>IV/OV = 0.818 . . . |

TABLE 1-continued

IV/OV values

| Formula | Amphiphilic compounds | OV values; IV values; IV/OV values |
|---|---|---|
| (7) | 1-O-(5,9,13,17-tetramethyloctadecanoyl)erythritol | OV: 520 − 40 = 480<br>IV: 100 × 3 + 60 = 360<br>IV/OV = 0.750 |
| (8) | Mono-O-(5,9,13,17-tetramethyloctadecyl)pentaerythritol | OV: 540 − 40 − 20 = 480<br>IV: 100 × 3 + 20 = 320<br>IV/OV = 0.666... |
| (9) | Mono-O-(5,9,13,17-tetramethyloctadecanoyl)-pentaerythritol | OV: 540 − 40 − 20 = 480<br>IV: 100 × 3 + 60 = 360<br>IV/OV = 0.750 |
| (10) | 1-O-(5,9,13,17-tetramethyloctadecyl)-β-D-xylopyranoside | OV: 540 − 40 = 500<br>IV: 100 × 3 + 75 + 20 + 10 = 405<br>IV/OV = 0.810 |
| (11) | 1-O-(3,7,11,15-tetramethylhexadecyl)-α-D-xylopyranoside | OV: 500 − 40 = 460<br>IV: 100 × 3 + 75 + 20 + 10 = 405<br>IV/OV = 0.880... |
| (12) | Mono-O-(5,9,13-trimethyltetradecyl)pentaerythritol | OV: 440 − 30 − 20 = 390<br>IV: 100 × 3 + 20 = 320<br>IV/OV = 0.820... |
| (15) | 6-O-(5,9,13,17-tetramethyloctadecanoyl)ascorbic acid | OV: 560 − 40 = 520<br>IV: 100 × 3 + 120 + 60 + 2 = 482<br>IV/OV = 0.926... |

The Krafft temperatures of these amphiphilic compounds and mixtures thereof determined by the analyses described below are shown in Table 2-1 and Table 2-2.

TABLE 2-1

Krafft temperature of amphiphilic compound alone

| Formula | Amphiphilic compound | Krafft temperature (° C.) |
| --- | --- | --- |
| (2) | 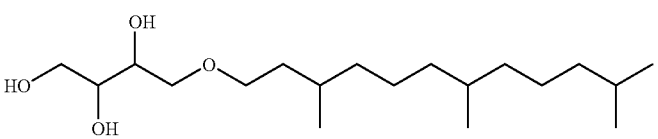  1-O-(3,7,11-trimethyldodecyl)erythritol | 0° C. or lower |
| (3) | 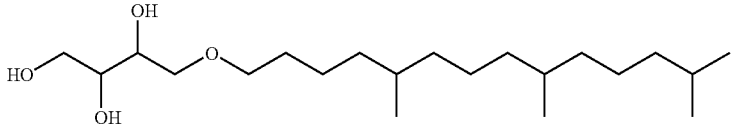  1-O-(5,9,13-trimethyltetradecyl)erythritol | 0° C. or lower |
| (4) | 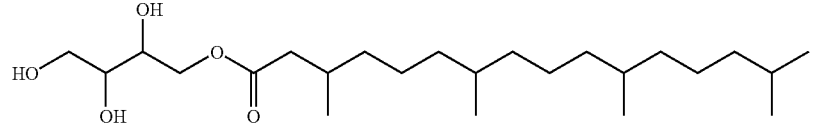  1-O-(phytanoyl)erythritol | 0° C. or lower |
| (5) | 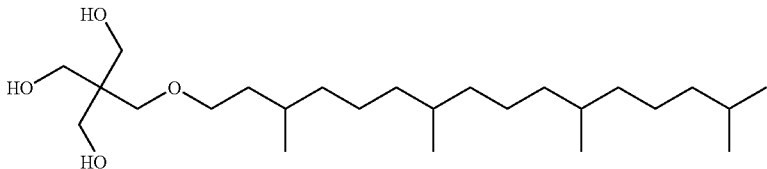  Mono-O-(phytanyl)pentaerythritol | 0° C. or lower |
| (6) | 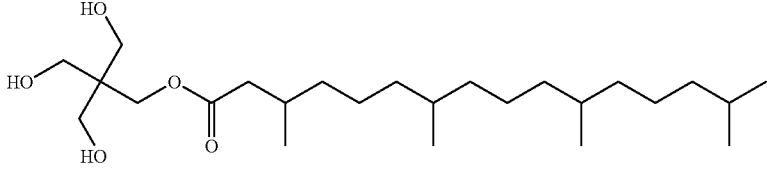  Mono-O-(phytanoyl)pentaerythritol | 0° C. or lower |
| (7) | 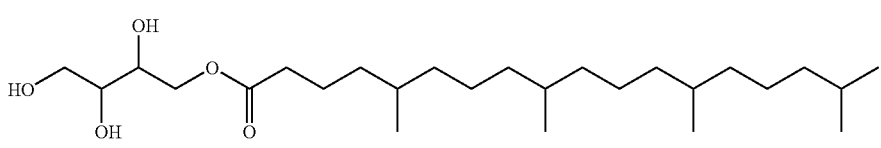  1-O-(5,9,13,17-tetramethyloctadecanoyl)erythritol | 0° C. or lower |

TABLE 2-1-continued

Krafft temperature of amphiphilic compound alone

| Formula | Amphiphilic compound | Krafft temperature (° C.) |
|---|---|---|
| (8) | Mono-O-(5,9,13,17-tetramethyloctadecyl)pentaerythritol | 0° C. or lower |
| (9) | Mono-O-(5,9,13,17-tetramethyloctadecanoyl)-pentaerythritol | 0° C. or lower |
| (10) | 1-O-(5,9,13,17-tetramethyloctadecyl)-β-D-xylopyranoside | 0° C. or lower |
| (11) | 1-O-(3,7,11,15-tetramethylhexadecyl)-α-D-xylopyranoside | 0° C. or lower |
| (12) | Mono-O-(5,9,13-trimethyltetradecyl)pentaerythritol | 0° C. or lower |
| (15) | 6-O-(5,9,13,17-tetramethyloctadecanoyl)-L-ascorbic acid | 0° C. or lower |

TABLE 2-2

Krafft temperatures of mixed lipids

| Formulae | Amphiphilic lipid | Krafft temperature |
|---|---|---|
| (13) + (11) | 1-O-(3,7,11,15-tetramethylhexadecyl)-β-D-xylopyranoside (65%) + 1-O-(3,7,11,15-tetramethylhexadecyl)-α-D-xylopyranoside | 0° C. or lower |

TABLE 2-2-continued

Krafft temperatures of mixed lipids

| Formulae | Amphiphilic lipid | Krafft temperature |
|---|---|---|
| (13) + (5) | 1-O-(3,7,11,15-tetramethylhexadecyl)-β-D-xylopyranoside (20%) + mono-O-(phytanyl)pentaerythritol (80%) | 0° C. or lower |
| (11) + (13) + (14) | 1-O-(3,7,11,15-tetramethylhexadecyl)-D-xylopyranoside (α:β = 5:95) (80%) + 3,7,11-trimethyldodecane-1,2,3-triol (20%) | 0° C. or lower |

Example 3

Formation and Analysis of Type II Cubic Liquid Crystals-1

Mono-O-(3,7,11,15-tetramethylhexadecyl)pentaerythritol (hereafter referred to as "mono-O-(phytanyl)pentaerythritol," formula (5) above) and pure water were introduced into a mixing device, and incubation was carried out while performing 100 or more times of mixing operations at room temperature (23° C.) over the period of 48 hours. Thus, a homogeneously mixed sample of mono-O-(phytanyl)pentaerythritol/water system was obtained. This sample of mono-O-(phytanyl)pentaerythritol/water system appeared to be a transparent gel composition.

Figure 3:
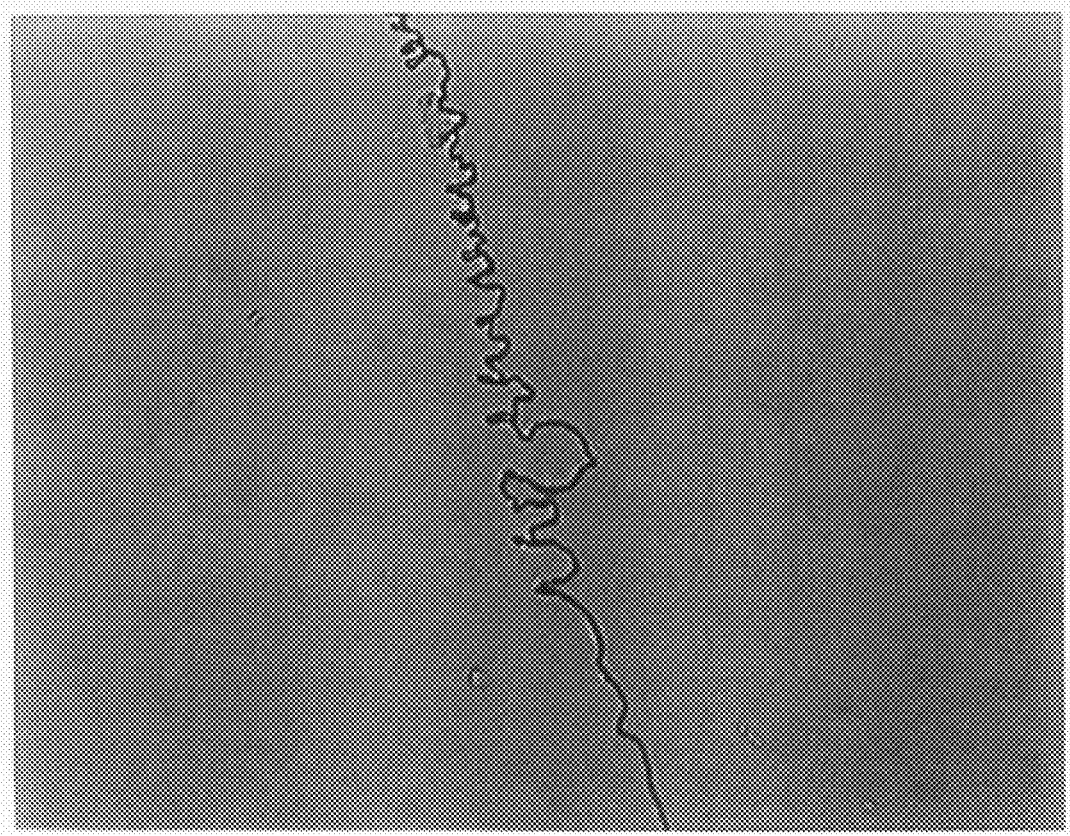
FIG. 3 is a polarizing microscopic photograph showing a sample of a mono-O-(phytanyl)pentaerythritol/water system.

Subsequently, the thus obtained sample of mono-O-(phytanyl)pentaerythritol/water system (the concentration of the amphiphilic compound: 74.6% by mass) was observed by polarizing microscopy. In entire region of the lipid portions, optically isotropic textures peculiar to the cubic liquid crystals were observed (FIG. 3). In FIG. 3, the right region indicates water and the left region indicates the sample of mono-O-(phytanyl)pentaerythritol/water system. The left region was found to be optically isotropic as with water but highly viscous. Such observation indicates the formation of cubic liquid crystals. Further, even when water was added to the aforementioned sample sandwiched between a glass slide and a cover glass, optically isotropic texture regions corresponding to water and lipid portions formed a stable interface, and the optically isotropic texture of the lipid portions did not change even it was allowed to stand for a long period of time. This indicates that the cubic liquid crystals remain stable in the presence of excess water. As a result, the cubic liquid crystals formed by mono-O-(phytanyl)pentaerythritol were found to be type II.

Figure 4:
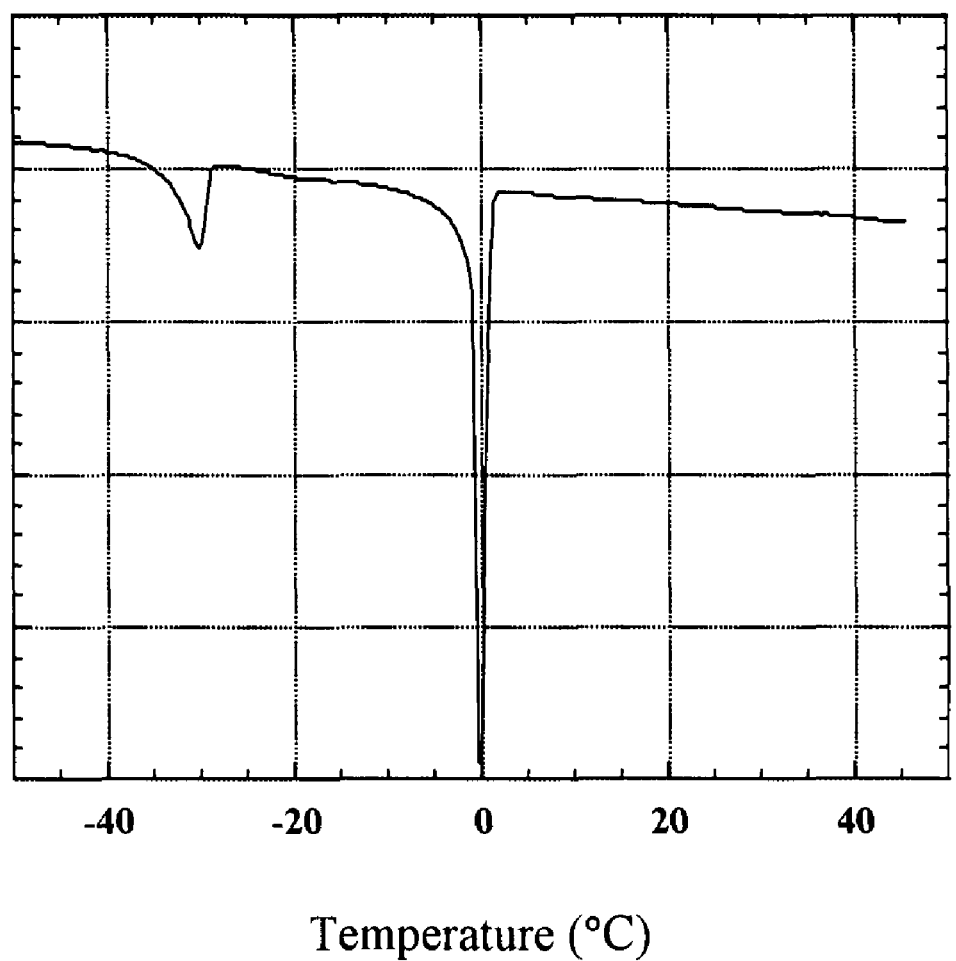
FIG. 4 shows a DSC curve for a sample of 72.4% by mass of a mono-O-(phytanyl)pentaerythritol/water system.

Subsequently, the sample of mono-O-(phytanyl)pentaerythritol/water system was subjected to differential scanning calorimetry (DSC) in a temperature range between −45° C. and 70° C. DSC analysis employed the Seiko SSC/560U differential scanning calorimeter (Seiko Instruments Inc.). The sample of mono-O-(phytanyl)pentaerythritol/water system (72.4% by mass) prepared by the above method was sealed in a DSC cell, and the sample was incubated while cooling at −45° C. for 3 hours to thoroughly form a hydrated solid of mono-O-(phytanyl)pentaerythritol (hereafter abbreviated as "hydrated solid"). Subsequently, this hydrated solid was heated at a rate of temperature increase of 0.5° C./minute and a melting behavior of the hydrated solid was inspected by DSC analysis. As a result, an endothermic peak resulting from melting of the hydrated solid that begins at around −40° C. and ends at around −27° C. and an endothermic peak resulting from ice melting observed between −10° C. and 1° C. were observed, as shown in FIG. 4. In FIG. 4, the left peak is the endothermic peak resulting from melting of the hydrated solid and the right peak is the endothermic peak resulting from ice melting. Although analysis was conducted up to 70° C., other thermal transition was not observed. Substantially the same results were obtained at other concentrations. Thus, the $T_K$ of mono-O-(phytanyl)pentaerythritol was concluded to be 0° C. or lower.

Subsequently, the sample of mono-O-(phytanyl)pentaerythritol/water system was confirmed to be a cubic liquid crystal by small-angle x-ray scattering (SAXS). The sample of mono-O-(phytanyl)pentaerythritol/water system was introduced into a quartz X-ray capillary tube, the tip of the capillary was sealed using an oxygen burner, and the capillary tube was subjected to the SAXS analysis. SAXS analysis was carried out using the RU-200 X-ray generator (Rigaku) at the wavelength of 0.154 nm. The sample sealed in the X-ray capillary tube was incubated at each measurement temperature for at least 15 hours. After the sample reached thermal equilibrium, the sample was subjected to SAXS analysis for 30 to 45 minutes of X-ray irradiation. The results of SAXS analysis did not change even when the duration of incubation was extended to 72 hours to 5 days at a maximum. This indicated that the cubic liquid crystals in equilibrium were assayed in the experiment condition as shown above.

As a result of SAXS analysis, 6 sharp scattering peaks were observed at least in a temperature range between 1° C. and 40° C. Depending on the concentration of mono-O-(phytanyl)pentaerythritol and the temperature, the peak value ratio exhibited a ratio peculiar to the cubic liquid crystal belonging to the crystallographic space group Pn3m: $\sqrt{2}:\sqrt{3}:\sqrt{4}:\sqrt{6}:\sqrt{8}:\sqrt{9}$ (FIG. 5A), or a ratio peculiar to the cubic liquid crystal belonging to the crystallographic space group Ia3d: $\sqrt{3}:\sqrt{4}:\sqrt{7}:\sqrt{8}:\sqrt{10}:\sqrt{11}$ (FIG. 5B). Thus, the sample of mono-O-(phytanyl)pentaerythritol/water system was confirmed to form cubic liquid crystals that belong to the crystallographic space groups Pn3m and Ia3d. Since the lattice constant of cubic liquid crystals observed at a mono-O-(phytanyl)pentaerythritol concentration of 73% to 74% by mass or lower (that varies depending on a temperature) in the presence of excess water was constant regardless of the mono-O-(phytanyl)pentaerythritol concentration, the cubic liquid crystals formed by mono-O-(phytanyl)pentaerythritol were found to be "type II" cubic liquid crystals that were stable in the presence of excess water.

Figure 5:
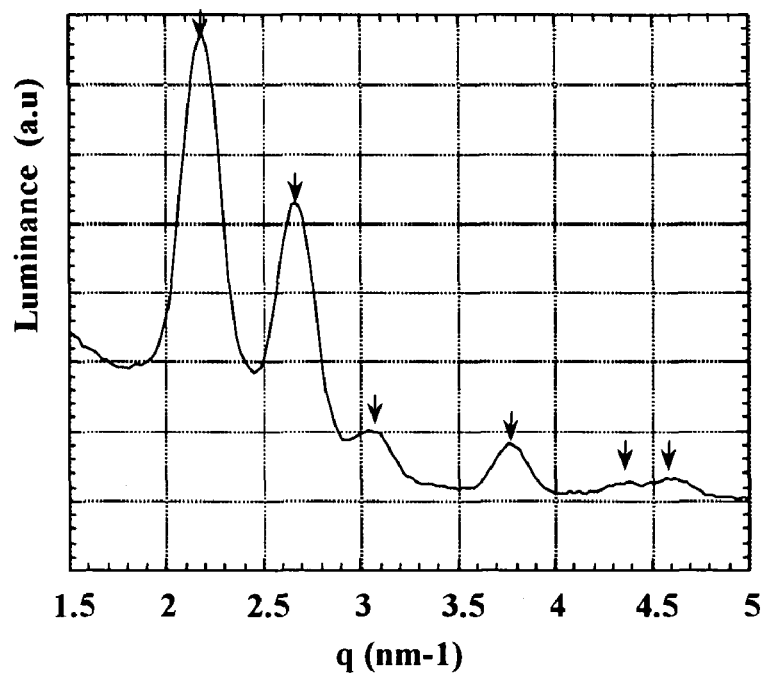
FIG. 5 shows the results of SAXS analysis of a sample of a mono-O-(phytanyl)pentaerythritol/water system (1° C.).
Figure 5:
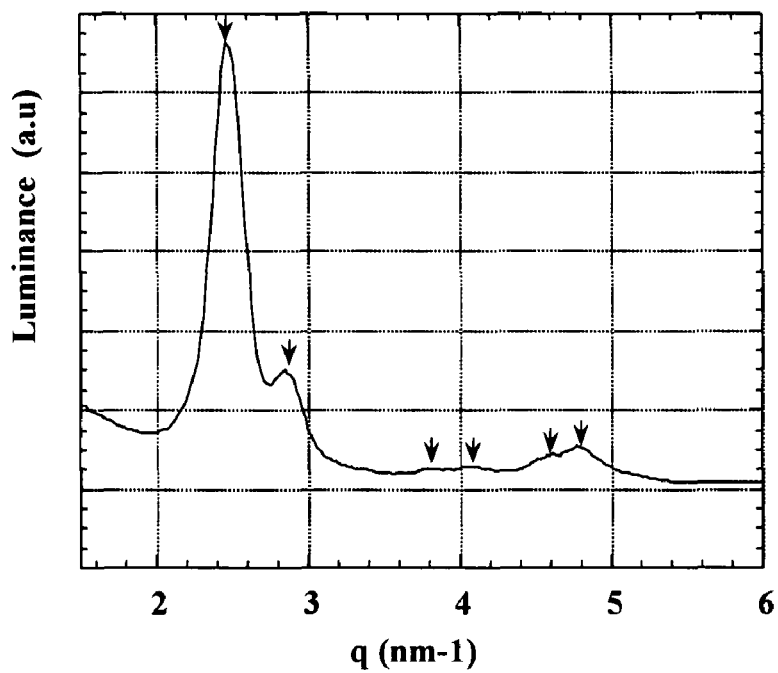

FIG. 5 shows the results of SAXS analysis of the sample of mono-O-(phytanyl)pentaerythritol/water system at 1° C. At 1° C., the peak of the hydrated solid observed at −50° C. disappeared, and only the 6 peaks exhibiting the ratios peculiar to the cubic liquid crystals were observed.

FIG. 5A:

56.7% by mass; Pn3m cubic liquid crystals; lattice constant=8.2 nm

FIG. 5B:

74.6% by mass; Ia3d cubic liquid crystals; lattice constant=12.3 nm

Further, the $d_{hc}$ value of a bilayer membrane of mono-O-(phytanyl)pentaerythritol of the cubic liquid crystal structure in the sample of mono-O-(phytanyl)pentaerythritol/water system was calculated based on the results of SAXS analysis and determined to be 1.17±0.1 nm. This value does not contradict the fact that the $d_{hc}$ value of the amphiphilic lipid bilayer, which is formed by an amphiphilic lipid having an O-phytanyl chain as a hydrophobic chain, is 1.2±0.1 nm (Hato, M. Minamikawa, H., Tamada, K., Baba, T., and Y. Tanabe, Adv. Colloid Interface Sci., 80, 233-270, 1999). Thus, the cubic liquid crystals formed by mono-O-(phytanyl) pentaerythritol were found to be of a bicontinuous type.

Examples of samples (classified depending on the concentration of the amphiphilic lipid) in which formation of cubic liquid crystals were confirmed through the above experiment are shown in Table 3 below.

TABLE 3

| Sample No. | Concentration of amphiphilic compound (% by mass) | Temperature at which formation of cubic liquid crystals was observed (° C.) |
| --- | --- | --- |
| 1 | 56.7 | 1 to 40 (Two-phase system of Pn3m cubic liquid crystals and excess water) |
| 2 | 65.3 | 1 to 40 (Two-phase system of Pn3m cubic liquid crystals and excess water) |
| 3 | 69.9 | 1 to 40 (Two-phase system of Pn3m cubic liquid crystals and excess water) |
| 4 | 72.4 | 1 to 40 (Two-phase system of Pn3m cubic liquid crystals and excess water) |
| 5 | 74.6 | 1 to 20 (Ia3d cubic liquid crystals) 25 (Two-phase system of Ia3d and Pn3m cubic liquid crystals) 30 to 40 (Pn3m cubic liquid crystals) |
| 6 | 78.0 | 1 to 40 (Ia3d cubic liquid crystals) |
| 7 | 81.6 | 1 to 15 (Two-phase system of Ia3d cubic liquid crystals lamellar liquid crystals) 20 to 40 (Ia3d cubic liquid crystals) |

Figure 6:
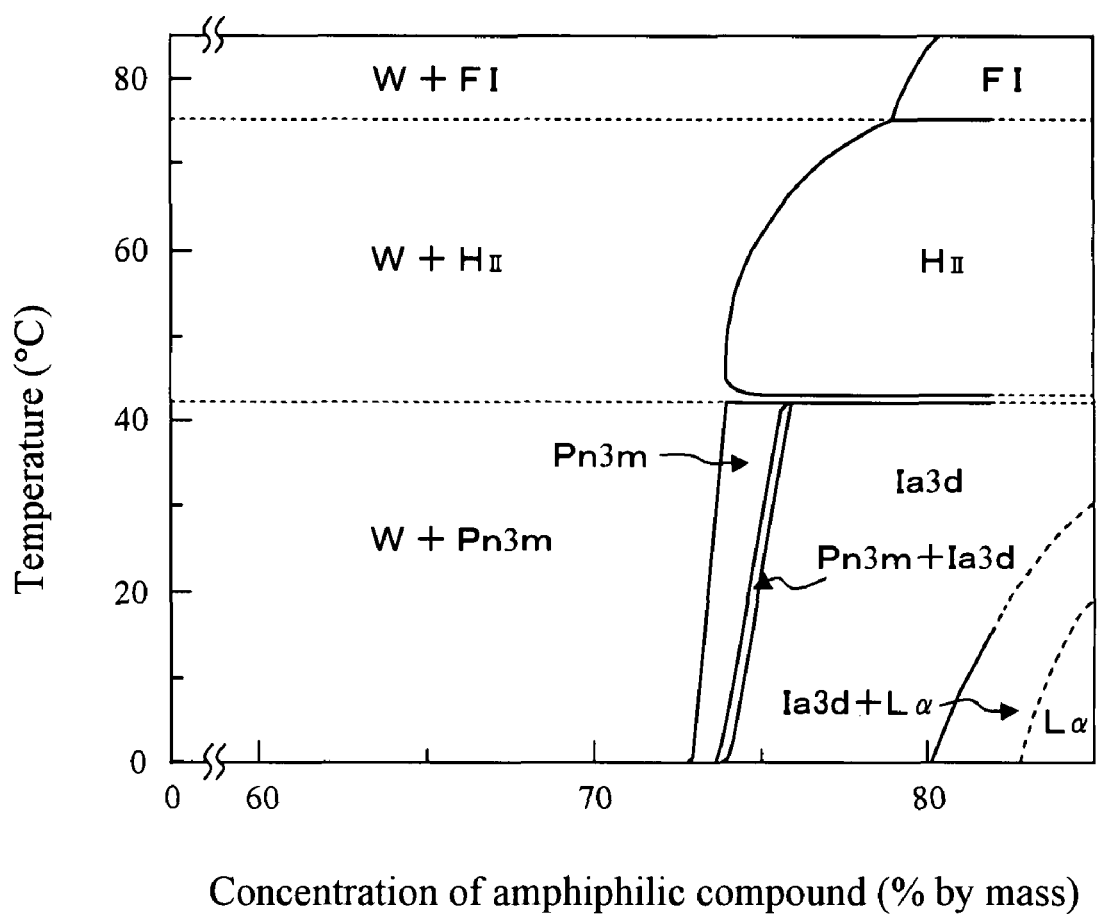
FIG. 6 is a concentration-temperature dependent partial phase diagram of a mono-O-(phytanyl)pentaerythritol/water system.

FIG. 6 shows a concentration-temperature-dependent partial phase diagram of the sample of mono-O-(phytanyl)pentaerythritol/water system as determined based on the above results.

In this description, reference marks in the phase diagrams are as indicated below.

W: aqueous phase (a dilute aqueous solution comprising a trace amount of amphiphilic compound dissolved therein)

$H_{II}$: inverted hexagonal liquid crystals

Pn3m: Pn3m cubic liquid crystals

Ia3d: Ia3d cubic liquid crystals

Lα: lamellar liquid crystals

LC: liquid crystals with unspecified structure

FI: isotropic liquid phase (not cubic liquid crystals)

(a portion containing two types of marks is a coexisting region)

Example 4

Formation and Analysis of Type II Cubic Liquid Crystals-2

Mono-O-(3,7,11,15-tetramethylhexadecanoyl)pentaerythritol (hereafter mono-O-(phytanoyl)pentaerythritol; formula (6) above) and pure water were homogeneously mixed in accordance with the same procedure as in Example 3 to obtain the sample of mono-O-(3,7,11,15-tetramethylhexadecanoyl)pentaerythritol/water system. This sample of mono-O-(3,7,11,15-tetramethylhexadecanoyl)pentaerythritol/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals were found to be stably formed at least in a temperature range between 1° C. and 65° C. The lattice constant of the cubic liquid crystals of 58.9% by mass of mono-O-(phytanoyl)pentaerythritol/water system was 10.6 nm (25° C.) to 8.3 nm (55° C.).

This sample of mono-O-(3,7,11,15-tetramethylhexadecanoyl)pentaerythritol/water system was subjected to differential scanning calorimetry (DSC). No thermal transition was observed except for a peak resulting from melting of the hydrated solid of mono-O-(3,7,11,15-tetramethylhexadecanoyl)pentaerythritol that begins at around −8° C. and ends at around −2.5° C. and a peak resulting from ice melting at around 0° C. Substantially the same results were obtained at all the concentrations of amphiphilic compounds inspected. Thus, $T_K$ of mono-O-(phytanoyl)pentaerythritol was concluded to be 0° C. or lower.

The samples in which formation of cubic liquid crystals was found in the above experiment are as shown below.

TABLE 4

| Sample No. | Concentration of amphiphilic compound (% by mass) | Temperature at which formation of cubic liquid crystals was observed (° C.) |
| --- | --- | --- |
| 1 | 56.0 | 1 (Two-phase system of Pn3m cubic liquid crystals and lamellar liquid crystals) 25 to 65 (Pn3m cubic liquid crystals) |
| 2 | 58.9 | 1 to 65 (Pn3m cubic liquid crystals) |

TABLE 4-continued

| Sample No. | Concentration of amphiphilic compound (% by mass) | Temperature at which formation of cubic liquid crystals was observed (° C.) |
|---|---|---|
| 3 | 67.2 | 1 to 35 (Two-phase system of Pn3m cubic liquid crystals and lamellar liquid crystals) 45 to 55 (Pn3m cubic liquid crystals) |

Example 5

Formation and Analysis of Type II Cubic Liquid Crystals-3

1-O-(3,7,11,15-tetramethylhexadecanoyl)erythritol (hereafter 1-O-(phytanoyl)erythritol; formula (4) above) and pure water were mixed in accordance with the same procedure as in Example 3 to obtain the sample of 1-O-(phytanoyl)erythritol/water system. This sample of 1-O-(phytanoyl)erythritol/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals or Ia3d cubic liquid crystals were found to be stably formed at least in a temperature range between 1° C. and 60° C. The lattice constants of the Pn3m cubic liquid crystals formed by 52.3% by mass of 1-O-(phytanoyl)erythritol were 11.4 nm (1° C.), 11.3 nm (25° C.), and 10.1 nm (45° C.).

The sample of 1-O-(phytanoyl)erythritol/water system was subjected to differential scanning calorimetry (DSC). An endothermic peak resulting from ice melting at around 0° C. and an overlapping endothermic peak resulting from melting of the hydrated solid of 1-O-(phytanoyl)erythritol at around −0.6° C. were observed. Thus, $T_K$ of 1-O-(phytanoyl)erythritol was concluded to be 0° C. or lower.

The samples in which formation of cubic liquid crystals was observed in the above experiment are as shown below.

TABLE 5

| Sample No. | Concentration of amphiphilic compound (% by mass) | Temperature at which formation of cubic liquid crystals was observed (° C.) |
|---|---|---|
| 1 | 52.3 | 1 to 60 (Pn3m cubic liquid crystals) |
| 2 | 58.0 | 1 to 60 (Pn3m cubic liquid crystals) |
| 3 | 62 | 1 to 20 (Pn3m cubic liquid crystals) 25 to 40 (Ia3d cubic liquid crystals) 45 to 60 (Pn3m cubic liquid crystals) |
| 4 | 65.1 | 1 to 60 (Ia3d cubic liquid crystals) |

Example 6

Formation and Analysis of Type II Cubic Liquid Crystals-4

1-O-(5,9,13-trimethyltetradecyl)erythritol (formula (3) above) and pure water were mixed in accordance with the same procedure as in Example 3 to obtain the sample of 1-O-(5,9,13-trimethyltetradecyl)erythritol/water system. This sample of 1-O-(5,9,13-trimethyltetradecyl)erythritol/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals or Ia3d cubic liquid crystals were found to be stably formed at least in a temperature range between 1° C. and 75° C. The lattice constants of the Ia3d cubic liquid crystals in 53.7% by mass of the 1-O-(5,9,13-trimethyltetradecyl)erythritol/water system were 17.3 nm (20° C.), 17.2 nm (35° C.), and 17.1 nm (40° C.).

This sample of 1-O-(5,9,13-trimethyltetradecyl)erythritol/water system was subjected to differential scanning calorimetry (DSC) in the same manner as in Example 3. Only an endothermic peak resulting from ice melting was observed at around 0° C. This strongly suggests that $T_K$ of 1-O-(5,9,13-trimethyltetradecyl)erythritol is 0° C. or lower.

The samples in which formation of cubic liquid crystals was observed in the above experiment are as shown below.

TABLE 6

| Sample No. | Concentration of amphiphilic compound (% by mass) | Temperature at which formation of cubic liquid crystals was observed (° C.) |
|---|---|---|
| 1 | 53.7 | 1 to 35 (Ia3d cubic liquid crystals) 40 (Ia3d + Pn3m cubic liquid crystals) 45 to 75 (Pn3m cubic liquid crystals) |

TABLE 6-continued

| Sample No. | Concentration of amphiphilic compound (% by mass) | Temperature at which formation of cubic liquid crystals was observed (° C.) |
|---|---|---|
| 2 | 58.6 | 1 to 30 (Two-phase system of Ia3d cubic liquid crystals and lamellar liquid crystals) 35 to 50 (Ia3d cubic liquid crystals) 55 to 75 (Pn3m cubic liquid crystals) |

Example 7

Formation and Analysis of Type II Cubic Liquid Crystals-5

1-O-(3,7,11-trimethyldodecyl)erythritol (formula (2) above) and pure water were mixed in accordance with the same procedure as in Example 3 to obtain the sample of 1-O-(3,7,11-trimethyldodecyl)erythritol/water system. This sample of 1-O-(3,7,11-trimethyldodecyl)erythritol/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals were found to be stably formed at least in a temperature range between 1° C. and 60° C.

The samples in which formation of cubic liquid crystals was found in the above experiment are as shown below.

TABLE 7

| Sample No. | Concentration of amphiphilic compound (% by mass) | Temperature at which formation of cubic liquid crystals was observed (° C.) |
|---|---|---|
| 1 | 53.5 | 1 to 60 (Pn3m cubic liquid crystals) |
| 2 | 59.4 | 1 to 60 (Ia3d cubic liquid crystals) |
| 3 | 62.4 | 1 to 60 (Ia3d cubic liquid crystals) |

Example 8

Formation and Analysis of Type II Cubic Liquid Crystals-6

1-O-(5,9,13,17-tetramethyloctadecanoyl)erythritol (formula (7) above) and pure water were homogeneously mixed in the same manner as in Example 3 to obtain the sample of 1-O-(5,9,13,17-tetramethyloctadecanoyl)erythritol/water system. This sample of 1-O-(5,9,13,17-tetramethyloctadecanoyl)erythritol/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals were found to be stably formed at least in a temperature range between 1° C. and 60° C.

This sample of 1-O-(5,9,13,17-tetramethyloctadecanoyl)erythritol/water system was subjected to differential scanning calorimetry (DSC), and no thermal transition was observed except for the endothermic peak resulting from ice melting at around 0° C. Also, the hydrated solid of 1-O-(5,9,13,17-tetramethyloctadecanoyl)erythritol formed at low temperatures as in the case of Example 3 was incubated at 1° C. As a result, the hydrated solid was transformed into the cubic liquid crystals. Thus, $T_K$ of 1-O-(5,9,13,17-tetramethyloctadecanoyl)erythritol was concluded to be 0° C. or lower.

The samples in which formation of cubic liquid crystals was found in the above experiment are as shown below.

TABLE 8

| Sample No. | Concentration of amphiphilic compound (% by mass) | Temperature at which formation of cubic liquid crystals was observed (° C.) |
|---|---|---|
| 1 | 61.1 | 1 to 60 (Pn3m cubic liquid crystals) |
| 2 | 65.2 | 1 to 60 (Pn3m cubic liquid crystals) |

Example 9

Formation and Analysis of Type II Cubic Liquid Crystals-7

Mono-O-(5,9,13,17-tetramethyloctadecyl)pentaerythritol (formula (8) above) and pure water were homogeneously mixed in the same manner as in Example 3 to obtain the sample of mono-O-(5,9,13,17-tetramethyloctadecyl)pentaerythritol/water system. This sample of mono-O-(5,9,13,17-tetramethyloctadecyl)pentaerythritol lipid/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals were found to be stably formed.

The sample of mono-O-(5,9,13,17-tetramethyloctadecyl)pentaerythritol/water system was subjected to differential scanning calorimetry (DSC). No thermal transition was observed except for the endothermic peak resulting from ice melting at around 0° C. Also, the hydrated solid of mono-O-(5,9,13,17-tetramethyloctadecyl)pentaerythritol formed at low temperatures as in the case of Example 3 was incubated at 1° C., and it was transformed into cubic liquid crystals. Thus, $T_K$ of mono-O-(5,9,13,17-tetramethyloctadecyl)pentaerythritol was concluded to be 0° C. or lower.

The samples in which formation of cubic liquid crystals was found in the above experiment are as shown below.

TABLE 9

| Sample No. | Concentration of amphiphilic compound (% by mass) | Temperature at which formation of cubic liquid crystals was observed (° C.) |
|---|---|---|
| 1 | 59.3 | 1 to 30 (Pn3m cubic liquid crystals) |
| 2 | 66.2 | 1 to 30 (Pn3m cubic liquid crystals) |

Example 10

Formation of Type II Cubic Liquid Crystals and Analysis Thereof-8

Mono-O-(5,9,13,17-tetramethyloctadecanoyl)pentaerythritol (formula (9) above) and pure water were homogeneously mixed in accordance with the same procedure as in Example 3 to obtain the sample of mono-O-(5,9,13,17-tetramethyloctadecanoyl)pentaerythritol/water system. This sample of mono-O-(5,9,13,17-tetramethyloctadecanoyl)pentaerythritol/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals were found to be stably formed.

This sample of mono-O-(5,9,13,17-tetramethyloctadecanoyl)pentaerythritol/water system was subjected to differential scanning calorimetry (DSC). The endothermic peak resulting from melting of a hydrated solid of a lipid was found to begin at around −20° C. and to end at −15° C. At a higher temperature, no thermal transition was observed except for the endothermic peak resulting from ice melting at around 0° C. Thus, $T_K$ of mono-O-(5,9,13,17-tetramethyloctadecanoyl)pentaerythritol was concluded to be 0° C. or lower.

The samples in which formation of cubic liquid crystals was found in the above experiment are as shown below.

Example 11

Formation and Analysis of Type II Cubic Liquid Crystals-9

1-O-(5,9,13,17-tetramethyloctadecyl)-β-D-xylopyranoside (hereafter β-XylC22; formula (10) above) and pure water were homogeneously mixed in accordance with the same procedure as in Example 3 to obtain the sample of β-XylC22/water system. This sample of β-XylC22/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals and Ia3d cubic liquid crystals were found to be stably formed at least in a temperature range between 1° C. and 45° C. The lattice constants of the cubic liquid crystals comprising 61.5% by mass of β-XylC22 determined based on the peak values were 10.1 nm (1° C.), 9.9 nm (30° C.), and 9.5 nm (40° C.).

The sample of β-XylC22/water system was subjected to differential scanning calorimetry (DSC) in the same manner as in Example 3. The endothermic peak resulting from melting of a hydrated solid of β-XylC22 was found to begin at around −13° C. and to end at −9° C. At a higher temperature, no thermal transition was observed except for the endothermic peak resulting from ice melting at around 0° C. Thus, $T_K$ of β-XylC22 was concluded to be 0° C. or lower.

The samples in which formation of cubic liquid crystals was found in the above experiment are as shown below.

TABLE 10

| Sample No. | Concentration of amphiphilic compound (% by mass) | Temperature at which formation of cubic liquid crystals was observed (° C.) |
|---|---|---|
| 1 | 58.0 | 1 to 60 (Pn3m cubic liquid crystals) |
| 2 | 61.7 | 1 to 60 (Pn3m cubic liquid crystals) |

TABLE 11

| Sample No. | Concentration of amphiphilic compound (% by mass) | Temperature at which formation of cubic liquid crystals was observed (° C.) |
|---|---|---|
| 1 | 60.0 | 1 to 45 (Pn3m cubic liquid crystals) |
| 2 | 61.5 | 1 to 45 (Pn3m cubic liquid crystals) |
| 3 | 68.2 | 1 to 30 (Ia3d cubic liquid crystals) |
|   | 68.2 | 33 to 45 (Pn3m cubic liquid crystals) |

Example 12

Formation and Analysis of Type II Cubic Liquid Crystals-10

1-O-(3,7,11,15-tetramethylhexadecyl)-α-D-xylopyranoside (hereafter α-XP; formula (11) above) and pure water were mixed in accordance with the same procedure as in Example 3 to obtain the sample of α-XP/water system.

The thus prepared sample of α-XP/water system was observed by polarizing microscopy. This demonstrated that inverted hexagonal liquid crystals were formed at the interface with water and but that cubic liquid crystals were formed in regions with high amphiphilic compound concentration in the sample. Since inverted hexagonal liquid crystals were formed at the interface with water in the sample of α-XP/water system, the cubic liquid crystals formed by α-XP were found to be of type II. Further, the sample of α-XP/water system was subjected to SAXS analysis and $d_{hc}$ value determination based on the results of SAXS analysis in the same manner as in Example 3. It was verified that bicontinuous Ia3d cubic liquid crystals were formed at least in a concentration range between 78% and 84% by mass and at least in a temperature range between 1° C. and 45° C. The lattice constants of cubic liquid crystals in the α-XP/water system comprising 84.2% by mass of α-XP were 9.8 nm (1° C.), 9.7 nm (25° C.), and 9.6 nm (40° C.).

The sample of α-XP/water system was subjected to differential scanning calorimetry (DSC). As a result, only the endothermic peak resulting from the transformation of α-XP that begins at around −10° C. and ends at around −1° C. and the overlapping endothermic peak resulting from ice melting at 0° C. were observed. Thus, $T_K$ of α-XP was concluded to be 0° C. or lower.

The samples in which formation of cubic liquid crystals was found in the above experiment are as shown below.

TABLE 12

| Sample No. | Concentration of amphiphilic compound (% by mass) | Temperature at which formation of cubic liquid crystals was observed (° C.) |
|---|---|---|
| 1 | 78.0 | 1 (Ia3d cubic liquid crystals) |
| 2 | 82.0 | 1 to 45 (Ia3d cubic liquid crystals) |
| 3 | 84.2 | 1 to 45 (Ia3d cubic liquid crystals) |

Figure 7:
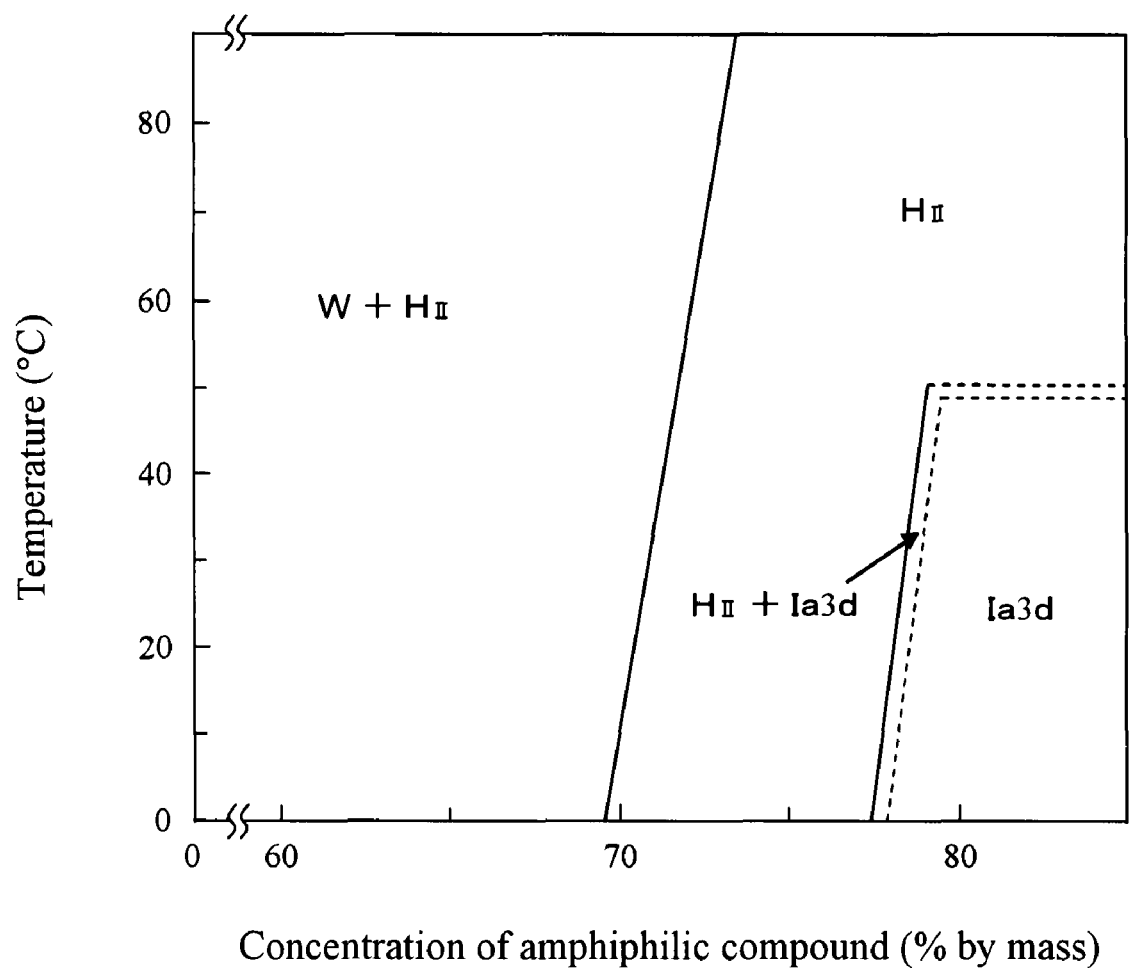
FIG. 7 is a concentration-temperature dependent partial phase diagram of a 1-O-(3,7,11,15-tetramethylhexadecyl)-α-D-xylopyranoside (α-XP)/water system.

FIG. 7 shows a concentration-temperature-dependent partial phase diagram of the sample of α-XP/water system as determined based on the above results.

Example 13

Formation and Analysis of Type II Cubic Liquid Crystals-11

Mono-O-(5,9,13-trimethyltetradecyl)pentaerythritol (formula (12) above) and pure water were homogeneously mixed in accordance with the same procedure as in Example 3 to obtain the sample of mono-O-(5,9,13-trimethyltetradecyl)pentaerythritol/water system. The sample of mono-O-(5,9,13-trimethyltetradecyl)pentaerythritol/water system was subjected to the penetration experiment under a polarizing microscope, SAXS analysis, and $d_{hc}$ value determination based on the results of SAXS analysis in the same manner as in Example 3. As a result, bicontinuous type II Pn3m cubic liquid crystals were found to be stably formed at least in a temperature range between 1° C. and 4° C. and at a concentration of 55.3% by mass of mono-O-(5,9,13-trimethyltetradecyl)pentaerythritol.

The sample of mono-O-(5,9,13-trimethyltetradecyl)pentaerythritol/water system was subjected to differential scanning calorimetry (DSC) in the same manner as in Example 3. Only the endothermic peak that begins at around −10° C. and ends at 1° C. was observed. Thus, $T_K$ of mono-O-(5,9,13-trimethyltetradecyl)pentaerythritol was concluded to be 0° C. or lower.

Example 14

Formation and Analysis of Type II Cubic Liquid Crystals-12

6-O-(5,9,13,17-tetramethyloctadecanoyl)-L-ascorbic acid (formula (15) above) and pure water were mixed in accordance with the same procedure as in Example 3 to obtain the sample of 6-O-(5,9,13,17-tetramethyloctadecanoyl)-L-ascorbic acid/water system. The thus prepared sample of 6-O-(5,9,13,17-tetramethyloctadecanoyl)-L-ascorbic acid/water system was subjected to the penetration experiment under a polarizing microscope, SAXS analysis, and $d_{hc}$ value determination based on the results of SAXS analysis in the same manner as in Example 3. As a result, bicontinuous type II Pn3m or Ia3d cubic liquid crystals were found to be formed at least in a temperature range between 1° C. and 60° C. The Pn3m or Ia3d cubic liquid crystals are generated depending on the concentration of 6-O-(5,9,13,17-tetramethyloctadecanoyl)-L-ascorbic acid and the temperature.

Further, the lattice constants of the Pn3m cubic liquid crystals (6-O-(5,9,13,17-tetramethyloctadecanoyl)-L-ascorbic acid, 61% by mass) determined based on the peak values were 12.2 nm (1° C.), 12.2 nm (20° C.), 12.1 nm (30° C.), 11.4 nm (40° C.), 11.0 nm (50° C.), and 10.1 nm (60° C.). The lattice constants of the Ia3d cubic liquid crystals (6-O-(5,9,13,17-tetramethyloctadecanoyl)-L-ascorbic acid, 69% by mass) were 17.4 nm (30° C.), 16.9 nm (40° C.), and 17.0 nm (50° C.).

The sample of 6-O-(5,9,13,17-tetramethyloctadecanoyl)-L-ascorbic acid/water system was subjected to differential scanning calorimetry (DSC) in the same manner as in Example 3 in a temperature range between −60° C. and 50° C. No thermal transition was observed except for the endothermic peak resulting from ice melting at around 0° C. Thus, $T_K$ of 6-O-(5,9,13,17-tetramethyloctadecanoyl)-L-ascorbic acid was concluded to be 0° C. or lower.

The samples in which formation of cubic liquid crystals was found in the above experiment are as shown below.

TABLE 13

| Sample No. | Concentration of amphiphilic compound (% by mass) | Temperature at which formation of cubic liquid crystals was observed (° C.) |
|---|---|---|
| 1 | 61 | 1 to 60 (Pn3m cubic liquid crystals) |
| 2 | 65 | 1 to 60 (Pn3m cubic liquid crystals) |
| 3 | 69 | 1 to 10 (Pn3m cubic liquid crystals) |
|   |    | 20 (Two-phase system of Pn3m and Ia3d cubic liquid crystals) |
|   |    | 25 to 50 (Ia3d cubic liquid crystals) |
|   |    | 60 (Pn3m cubic liquid crystals) |

Comparative Example 1

Formation and Analysis of Type II Hexagonal Liquid Crystals

1-O-(3,7,11-15-tetramethylhexadecyl)glycerol (IV/OV=0.524) and pure water were homogeneously mixed in accordance with the same procedure as in Example 3 to obtain the sample of 1-O-(3,7,11-15-tetramethylhexadecyl)glycerol/water system. This sample of 1-O-(3,7,11-15-tetramethylhexadecyl)glycerol/water system was observed by polarizing microscopy. As a result, a texture peculiar to type II hexagonal liquid crystals was observed at the 1-O-(3,7,11-15-tetramethylhexadecyl)glycerol/water interface, and the optically isotropic texture peculiar to the cubic liquid crystals was not observed at all. Thus, the 1-O-(3,7,11-15-tetramethylhexadecyl)glycerol was found to form type II hexagonal liquid crystals instead of cubic liquid crystals.

Comparative Example 2

Formation and Analysis of Lamellar Liquid Crystals 3,7,11-trimethyldodecane-1,2,3-triol (IV/OV=1.154) (formula (14) below) and pure water were homogeneously mixed in accordance with the same procedures as in Example 3 to obtain the sample of 3,7,11-trimethyldodecane-1,2,3-triol/water system.

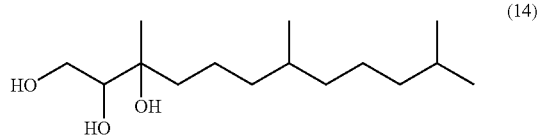
(14)

1-O-(3,7,11,15-tetramethylhexadecyl)-β-D-glucopyranoside (IV/OV=1.052) and pure water were homogeneously mixed in accordance with the same procedure as in Example 3 to obtain the sample of 1-O-(3,7,11,15-tetramethylhexadecyl)-β-D-glucopyranoside/water system.

1-O-(3,7,11,15-tetramethylhexadecyl)-β-D-maltoside (IV/OV=1.517) and pure water were homogeneously mixed in accordance with the same procedure as in Example 3 to obtain the sample of 1-O-(3,7,11,15-tetramethylhexadecyl)-13-D-maltoside/water system.

The thus prepared samples of amphiphilic lipids/water systems were subjected to polarizing microscopic observation. As a result, myelin growth peculiar to the lamellar liquid crystals was observed at the amphiphilic lipid/water interfaces of both samples, although no isotropic texture peculiar to the cubic liquid crystals was observed. Thus, these amphiphilic lipids were found to form lamellar liquid crystals.

Example 15

Formation and Analysis of Two Constituent Compounds-Based Type II Cubic Liquid Crystals-1

1-O-(3,7,11,15-tetramethylhexadecyl)-α-D-xylopyranoside (formula (11) above, hereafter abbreviated as "α-XP (or α-form)," $T_K$ is 0° C. or lower) and 1-O-(3,7,11,15-tetramethylhexadecyl)-β-D-xylopyranoside (formula (13) above; hereafter abbreviated as "β-XP (or β-form)," $T_K$ is about 10° C.) were homogeneously mixed in pure water in accordance with the same procedure as in Example 3 to obtain a sample of amphiphilic compound/water system. The sample of amphiphilic compound/water system was inspected in the same manner as in Example 3. As a result, such α-XP and β-XP-mixed system were found to form Pn3m cubic liquid crystals in a range of a molar fraction Xα of α-XP between 0.0 and at least 0.8, relative to the total amount of amphiphilic compound.

Figure 8:
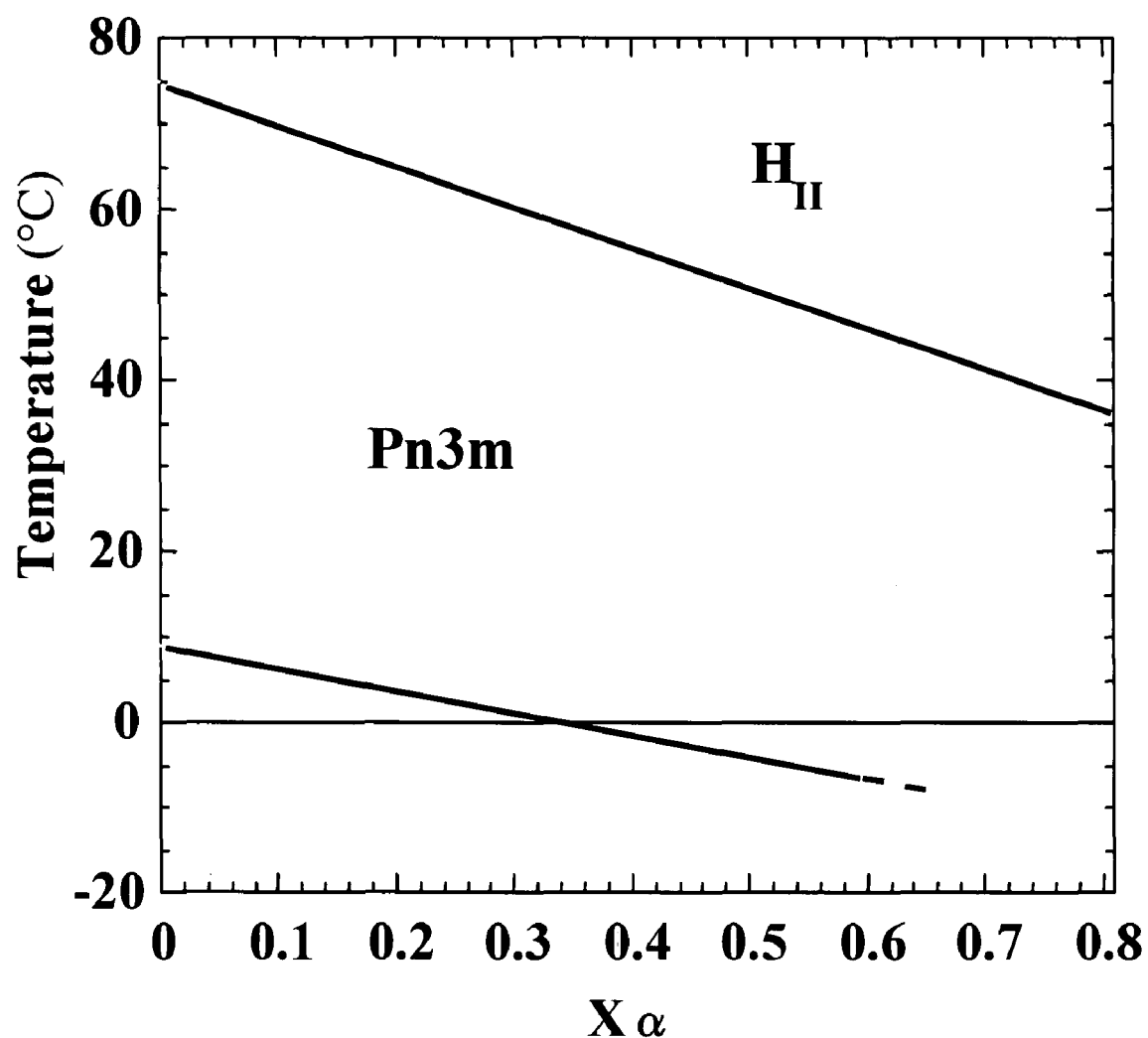
FIG. 8 is a phase diagram of the amphiphilic compound/water system comprising two constituent amphiphilic compounds, i.e., 1-O-(3,7,11,15-tetramethylhexadecyl)-α-D-xylopyranoside (α-XP) and 1-O-(3,7,11,15-tetramethylhexadecyl)-β-D-xylopyranoside (β-XP), and having 60%±3% by mass of total concentration of amphiphilic compound. Xα represents a molar fraction of α-XP relative to the total amount of amphiphilic compound.

FIG. 8 shows the correlation among the temperatures and compositions of amphiphilic compound of the sample and the structures of the cubic liquid crystals to be formed. In the region sandwiched by two lines ("Pn3 m") shown in FIG. 8, Pn3m cubic liquid crystals were formed.

As shown in FIG. 8, as the proportion of α-XP to the total amount of amphiphilic compound increased, the minimal temperature (i.e., the Krafft temperature ($T_K$)) and the maximal temperature, at which Pn3m cubic liquid crystals could be stably present, decreased at almost the same slope. When the molar fraction of α-XP was 0.2 relative to at the total amount of amphiphilic compound, stable Pn3m cubic liquid crystals were formed in a temperature range of 4° C. and 65° C. When such molar fraction was 0.35, such crystals were formed in a temperature range of 0° C. and 58° C. When such molar fraction was 0.6, such crystals were formed at least in a temperature range of 0° C. and 47° C. Accordingly, the cubic liquid crystals formed by 1-O-(3,7,11,15-tetramethylhexadecyl)-D-xylopyranoside, which is a mixture of α-XP and β-XP at a molar fraction of the α-form of 0.2 or higher, were found to be thermodynamically stably formed even at 4° C. By mixing β-XP and α-XP, cubic liquid crystals were found to be formed at a temperature lower than $T_K$ when β-XP was used alone.

Example 16

Formation and Analysis of two Constituent Compounds-Based Type II Cubic Liquid Crystals-2

Mono-O-(phytanyl)pentaerythritol (formula (5) above) formed bicontinuous type II Pn3m cubic liquid crystals at room temperature in a concentration range of 1% to 75% by mass (73% to 75% by mass in a mono-phase region) and formed Ia3d cubic liquid crystals in a concentration range of 76% to 85% by mass. $T_K$ of mono-O-(phytanyl)pentaerythritol is 0° C. or lower, and cubic liquid crystals thereof can be formed up to 40° C. Thus, in the case of mono-O-(phytanyl)pentaerythritol, the stability at high-temperature regions is relatively low, the cubic liquid crystal structure is soft, and such structure is relatively fragile by salt, protein, or the like in an aqueous medium.

In contrast, 1-O-(3,7,11,15-tetramethylhexadecyl)-β-D-xylopyranoside (formula (13) above) can form bicontinuous type II Pn3m cubic liquid crystals in the presence of excess water, the maximal temperature at which the liquid crystal structure is formed is 75° C., and it is highly stable at high-temperature regions. Due to strong interactions at xylose portions, the cubic liquid crystal structure is also firm, and the cubic liquid crystal structure remains stable even in the presence of salt, protein, or the like in an aqueous medium. However, its $T_K$ is about 10° C., and no liquid crystal is formed at low-temperature regions.

With the use of such two types of amphiphilic compounds having different properties, two constituent compounds-based type II cubic liquid crystals were formed in the following manner.

First, mono-O-(phytanyl)pentaerythritol and 1-O-(3,7,11,15-tetramethylhexadecyl)-β-D-xylopyranoside were homogeneously mixed in pure water in accordance with the same procedure as in Example 3 to bring the total amphiphilic compound content to 60% by mass (in the presence of excess water). Thus, several samples of amphiphilic compound/water system comprising amphiphilic compounds at different quantitative ratios were obtained. These samples of amphiphilic compound/water system were inspected in the same manner as in Example 3. This demonstrated that Pn3m cubic liquid crystals were formed with such two constituent compounds-mixed systems.

Figure 9:
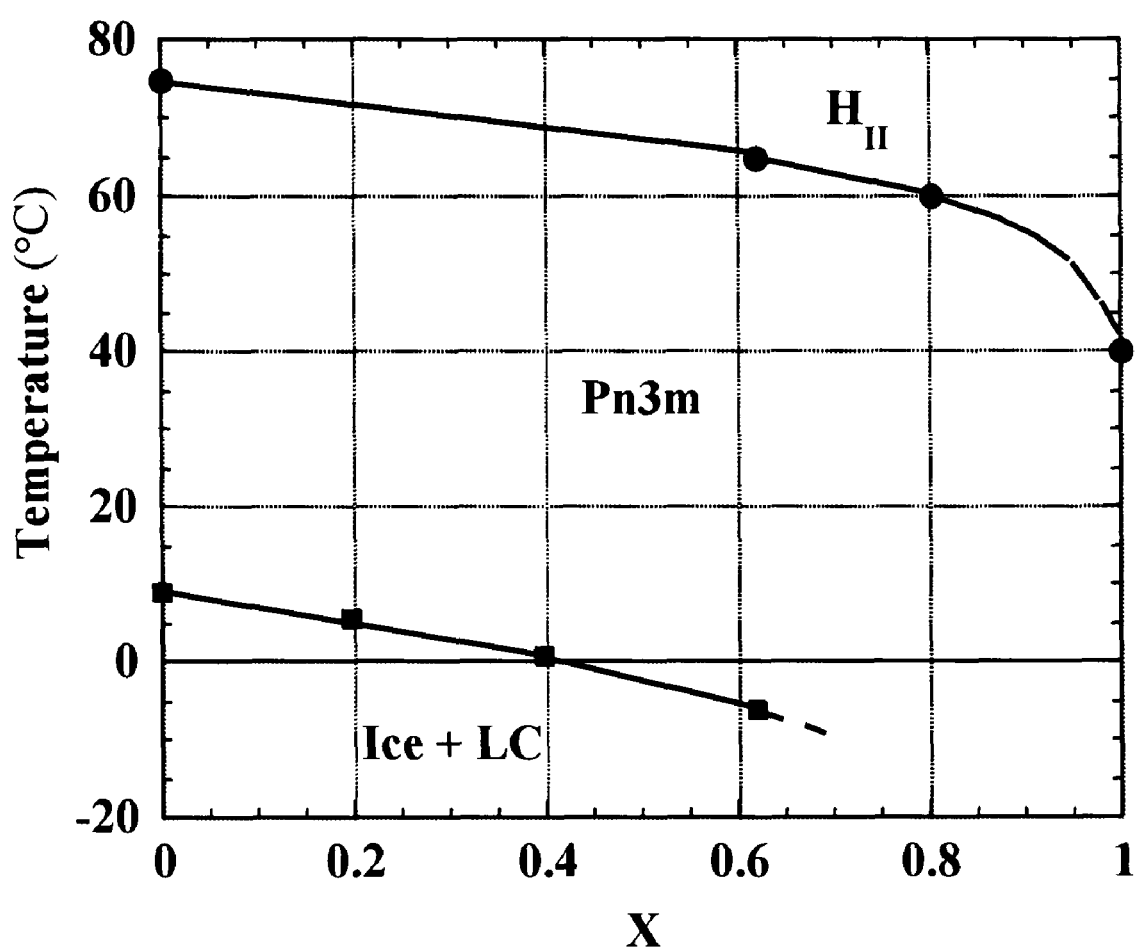
FIG. 9 is a phase diagram of the amphiphilic compound/water system comprising two constituent amphiphilic compounds, i.e., mono-O-(phytanyl)pentaerythritol and 1-O-(3,7,11,15-tetramethylhexadecyl)-β-D-xylopyranoside, and having 60%±3% by mass of the total concentration of amphiphilic compound. X represents a molar fraction of mono-O-(phytanyl)pentaerythritol relative to the total amount of amphiphilic compound.

FIG. 9 shows the correlation among the temperatures and compositions of amphiphilic compounds of the obtained samples, and the cubic liquid crystal structures to be formed. Pn3m cubic liquid crystals were formed in a region sandwiched by two curves ("Pn3 m").

As shown in FIG. 9, as the proportion of mono-O-(phytanyl)pentaerythritol to the total amount of amphiphilic compound increased, the minimal temperature and the maximal temperature, at which cubic liquid crystals could be stably present, decreased at almost the same slope. When the molar fraction of mono-O-(phytanyl)pentaerythritol was 0.2, stable bicontinuous type II Pn3m cubic liquid crystals were formed in a temperature range of 4° C. and 72° C. When such molar fraction was 0.4, such crystals were formed in a temperature range of 0° C. and 70° C. When such molar fraction was 0.8, such crystals were formed at least in a temperature range of 0° C. and 60° C. By mixing mono-O-(phytanyl)pentaerythritol with 1-O-(3,7,11,15-tetramethylhexadecyl)-β-D-xylopyranoside so as to bring the molar fraction of the former to 0.2 or higher, thermodynamically stable cubic liquid crystals were formed even at low temperatures (e.g., 4° C.).

The lattice constant of the cubic liquid crystals formed by 1-O-(3,7,11,15-tetramethylhexadecyl)-β-D-xylopyranoside alone was 9.2 nm. As the ratio of mono-O-(phytanyl)pentaerythritol to be mixed increased, however, the lattice constant was continuously reduced to 7.06 nm (in the case of 100% by mass of mono-O-(phytanyl)pentaerythritol). Also, as the lattice constant was reduced, the diameter of the water channel of the cubic liquid crystals was changed from 3.8 nm to 2.5 nm. This indicates that use of a plurality of amphiphilic compounds in combination can intentionally change fine structures of cubic liquid crystals.

Example 17

Formation and Analysis of Three Constituent Lipids-Based Type II Cubic Liquid Crystals-3

1-O-(3,7,11,15-tetramethylhexadecyl)-β-D-xylopyranoside (β-XP) mixed with 5% by mass of α-XP, and 3,7,11-trimethyldodecane-1,2,3-triol forming lamellar liquid crystals (hereafter referred to as the "secondary component") were homogeneously mixed in pure water in accordance with the same procedure as in Example 3 to obtain a sample of amphiphilic lipid/water system. The sample of amphiphilic lipid/water system was inspected in the same manner as in Example 3. As a result, formation of Pn3m cubic liquid crystals using the three types of amphiphilic lipids-mixed system was observed until the content of the secondary component reached at least 50% by mass. As a result of the DSC analysis same as that employed in Example 3, in the sample of amphiphilic lipid (three constituent amphiphilic lipids)/water system, $T_K$ was found to decrease as the content of the secondary component increased and $T_K$ was found to be 0° C. or lower when the content of the secondary component became 20% by mass or higher. The results are shown in Table 14.

TABLE 14

| Sample No. | Concentration of secondary component (% by mass) | Temperature at which formation of cubic liquid crystals was observed (° C.) |
| --- | --- | --- |
| 1 | 30 | 1 to 45 (Pn3m cubic liquid crystals) |
| 2 | 50 | 1 to 25 (Pn3m cubic liquid crystals) |

Example 18

Production of Type II Cubic Liquid Crystal Composition Comprising Physiologically Active Substance Embedded Therein Production of Cubic Liquid Crystal Composition of Amphiphilic Compound/Vitamin A/Water System Vitamin A was added to a mixture comprising 20% by mass of 1-O-(3,7,11,15-tetramethylhexadecyl)-α-D-xylopyranoside and 80% by mass of 1-O-(3,7,11,15-tetramethylhexadecyl)-β-D-xylopyranoside in an amount of 5.5% by mass based on the total amount of amphiphilic compound, and they were homogeneously mixed in the same manner as in Example 3 to obtain a homogeneously mixed sample comprising amphiphilic compound/vitamin A/water. The resulting sample of amphiphilic compound/vitamin A/water system was subjected to SAXS analysis in the same manner as in Example 3. Thus, scattering peaks providing the following ratio peculiar to the Ia3d cubic liquid crystals were obtained:
$\sqrt{3}:\sqrt{4}:\sqrt{7}:\sqrt{8}:\sqrt{10}:\sqrt{11}$.

This cubic liquid crystal was stable at least in a temperature range between room temperature (20° C.) and 45° C. Thus, formation of vitamin A-embedded cubic liquid crystals was observed in the composition comprising 1-O-(3,7,11,15-tetramethylhexadecyl)-α-D-xylopyranoside, 1-O-(3,7,11,15-tetramethylhexadecyl)-β-D-xylopyranoside, and vitamin A.

Production of Cubic Liquid Crystal Composition of Amphiphilic Compound/Sodium Hyaluronate/Water System Further, 0.4% by mass of aqueous sodium hyaluronate solution (0.35 g) was homogeneously mixed in a mixture comprising 20% by mass of 1-O-(3,7,11,15-tetramethylhexadecyl)-α-D-xylopyranoside and 80% by mass of 1-O-(3,7,11,15-tetramethylhexadecyl)-β-D-xylopyranoside (0.65 g) described above in the same manner as in Example 3 to obtain a homogeneously mixed sample of amphiphilic compound/sodium hyaluronate/water. The sample of amphiphilic compound/sodium hyaluronate/water system was subjected to SAXS analysis in the same manner as in Example 3. Thus, the scattering results exhibiting the following ratio peculiar to the Pn3m cubic liquid crystals were observed in at least a temperature range between 4° C. and 55° C.:
$\sqrt{2}:\sqrt{3}:\sqrt{4}:\sqrt{6}:\sqrt{8}:\sqrt{9}:,,,.$ This indicates that Pn3m cubic liquid crystals are formed in the sample of amphiphilic compound/sodium hyaluronate/water system.

Production Of Cubic Liquid Crystal Composition Of Amphiphilic Compound/Vitamin E/Water System 522 mg of mono-O-(5,9,13,17-tetramethyloctadecanoyl)pentaerythritol (formula (9) above; PEOCOC22) and 55.4 mg of vitamin E (α-tocopherol) were dissolved in 0.8 ml of dichloromethane, and dichloromethane was then removed under reduced pressure to obtain a mixed sample of mono-O-(5,9,13,17-tetramethyloctadecanoyl)pentaerythritol/vitamin E comprising 9.6% by mass of vitamin E. This amphiphilic compound/vitamin E sample was mixed with water in accordance with the same procedure as in Example 3, the resulting sample was subjected to the penetration experiment under a polarizing microscope at 25° C. in the same manner as in Example 3. A stable and isotropic lipid phase was formed at the interface with water, indicating that formation of the type II liquid crystal phase was confirmed.

Further, the type II liquid crystal sample was subjected to SAXS analysis. 6 sharp scattering peaks were obtained, and the peak value ratio exhibited the following ratio peculiar to the cubic liquid crystals belonging to the crystallographic space group Pn3m:
$\sqrt{2}:\sqrt{3}:\sqrt{4}:\sqrt{6}:\sqrt{8}:\sqrt{9}$.

Thus, formation of type II Pn3m cubic liquid crystals that belong to the crystallographic space group Pn3m and have the lattice constant of 9.05 nm was confirmed in the sample of mono-O-(5,9,13,17-tetramethyloctadecanoyl)pentaerythritol/vitamin E/water system comprising 9.6% by mass of vitamin E.

Production of Cubic Liquid Crystal Composition of Amphiphilic Compound/Chlorophyll a/Water System 2.44 mg of chlorophyll a and 127 mg of pure water were added to a lipid mixture (236 mg) comprising 5% by mass of 1-O-(3,7,11,15-tetramethylhexadecyl)-α-D-xylopyranoside and 95% by mass of 1-O-(3,7,11,15-tetramethylhexadecyl)-β-D-xylopyranoside, and they were homogeneously mixed and then subjected to SAXS analysis in accordance with the same procedures as in Example 3. As a result, formation of Pn3m cubic liquid crystals was confirmed.

Production of Cubic Liquid Crystal Composition of Amphiphilic Compound/Beclomethasone Dipropionate/Water System Beclomethasone dipropionate was added to a mixture comprising 5% by mass of 1-O-(3,7,11,15-tetramethylhexadecyl)-α-D-xylopyranoside and 95% by mass of 1-O-(3,7,11,15-tetramethylhexadecyl)-β-D-xylopyranoside in an amount of 5%, 1%, 0.1%, or 0.02% by mass, based on the total amount of the amphiphilic compound. The resulting mixture was dissolved in dichloromethane, and dichloromethane was removed under reduced pressure to obtain an amphiphilic compound/beclomethasone dipropionate mixture. The resulting mixture was mixed with water in accordance with the same procedure as in Example 3 to obtain a sample of an amphiphilic compound/beclomethasone dipropionate/water system. The sample of amphiphilic compound/beclomethasone dipropionate/water system was subjected to SAXS analysis in the same manner as in Example 3. As a result, scattering peaks providing the following ratio peculiar to cubic liquid crystals that belong to the crystallographic space group Pn3m was obtained:
$\sqrt{2}:\sqrt{3}:\sqrt{4}:\sqrt{6}:\sqrt{8}:\sqrt{9}$.

The cubic liquid crystals were stable at least in a temperature range between room temperature (20° C.) and 45° C. Further, the sample of amphiphilic compound/beclomethasone dipropionate/water system was observed by polarizing microscopy, and precipitation of beclomethasone dipropionate microcrystals within the Pn3m cubic liquid crystals was observed in samples other than those comprising 0.02% by mass of beclomethasone dipropionate. This indicated that the amount of beclomethasone dipropionate soluble in a hydrophobic part of the lipid of the Pn3m cubic liquid crystals was about 0.02% by mass. Also, beclomethasone dipropionate microcrystals were observed only within the Pn3m cubic liquid crystals but were not observed in an outer aqueous phase. Thus, beclomethasone dipropionate was found to be embedded selectively in the Pn3m cubic liquid crystals. In this cubic liquid crystal composition, beclomethasone dipropionate in an amount that exceeds the saturating solubility as shown in the above case is considered to be present within the cubic liquid crystals in the state of a microcrystalline dispersion.

Production of Cubic Liquid Crystal Composition of Amphiphilic Compound/Olive Oil/CoQ10/Water System Coenzyme $Q_{10}$ (hereafter abbreviated as "$CoQ_{10}$") was added to a mixture of 95% by mass of mono-O-(5,9,13,17-tetramethyloctadecanoyl)pentaerythritol (formula (9) above) and 5% by mass of olive oil in an amount of 0.05%, 0.1%, 0.5%, 1%, 2%, 5%, or 20% by mass, and the resultant was heat-melted at 50° C. for 5 minutes, followed by homogeneous mixing to obtain a mixed sample of mono-O-(5,9,13,17-tetramethyloctadecanoyl)pentaerythritol/olive oil/$CoQ_{10}$. The sample of amphiphilic compound/olive oil/$CoQ_{10}$ was mixed with water in accordance with the same procedure as in Example 3 to prepare a sample of an amphiphilic compound/olive oil/$CoQ_{10}$/water system, and the obtained sample was subjected to SAXS analysis. As a result, 6 scattering peaks providing the following ratio peculiar to the cubic liquid crystals that belong to the crystallographic space group Pn3m were obtained:
$\sqrt{2}:\sqrt{3}:\sqrt{4}:\sqrt{6}:\sqrt{8}:\sqrt{9}$, thereby formation of Pn3m cubic liquid crystals was confirmed. The lattice constant was 9.7 nm (25° C.) at any $CoQ_{10}$ concentration.

The sample of amphiphilic compound/$CoQ_{10}$/water system was observed by polarizing microscopy. A sample containing 0.5% by mass or more $CoQ_{10}$ was found to comprise $CoQ_{10}$ dispersed within the Pn3m cubic liquid crystals as microcrystals (or solids). In contrast, $CoQ_{10}$ microcrystals within the Pn3m cubic liquid crystals could not be observed in a sample containing 0.1% by mass or less $CoQ_{10}$. Since $CoQ_{10}$ microcrystals were observed only within the Pn3m cubic liquid crystals but were not observed in the outer aqueous phase, $CoQ_{10}$ was concluded to be embedded selectively within the Pn3m cubic liquid crystals. Thus, the maximal concentration of $CoQ_{10}$ (saturating solubility) molecularly solubilized in the hydrophobic part of the lipid of the Pn3m cubic liquid crystals was found to be about 0.05 to 0.1% by mass and $CoQ_{10}$ in an amount exceeding the saturating solubility was found to be dispersed as microcrystals within the cubic liquid crystals in the sample of mono-O-(5,9,13,17-tetramethyloctadecanoyl)pentaerythritol/olive oil/$CoQ_{10}$/water system. The Pn3m cubic liquid crystals in which $CoQ_{10}$ had been embedded were stable at least in a temperature range between 1° C. and 40° C.

Example 19

Production of Type II Cubic Liquid Crystals Comprising Enzymes Embedded Therein

40 µl of 230 mg/ml aqueous lysozyme solution was added to 40.2 mg of a lipid mixture comprising 20% by mass of 1-O-(3,7,11,15-tetramethylhexadecyl)-α-D-xylopyranoside and 80% by mass of 1-O-(3,7,11,15-tetramethylhexadecyl)-β-D-xylopyranoside, the resultant was homogeneously mixed in accordance with the same procedure as in Example 3, and the mixture was incubated at 15° C. for 10 hours to obtain a sample of an amphiphilic compound/lysozyme/water system. This sample was subjected to SAXS analysis. As a result, scattering results exhibiting the following ratio peculiar to the Im3m cubic liquid crystals were obtained in a temperature range between 15° C. and 65° C.:

$\sqrt{2}:\sqrt{4}:\sqrt{6}:\sqrt{8}:\sqrt{10}$.

This indicates that Im3m cubic liquid crystals are formed in the sample of amphiphilic compound/lysozyme/water system. This system also comprised as much as 23% by mass of lysozyme based on the total amount of the amphiphilic compound. Thus, this cubic liquid crystal was found to be capable of incorporating a large quantity of proteins.

Further, 35 µl of 0.1% by mass aqueous casein solution was added to 65 mg of the amphiphilic compound mixture system as described above, and the resultant was homogeneously mixed in accordance with the same procedure as in Example 3. Using the same procedure as with Example 3, formation of Pn3m cubic liquid crystals in the obtained sample of amphiphilic compound/casein/water system was confirmed.

Example 20

Production of Type II Cubic Liquid Crystals Comprising Peptides Embedded Therein and Ability for Controlled Release Thereof Mono-O-(phytanyl)pentaerythritol (75 mg) was blended with 25 ml of an insulin injection solution (Penfill R) containing 100 unit/ml of insulin in accordance with the same procedure as in Example 3. The thus obtained sample of mono-O-(phytanyl)pentaerythritol/insulin/water system was subjected to SAXS analysis in the same manner as in Example 3. Thus, formation of Pn3m cubic liquid crystals was exhibited.

Figure 10:
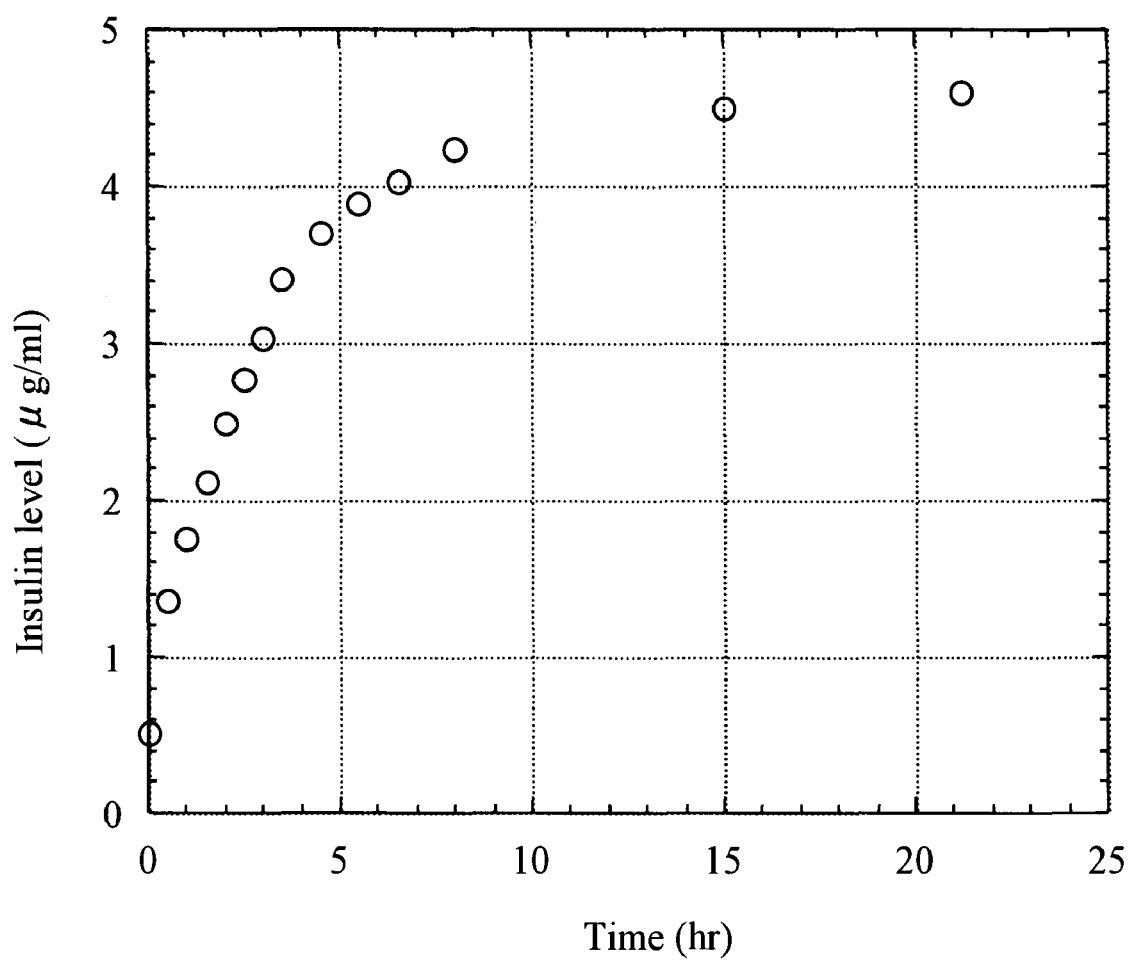
FIG. 10 shows the results of a test of the ability for controlled-release of insulin embedded in cubic liquid crystals.

Subsequently, the sample of mono-O-(phytanyl)pentaerythritol/insulin/water system (i.e., a cubic liquid crystal composition-insulin complex) was shaped in the form of a rod with a diameter of 0.3 mm, and 50 mg thereof was immersed in 10 ml of physiological saline. After immersion, the amount of insulin eluted in physiological saline at 37° C. was measured over time by high-performance liquid chromatography. This indicated that all insulin embedded in the cubic liquid crystal structure was control-released over the period of about 8 to 10 hours (FIG. 10).

Reference Example 2

Test of the Ability for Controlled Release of Cubic Liquid Crystals Comprising Enzymes Embedded Therein α-Galactosidase (α-GALA) and β-galactosidase (β-GAL) were separately dissolved in phosphate buffered saline (PBS) to bring the enzyme concentration to 1 mg/ml. Subsequently, the α-GALA or β-GAL solution was added to 1-O-(3,7,11, 15-tetramethylhexadecyl)-β-D-xylopyranoside (abbreviated as "β-XP") at 35:65 by mass, and the mixture was thoroughly mixed to prepare a β-XP cubic liquid crystal composition comprising α-GALA or β-GAL embedded therein.

Enzyme activities of α-GALA and β-GAL embedded in the cubic liquid crystals were detected by the reaction with 4-methylumbelliferyl-α-D-galactopyranoside as a substrate for α-GALA and 4-methylumbelliferyl-β-D-galactopyranoside as a substrate for β-GAL and the observation of the reaction product, i.e., 4-methylumbelliferone, by fluorescence microscopy.

At the outset, about 1 mg of a cubic liquid crystal composition comprising α-GALA or β-GAL embedded therein was placed on a glass slide, the glass slide was covered by a glass cover, and the composition was allowed to spread while applying light pressure. A substrate solution (10 µl, 1.7 mg/ml) comprising the aforementioned substrate dissolved in a 0.15M sodium acetate solution (pH 4.6) was added thereto, and the resultant was then observed under a fluorescence microscope with time.

Figure 11:
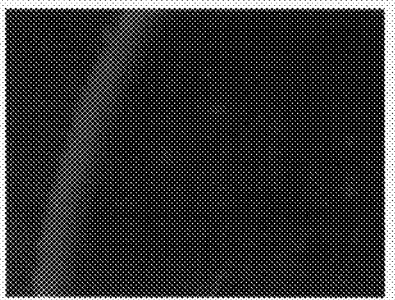
FIG. 11 is a photograph showing that α-galactosidase (α-GALA) and β-galactosidase (β-GAL) embedded in cubic liquid crystals are active.
Figure 11:
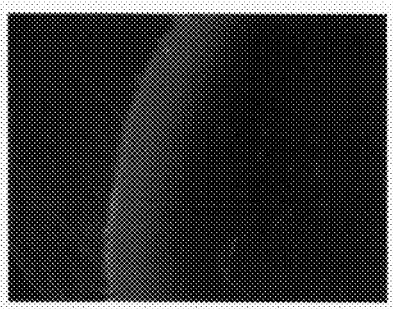
Figure 11:
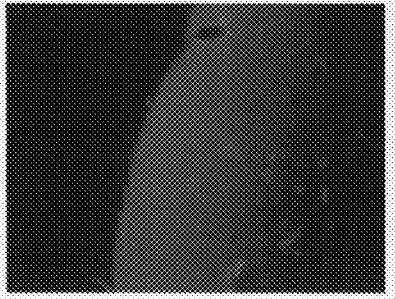
Figure 11:
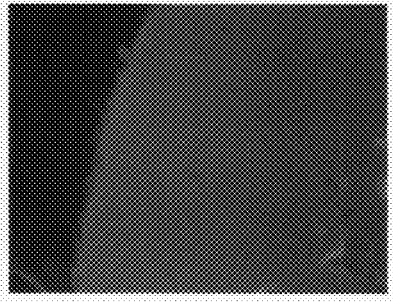
Figure 11:
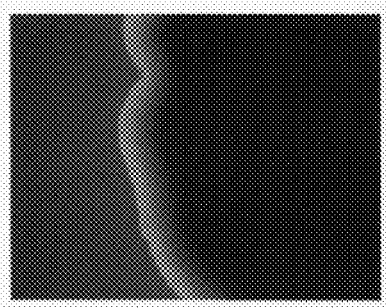
Figure 11:
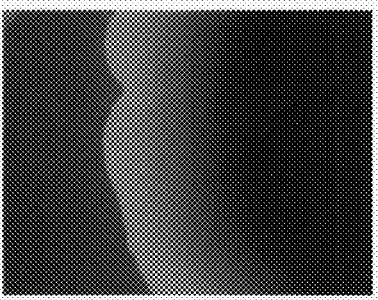
Figure 11:
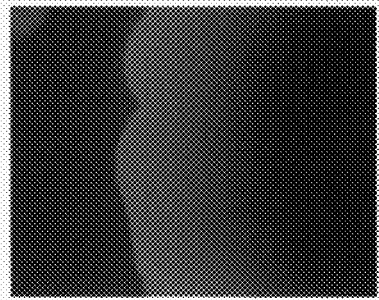
Figure 11:
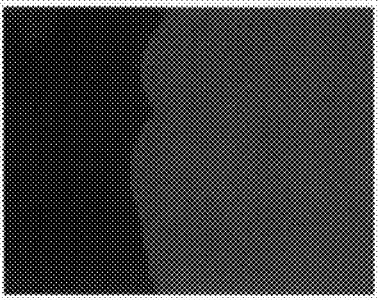

As a result of observation, fluorescence from the reaction product was observed within the crystals of the cubic liquid crystal composition comprising α-GALA or β-GAL embedded therein (FIG. 11). This indicates that the embedded α-GALA or β-GAL had activity within the cubic liquid crystals. α-GALA having a molecular weight of 48,000 is known to form a dimer as a functional form and β-GAL having a molecular weight of 116,400 is known to form a tetramer as a functional form. This indicates that the cubic liquid crystals of the Example are capable of embedding proteins having molecular weights of 96,000 to 465,600 while maintaining their activities.

Further, ability for controlled release of α-GALA embedded in the cubic liquid crystals was inspected. In order to realize an experimental system on the assumption that controlled release is intended in the blood, 10 mg of the cubic liquid crystal composition comprising α-GALA (enzyme concentration: 2 mg/ml, 0.2 mg/ml) embedded therein that had been produced in the same manner as described above was added to 1 ml of bovine serum, and the resultant was shaken in an incubator at 10° C. Samples were obtained (10 µl each) 0, 2, 6, 24, and 48 hours after the initiation of shaking for assaying α-GALA activities.

For detection of α-GALA activities, 60 μl of a substrate solution of 4-methylumbelliferyl-α-D-galactopyranoside (26 mg/ml) was added to 10 μl of the obtained sample to react them, the reaction was allowed to proceed at 37° C. for 30 minutes, and 700 μl of a 0.2M glycine (pH 10.7)-NaOH solution was added thereto to terminate the reaction. The reaction product, 4-methylumbelliferone, was assayed at an excitation wavelength of 365 nm and a fluorescence wavelength of 450 nm using a fluorescence spectrometer. FIGS. 12A and B show the results of a test of the ability for controlled release of the cubic liquid crystal compositions comprising α-GALA at 2 mg/ml and 0.2 mg/ml, respectively, embedded therein.

Figure 12:
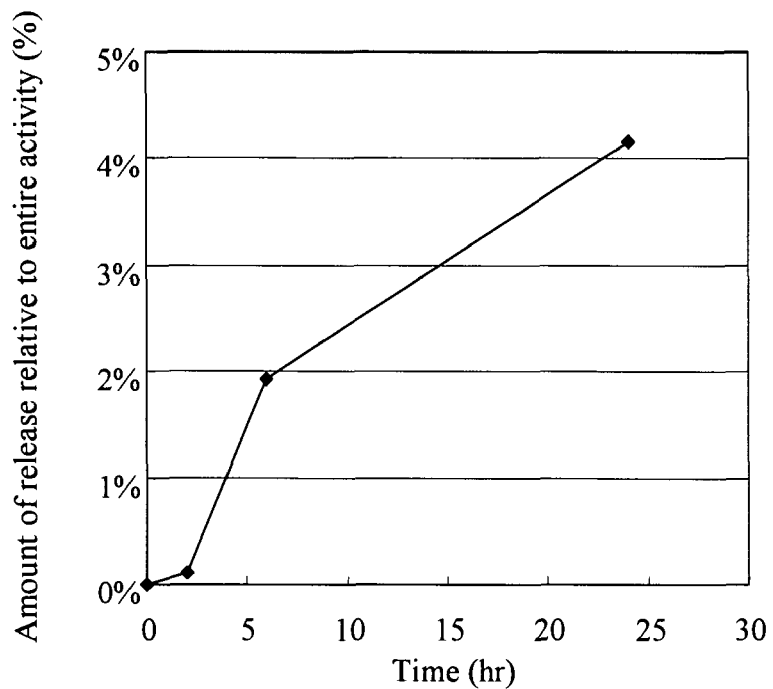
FIG. 12 shows the results of a test of the ability for controlled-release of the cubic liquid crystal composition comprising α-GALA embedded therein.
Figure 12:
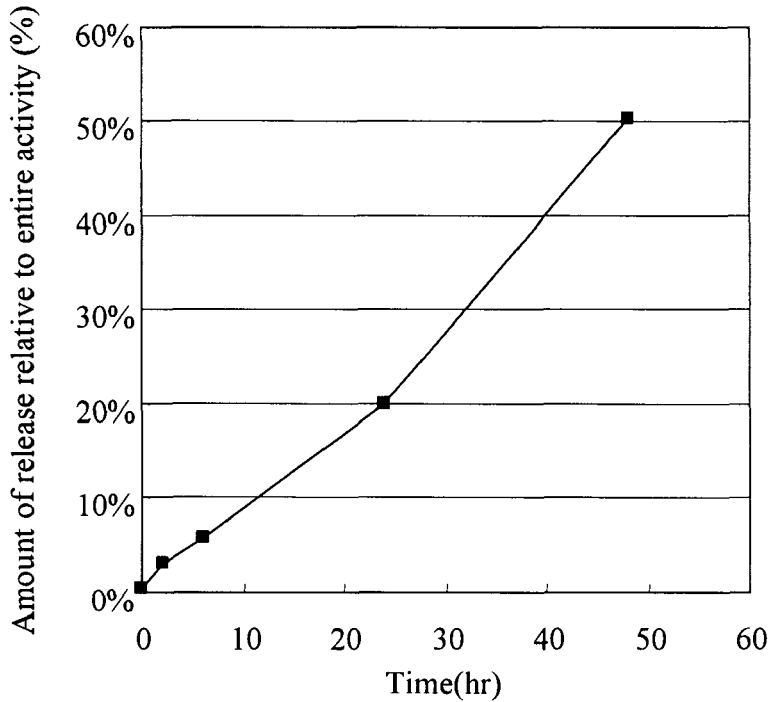

As shown in FIG. 12, in the cubic liquid crystal composition comprising 2 mg/ml of α-GALA embedded therein, α-GALA activity was gradually increased immediately after the initiation of shaking and enzyme activity equivalent to about 4% of the amount thereof embedded was exhibited 24 hours thereafter. Also, in the cubic liquid crystal composition comprising 0.2 mg/ml of α-GALA embedded therein, α-GALA activity was gradually increased immediately after the initiation of shaking and enzyme activity equivalent to about 50% of the amount thereof embedded was exhibited 48 hours thereafter.

Reference Example 3

Kinetics in Blood of Mice to which Enzyme-Embedded Cubic Liquid Crystals have been Administered The cubic liquid crystal compositions comprising α-GALA embedded therein produced in the same manner as in Reference Example 2 (30 mg per mouse) were intraperitoneally administered to 9 groups of 9-week-old male mice (Slc:ICR(SPF) line) (each group consisting of 3 mice). Blood (at least 0.4 ml) was sampled through the abdominal aortas from one group of mice among the 9 groups under ether anesthesia 0, 2, 4, 6, 12, 24, 32, 48, and 72 hours after the administration. As the controls, a solution containing α-GALA diluted with physiological saline was intraperitoneally administered to mice of the same lineage instead of the cubic liquid crystal composition, and blood sampling was performed 2, 6, and 24 hours after the administration.

Figure 13:
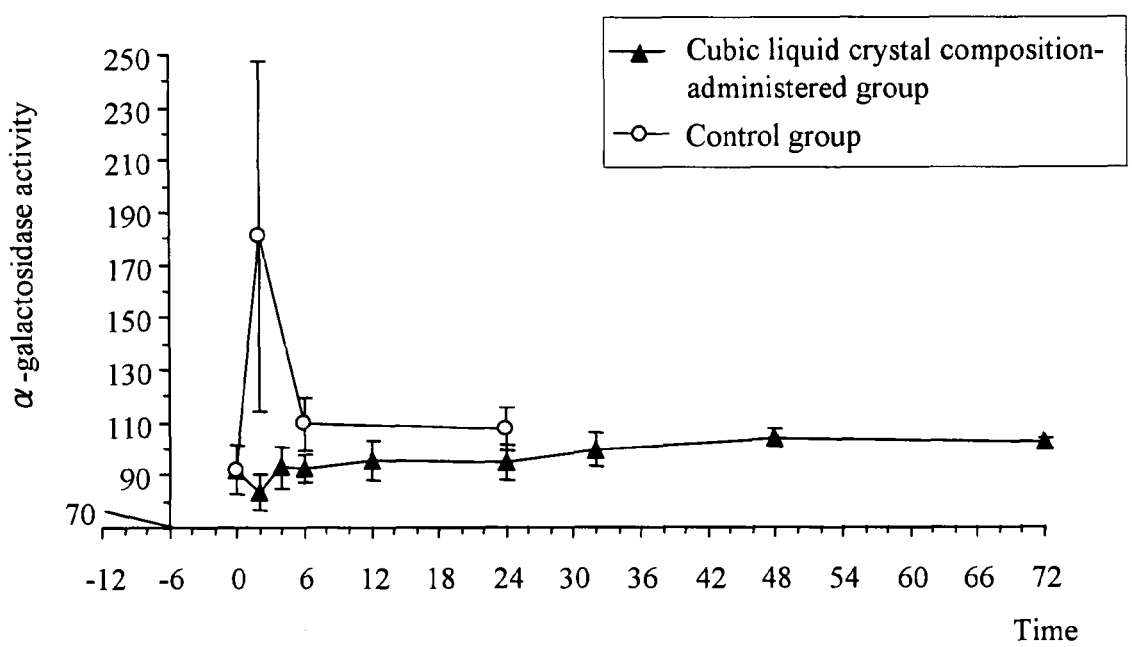
FIG. 13 shows changes in α-GALA activity in the blood of a mouse to which a cubic liquid crystal composition comprising α-GALA embedded therein has been administered.

The sampled blood was placed in ice water immediately thereafter, allowed to stand therein for 30 minutes or longer, and centrifuged at 3,000 rpm for 15 minutes. The supernatant (serum) was divided into two equivalent fractions and stored at −20° C. until the next test. A substrate solution of 4-methylumbelliferyl-α-D-galactopyranoside (60 μl) was added to 10 μl of the serum, the reaction was allowed to proceed at 37° C. for 30 minutes, and 700 μl of a 0.2M glycine (pH 10.7)-NaOH solution was added thereto to terminate the reaction. The reaction product, 4-methylumbelliferone, was assayed at an excitation wavelength of 365 nm and a fluorescence wavelength of 450 nm using a fluorescence spectrometer. The results are shown in FIG. 13. In FIG. 13, a closed triangle (▲) represents a group to which the cubic liquid crystal composition is administered and a open circle (○) represents a group to which a control sample is administered.

As a result, α-GALA activity was found to be increased 12 hours after the administration in the blood of a mouse to which the cubic liquid crystal composition comprising α-GALA embedded therein has been administered. The α-GALA activity reached the peak 48 hours after the administration and it was maintained at the same level 72 hours after the administration. At the peak, an increase in the activity was about 113% based on the activity immediately before the administration (0 hours). In the blood of a mouse to which a control sample had been administered, the α-GALA activity reached the peak 6 hours after the administration (about 197% of the activity immediately before the administration) and it was drastically decreased 12 hours after the administration.

When α-GALA is administered through the cubic liquid crystal composition comprising α-GALA embedded therein, rapid increase in the blood α-GALA level is inhibited immediately after the administration. Thus, side effects resulting from rapid increase of the blood α-GALA level can be inhibited. Since the blood α-GALA level can be maintained at a constant level for a long period of time, lowering in administration frequency and improvement in a patient's QOL can be expected.

Example 21

Functionality Testing for Cosmetic Products

Superoxide dismutase (300 units, abbreviated as "SOD") was dissolved in 1 ml of 0.1M phosphate buffer (pH 7.0), and 12 μl thereof was mixed with 35.5 mg of a mixture of 1-O-(3,7,11,15-tetramethylhexadecyl)-α-D-xylopyranoside (20%) and 1-O-(3,7,11,15-tetramethylhexadecyl)-β-D-xylopyranoside (80%) to obtain a transparent and gel, cubic liquid crystal composition containing SOD. The resultant was thinly coated on the surface of an electrode on which cytochrome C had been immobilized.

Subsequently, two types of electrodes, i.e., the cytochrome C-immobilized electrode has been coated with the gelatinous SOD-containing cubic liquid crystal composition and a cytochrome C-immobilized electrode (without coating), were immersed in 0.1M phosphate buffer (pH 7.0) containing 0.5 mM xanthine, and xanthine oxidase was added to generate superoxide radicals. On the cytochrome C-immobilized electrode, an electric current was generated from the electron transfer between superoxide radicals and cytochrome C immobilized on the electrode surface. On the cytochrome C-immobilized electrode coated with a gelatinous SOD-containing cubic liquid crystal composition, a small electric current as small as about 1/10 of that on the chytochrome C-immobilized electrode was obtained. This indicates that superoxide radicals generated in the solution were degraded by SOD present in the cubic liquid crystals. This indicates that use of an SOD-containing cubic liquid crystal composition as an active ingredient enables the preparation of antioxidant cosmetic products.

It is known that hydrogen peroxide is generated upon degradation of superoxide radical by SOD. Thus, a cubic liquid crystal composition (in gel form) comprising two types of enzymes, i.e., SOD and catalase, was prepared and the experiment was performed in accordance with the method described above. As a result, generation of hydrogen peroxide was remarkably inhibited. Accordingly, use of a cubic liquid crystal composition comprising two enzymes, SOD and catalase, as active ingredients enables the production of cosmetic products having higher antioxidaive effects. For example, a cubic liquid crystal composition comprising two enzymes, SOD and catalase, can be used to produce a functional cream for preventing skin aging or the like.

Example 22

Production of Skin-Beautifying Emulsion

Superoxide dismutase (300 units) was dissolved in 1 ml of 0.1M phosphate buffer (pH 7.0), and 3 g of a mixture of 1-O-(3,7,11,15-tetramethylhexadecyl)-α-D-xylopyranoside and 1-O-(3,7,11,15-tetramethylhexadecyl)-β-D-xylopyranoside (20%:80% by mass) was added thereto and mixed to obtain a transparent and gel, cubic liquid crystal composition containing SOD. To the resulting cubic liquid crystal composition, 0.3 g of Pluronic F127 ((PEG)99-(PPO)67-(PEO)99), 5 g of glycerine, and water (up to 100 g in total mass of the mixture) were added and mixed, and the mixture was agitated using a magnetic stirrer for 3 to 5 hours to obtain an opalescent solution. The resulting solution was a dispersion of cubic liquid crystals comprising fine cubic liquid crystal particles with average particle diameters of 300 to 500 nm. Such dispersion can be used as a skin-beautifying emulsion that can remain stable for 10 months or longer at room temperature.

Example 23

Production of Skin-Beautifying Cream

Superoxide dismutase (300 units) was dissolved in 1 ml of 0.1M phosphate buffer (pH 7.0), and 3 g of a mixture of 1-O-(3,7,11,15-tetramethylhexadecyl)-α-D-xylopyranoside and 1-O-(3,7,11,15-tetramethylhexadecyl)-β-D-xylopyranoside (20%:80% by mass) was added thereto and mixed to obtain a transparent and gel, cubic liquid crystal composition containing SOD. To the resulting cubic liquid crystal composition, 0.3 g of Pluronic F127 ((PEG)99-(PPO)67-(PEO)99) and water (up to 15 g in total mass of the mixture) were added, and the mixture was agitated to obtain an opalescent dispersion of cubic liquid crystals. The resulting dispersion can be used as a skin-beautifying cream.

Example 24

Effects of a Cubic Liquid Crystal Composition of Amphiphilic Compound/Sodium Hyaluronate/Water System for Inhibiting Evaporation of Moisture The cubic liquid crystal composition of amphiphilic compound/sodium hyaluronate/water system prepared in Example 18 (a test sample) and 0.4% by mass of aqueous sodium hyaluronate solution (a control sample) were introduced into separate PCR tubes, stored under a nitrogen gas stream at 25° C. and having 30% relative humidity while keeping the tube caps open, and the amounts of moisture evaporated were measured based on a decrease in a mass of the sample.

As a result, the moisture contents of both samples were found to linearly decrease with the elapse of time. In the case of 0.4% by mass of aqueous sodium hyaluronate solution, the moisture content at the time point 8 hours after the initiation of evaporation was decreased to as low as 20% that at the beginning of evaporation. In contrast, the cubic liquid crystal composition of the amphiphilic compound/sodium hyaluronate/water system (containing 0.4% by mass of aqueous sodium hyaluronate solution) retained 60% of the moisture content 8 hours after the initiation of evaporation. In the cubic liquid crystal composition of amphiphilic compound/sodium hyaluronate/water system, the rate of moisture evaporation was inhibited compared with that in the sample of 0.4% by mass of aqueous sodium hyaluronate solution alone. Thus, the excellent capacity of the cubic liquid crystal composition containing an aqueous sodium hyaluronate solution for retaining moisture was confirmed.

Example 25

Stabilization of Cubic Liquid Crystals

When a certain type of third component is added, for example, the structures of cubic liquid crystals may be transformed into those of lamellar liquid crystals or type II (inverted) hexagonal liquid crystals (HII). In such a case, a curvature-regulating substance (in particular a curvature-modifying lipid) such as olive oil may be added to inhibit transformation of the liquid crystal structure and to maintain the cubic liquid crystal structure.

Pluronic F127 was added to mono-O-(5,9,13,17-tetramethyloctadecanoyl)pentaerythritol in an amount corresponding to a mass ratio of 0.11 to obtain a mixed sample of mono-O-(5,9,13,17-tetramethyloctadecanoyl)pentaerythritol/Pluronic F 127 (Pluronic F127/mono-O-(5,9,13,17-tetramethyloctadecanoyl)pentaerythritol=0.11 (w/w)). This mixed sample was mixed with water in accordance with the same procedure as in Example 3 to obtain a sample of a mono-O-(5,9,13,17-tetramethyloctadecanoyl)pentaerythritol/Pluronic F127/water system. This sample was subjected to SAXS analysis in the same manner as in Example 3. As a result, strong scattering peaks derived from lamellar liquid crystals (a repeating cycle of lamellar=4.7 nm, 1° C.) (scattering peak ratio=1:1/2) and weak scattering peaks deduced to be derived from Im3m cubic liquid crystals were observed. Due to poor resolution, the lattice constant or the like could not be determined. The above results indicate that the cubic liquid crystals of mono-O-(5,9,13,17-tetramethyloctadecanoyl)pentaerythritol/water system was transformed into lamellar liquid crystals in the presence of Pluronic F127.

Next, 5% by mass of olive oil was added to mono-O-(5,9,13,17-tetramethyloctadecanoyl)pentaerythritol, Pluronic F127 was added thereto in the same manner as described above, and the resultant was mixed with water in accordance with the same procedure as in Example 3 to obtain a sample of a mono-O-(5,9,13,17-tetramethyloctadecanoyl)pentaerythritol/olive oil/Pluronic F127/water system. This sample was subjected to SAXS analysis in the same manner as in Example 3. As a result, scattering derived from lamellar liquid crystals was not observed but scattering exhibiting a peak ratio peculiar to Im3m cubic liquid crystals was observed. Thus, formation of Im3m cubic liquid crystals (lattice constant=13.2 nm) was confirmed. This indicates that the above samples which generates lamellar liquid crystals with the addition of Pluronic F127 are stabilized so as to maintain the Im3m cubic liquid crystal structure with the addition of olive oil.

Example 26

Protein Crystallization Using Cubic Liquid Crystal Composition

A solution of 0.4M NaCl, 0.075M sodium acetate and 100 mg/ml of lysozyme (pH 4.6) and a solution of 0.4M NaCl, 0.075M sodium acetate and 50 mg/ml of lysozyme (pH 4.6) were prepared and filtered through a 0.1-μm filter.

As the amphiphilic compounds of the present invention, the following 3 types of amphiphilic compounds were employed: (A) 1-O-(3,7,11,15-tetramethylhexadecyl)-D-xylopyranoside comprising 66% by mass of 1-O-(3,7,11,15-tetramethylhexadecyl)-α-D-xylopyranoside and 34% by mass of 1-O-(3,7,11,15-tetramethylhexadecyl)-β-D-xylopyranoside (hereafter referred to as "αβ-XP"); (B) 1-O-(5,9,13,17-tetramethyloctadecanoyl)erythritol; and (C) 1-O-(3,7,11,15-tetramethylhexadecyl)-β-D-xylopyranoside (hereafter referred to as "β-XP"). Fractions of such amphiphilic compounds (50 mg each) were weighed and introduced into separate PCR tubes. Thereafter, 50 mg of the solution of 0.4M NaCl, 0.075M sodium acetate and 100 mg/ml or 50 mg/ml of lysozyme (pH 4.6) was added thereto, and the resultant was thoroughly mixed in the PCR tube. After centrifugation at 13,000 rpm and 25° C. for 10 minutes, 10 mg each of the samples was used to form thin-film spots (diameter: 1 mm; thickness: about 30 microns) on glass slides, followed by polarizing microscopic observation. As a result, the samples exhibited to be optically isotropic, and thereby formation of cubic liquid crystals was confirmed. In this example, 0.4M NaCl was used as a crystallizing agent.

Subsequently, the spots comprised of lysozyme-containing cubic liquid crystal compositions were allowed to stand in sealed containers in which saturation equilibrium has been established at the water vapor pressure with a solution of 0.4M NaCl, 0.075 M sodium acetate (pH 4.6), a sample employing αβ-XP or 1-O-(5,9,13,17-tetramethyloctadecanoyl)erythritol was incubated at 4° C., and a sample employing β-XP was incubated at 20° C.

In the sample containing 1-O-(5,9,13,17-tetramethyloctadecanoyl)erythritol that had been incubated at 4° C., formation of lysozyme crystals was observed within the cubic liquid crystal structure 2 days after the initiation of incubation via polarizing microscopy. In the case of the above sample employing the solution containing lysozyme at 100 mg/ml, numerous lysozyme crystals of 20×15 microns to 250×100 microns were observed. In the case of the above sample employing the solution containing lysozyme at 50 mg/ml, however, lysozyme crystals of 20×15 microns to 50×50 microns at a maximum were observed.

Figure 14:
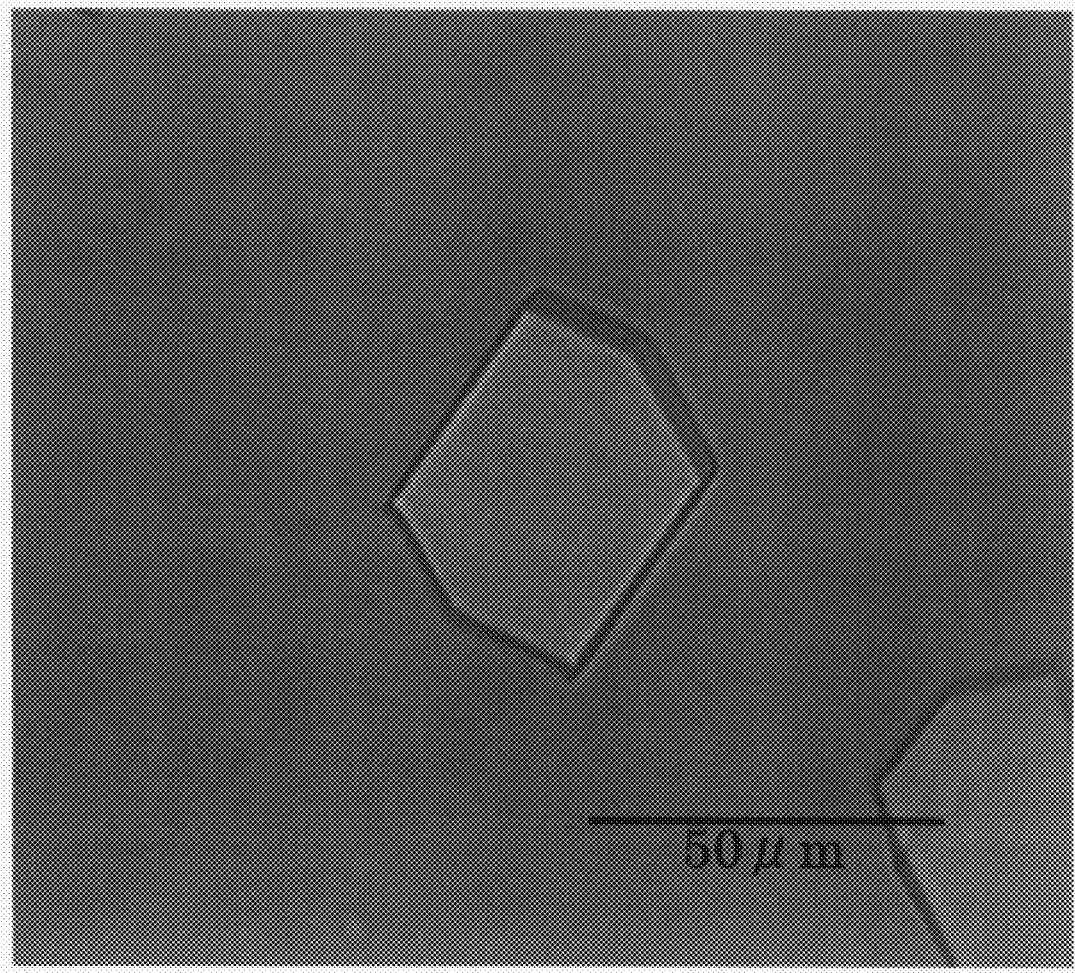
FIG. 14 is a polarizing microscopic photograph showing lysozyme crystals generated within cubic liquid crystals of 1-O-(5,9,13,17-tetramethyloctadecanoyl)erythritol/100 mg lysozyme/ml of 0.4M NaCl, 0.075M sodium acetate solution (pH 4.6) system (horizontal scale: 50 μm).

FIG. 14 shows a polarizing microscopic photograph of one lysozyme crystal grown and prepared within cubic liquid crystals in accordance with the above procedures. As shown in FIG. 14, the obtained lysozyme crystals were birefringent crystals and had polygons with clear edges.

In the αβ-XP-containing sample that had been incubated at 4° C., similarly, growth of lysozyme crystals was observed within the cubic liquid crystal structure 2 days after the initiation of incubation via polarizing microscopy.

The aforementioned incubation at 4° C. was continued for an additional 3 months. During such incubation period, all samples maintained optically isotropic properties. Thus, the cubic liquid crystals were confirmed to be stably maintained at 4° C. for a long period of time in the lysozyme/cubic liquid crystal system.

Also, generation of lysozyme crystals was observed in the β-XP-containing sample that had been incubated at 20° C. This indicates that the cubic liquid crystal structure could be stably maintained for a long period of time at 20° C.

As a control experiment, a sample of an amphiphilic compound (αβ-XP or 1-O-(5,9,13,17-tetramethyloctadecanoyl) erythritol)/0.4M NaCl/0.075 sodium acetate solution (pH 4.6) was prepared under the same conditions as described above except that such sample did not contain lysozyme. The control sample was also subjected to incubation at 4° C. for 3 months. During such incubation period, polarizing microscopic observation was continuously performed. As a result, crystals as observed in the experiments above were not observed within all cubic crystal regions that had been generated.

INDUSTRIAL APPLICABILITY

The cubic liquid crystal composition of the present invention can incorporate various compounds, in particular macromolecular compounds such as enzymes, into liquid crystal structures at low temperatures (lower than 6° C.) and can stably maintain them for a long period of time. Also, the cubic liquid crystal composition of the present invention retains physiologically active substances such as enzymes in the liquid crystal structure to protect them from destruction by degrading enzymes or the like. Thus, such composition can maintain activity of such substances for a period of time longer than that when such substances are freely present in a solution and can allow such substances to control-released from the liquid crystal structure. Thus, the cubic liquid crystal composition of the present invention can be particularly effectively used as a drug delivery carrier in the production of pharmaceutical products.

Further, the method of adapting a cubic liquid crystal structure to a drug delivery system by mixing two or more types of the amphiphilic lipids of the present invention can be employed for producing a cubic liquid crystal composition that is optimized for embedding various compounds having various properties or sizes. Furthermore, a pharmaceutical composition and a cosmetic composition comprising complexes of the type II cubic liquid crystal composition of the present invention with various agents can be used for allowing a drug, as an active ingredient, to act for a long period of time via a single administration, for maintaining a concentration of a drug at a constant level in the blood, or for storing a drug at low temperatures (lower than 6° C.), for example.

Further, the method for crystallizing proteins within the cubic liquid crystal composition of the present invention can be employed for providing protein crystals of high quality that are required for X-ray analysis of proteins or the like.

All publications, patents, and patent applications cited herein are incorporated herein by reference in their entirety.

The invention claimed is:

1. A cubic liquid crystal composition comprising at least one amphiphilic compound and water or an aqueous medium, wherein said amphiphilic compound is at least one selected from the group consisting of following formulae (2) to (12) and (15):

(2)

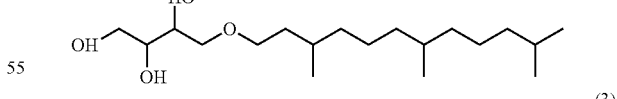

(3)

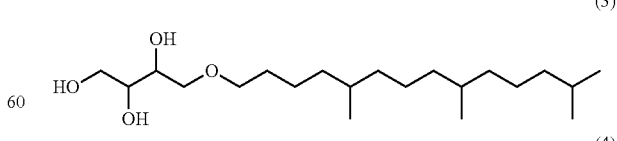

(4)

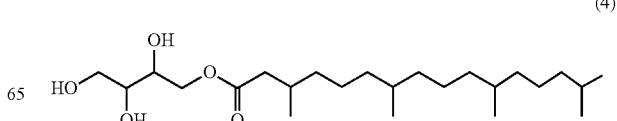

-continued

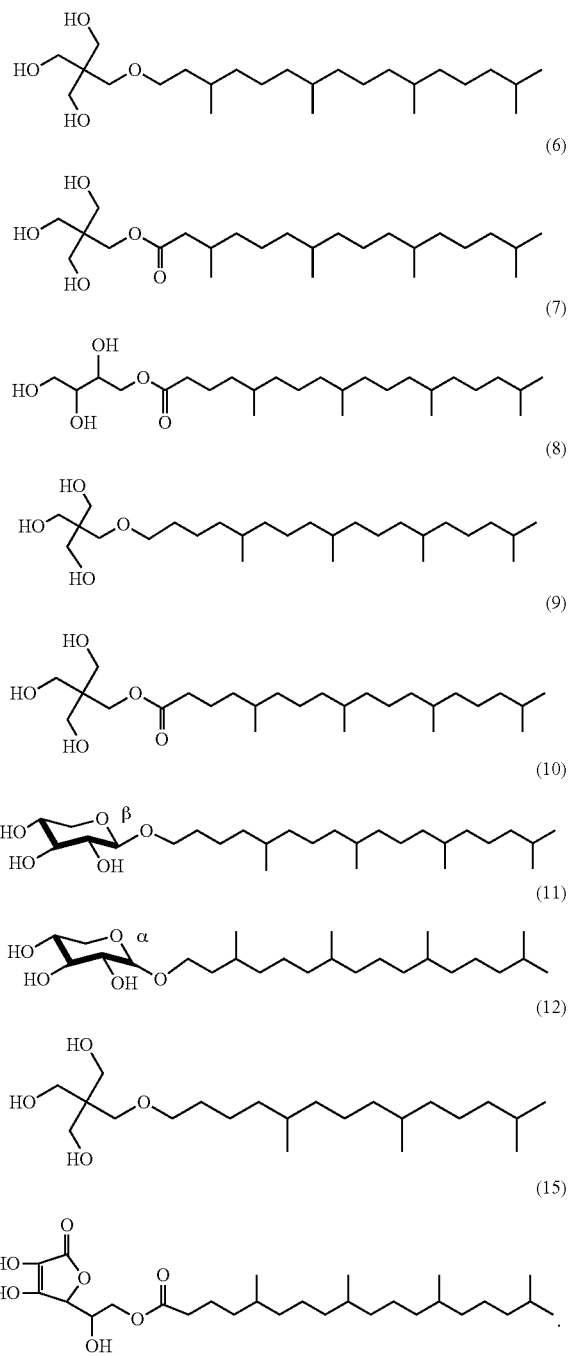

2. The cubic liquid crystal composition according to claim 1, which further comprises at least one amphiphilic lipid different from said amphiphilic compound.

3. The cubic liquid crystal composition according to claim 1, which further comprises at least one amphiphilic lipid different from said amphiphilic compounds having formulae (2) to (12) and (15).

4. A complex comprising a drug embedded in the cubic liquid crystal composition according to claim 1, wherein the drug is not a lysosomal enzyme.

5. A pharmaceutical composition comprising the complex according to claim 4.

6. The composition according to claim 5, which is a controlled release composition.

7. A complex comprising an active cosmetic ingredient embedded in the cubic liquid crystal composition according to claim 1, wherein the drug is not a lysosomal enzyme.

8. A cosmetic composition comprising the complex according to claim 7.

9. The cubic liquid crystal composition according to claim 1, wherein said amphiphilic compound is at least one selected from the group consisting of said formulae (2) to (10), (12) and (15).

10. The cubic liquid crystal composition according to claim 2, wherein said amphiphilic compound is a compound of said formulae (11) and wherein said at least one amphiphilic lipid is selected from the group consisting of monoolein, monovaccenin, 3,7,11,15-tetramethylhexadecyl-1,2,3-triol, the compound of formulae (13), and the compound of formulae (14).

11. The cubic liquid crystal composition according to claim 10, wherein said amphiphilic compound is a compound of said formula (11) and wherein said at least one amphiphilic lipid is the compound of formulae (13).

12. The cubic liquid crystal composition according to claim 3, wherein said amphiphilic compound is a compound of said formula (5) and wherein said at least one amphiphilic lipid is the compound of formulae (13).

13. The cubic liquid crystal composition according to claim 10, wherein said amphiphilic compound is a compound of said formulae (11) and wherein said at least one amphiphilic lipid is selected from the group consisting of the compound of formulae (13) and the compound of formulae (14).

14. An amphiphilic compound having any of following formulae (2) to (10), (12), and (15):

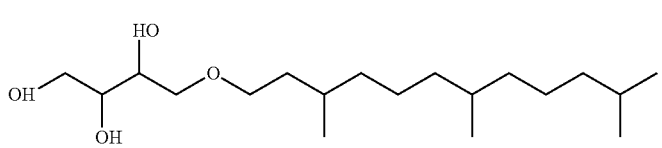

(2)

-continued
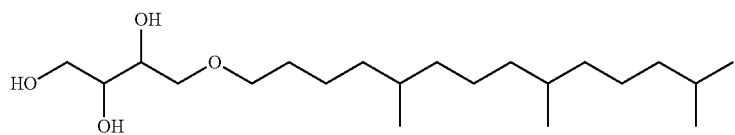
(3)
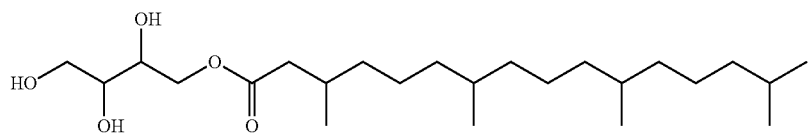
(4)
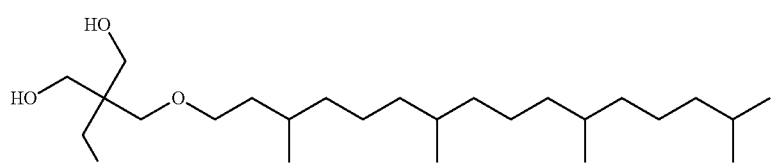
(5)
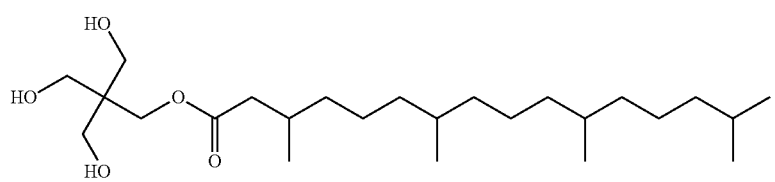
(6)
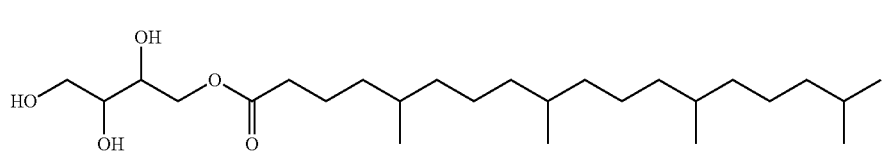
(7)
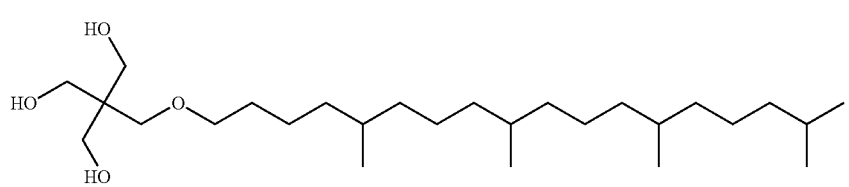
(8)
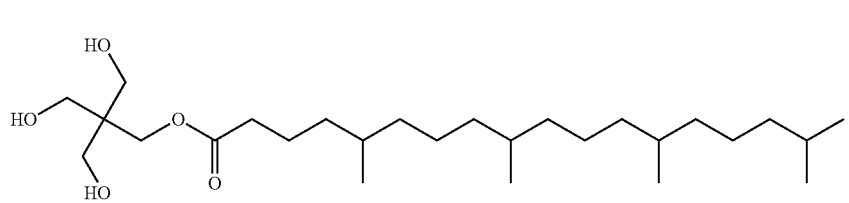
(9)
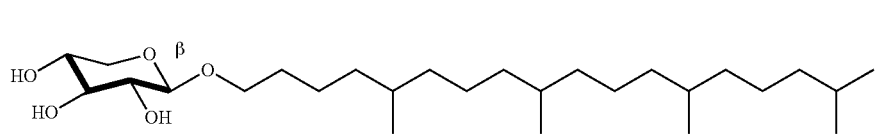
(10)
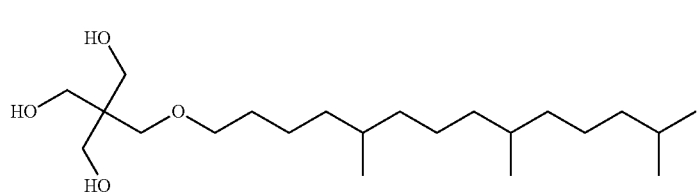
(12)

-continued

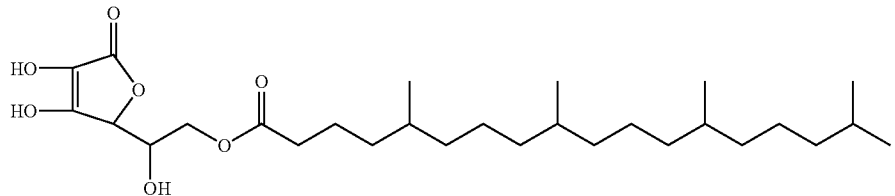
(15)

15. A method for modifying a liquid crystal structure and physical properties of a cubic liquid crystal composition comprising adding at least one amphiphilic lipid different from compounds having formulae (2) to (12) and (15) to at least one amphiphilic compound selected from the group consisting of compounds having following formulae (2) to (12) and (15) and mixing them in water or an aqueous medium:

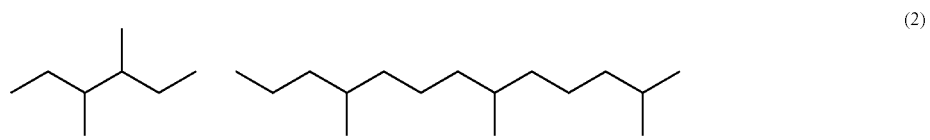
(2)

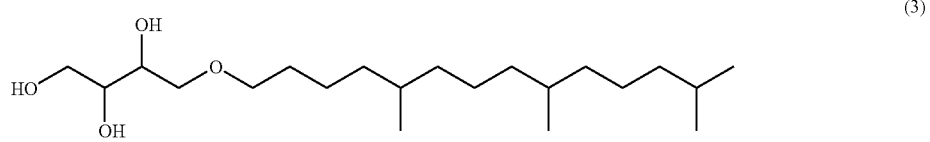
(3)

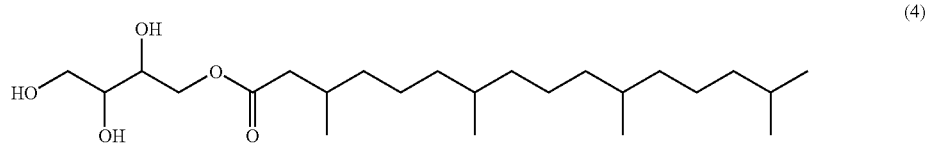
(4)

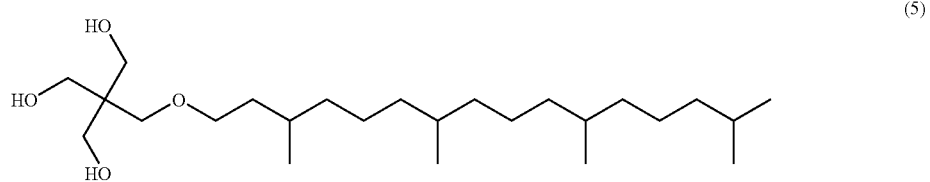
(5)

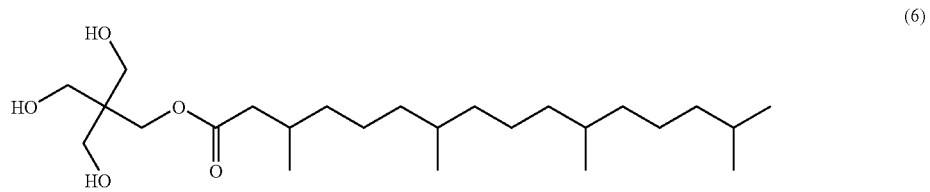
(6)

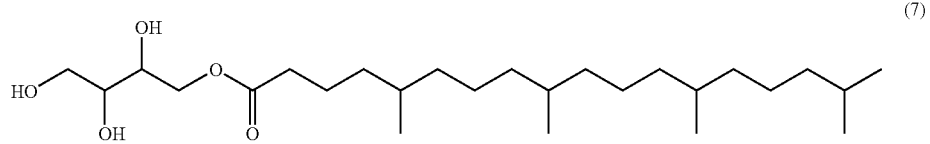
(7)

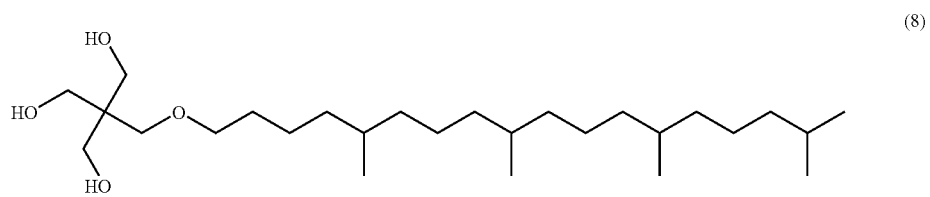
(8)

-continued

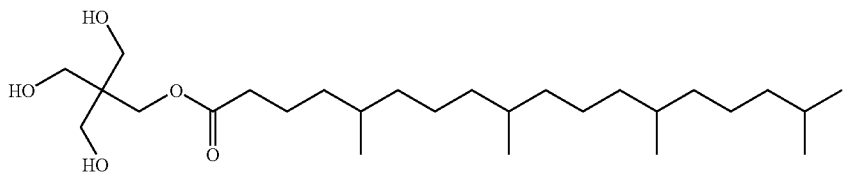
(9)

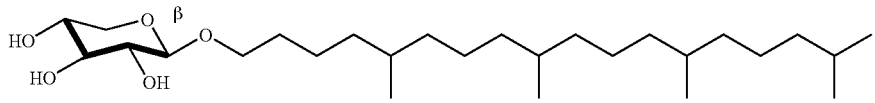
(10)

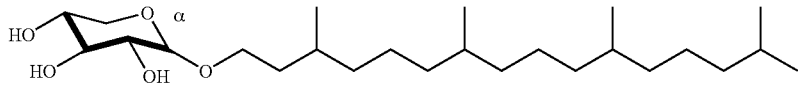
(11)

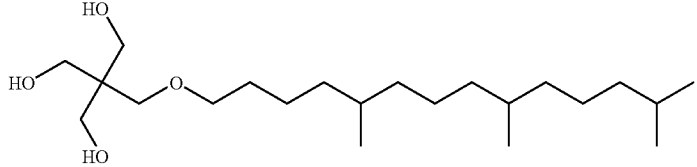
(12)

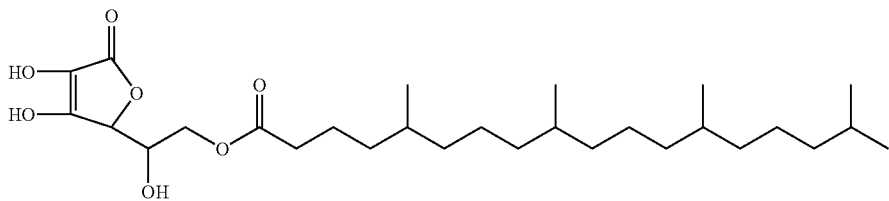
(15)

16. A method for increasing the stability of a liquid crystal structure of a cubic liquid crystal composition according to claim 1, comprising mixing at least one amphiphilic compound selected from the group consisting of formulae (2) to (12) and (15) with a curvature-regulating substance in water or an aqueous medium.

17. The method according to claim 16, wherein said curvature-regulating substance is a triglyceride-containing substance.

18. The method according to claim 16, wherein said curvature-regulating substance is olive oil.

19. The method according to claim 16, wherein a protein is further mixed together with said amphiphilic compound and said curvature-regulating substance.

20. A method for crystallizing a protein comprising embedding a protein in the cubic liquid crystal composition according to claim 1 and growing a protein crystal in the resulting complex.

* * * * *